(12) United States Patent
Scruggs et al.

(10) Patent No.: US 12,374,843 B2
(45) Date of Patent: Jul. 29, 2025

(54) POGO PIN CONNECTOR

(71) Applicant: Masimo Corporation, Irvine, CA (US)

(72) Inventors: Stephen Scruggs, Newport Beach, CA (US); Ammar Al-Ali, San Juan Capistrano, CA (US); John Schmidt, Lake Forest, CA (US); Yassir Kamel Abdul-Hafiz, Irvine, CA (US); Benjamin C. Triman, Rancho Santa Margarita, CA (US); William Jack MacNeish, III, Newport Beach, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/656,231

(22) Filed: May 6, 2024

(65) Prior Publication Data
US 2024/0364058 A1 Oct. 31, 2024

Related U.S. Application Data

(63) Continuation of application No. 17/874,071, filed on Jul. 26, 2022, now Pat. No. 12,015,226, which is a
(Continued)

(51) Int. Cl.
*H01R 24/62* (2011.01)
*H01R 13/24* (2006.01)
(Continued)

(52) U.S. Cl.
CPC ......... *H01R 24/62* (2013.01); *H01R 13/2407* (2013.01); *H01R 13/2421* (2013.01);
(Continued)

(58) Field of Classification Search
CPC ................ H01R 24/62; H01R 13/2407; H01R 13/2421; H01R 13/6271; H01R 13/6272;
(Continued)

(56) References Cited

U.S. PATENT DOCUMENTS

| 3,786,391 A | 1/1974 | Mathauser |
|---|---|---|
| 3,871,729 A | 3/1975 | Attema |

(Continued)

FOREIGN PATENT DOCUMENTS

| AU | 2014202559 | 6/2014 |
|---|---|---|
| CA | 2 072 311 | 12/1992 |

(Continued)

OTHER PUBLICATIONS

US 9,579,050 B2, 02/2017, Al-Ali (withdrawn)
(Continued)

*Primary Examiner* — Thanh Tam T Le
(74) *Attorney, Agent, or Firm* — Knobbe, Martens, Olson & Bear, LLP

(57) ABSTRACT

Various connector and sensor assemblies are described. In some embodiments, the connector and sensor assembly comprises a connector and a sensor assembly. The connector can have an opening that has a first surface and second surface that are opposite each other. The connector can have a plurality of retractable electrical connectors that extend from the first surface and a lock structure that is located on the second surface. The sensor assembly is comprised of a body portion and a proximal end. The proximal end has a top side and a bottom side. The top side includes a plurality of electrical contacts that is configured to interact with the plurality of retractable electrical connectors. The bottom side includes a key structure that is configured to interact with the lock structure in the connector.

20 Claims, 52 Drawing Sheets

Related U.S. Application Data continuation of application No. 16/998,265, filed on Aug. 20, 2020, now Pat. No. 11,437,768, which is a continuation of application No. 16/236,069, filed on Dec. 28, 2018, now Pat. No. 10,784,634, which is a continuation of application No. 15/017,349, filed on Feb. 5, 2016, now Pat. No. 10,205,291.

(60) Provisional application No. 62/152,733, filed on Apr. 24, 2015, provisional application No. 62/113,054, filed on Feb. 6, 2015.

(51) Int. Cl.
| | |
|---|---|
| *H01R 13/627* | (2006.01) |
| *H01R 13/64* | (2006.01) |
| *H01R 13/641* | (2006.01) |
| *H01R 13/648* | (2006.01) |
| *H01R 13/652* | (2006.01) |
| *A61B 5/021* | (2006.01) |
| *A61B 5/1455* | (2006.01) |
| *H01R 12/71* | (2011.01) |
| *H01R 12/72* | (2011.01) |

(52) U.S. Cl.
CPC ..... *H01R 13/6271* (2013.01); *H01R 13/6272* (2013.01); *H01R 13/64* (2013.01); *H01R 13/641* (2013.01); *H01R 13/6485* (2013.01); *H01R 13/652* (2013.01); *A61B 5/021* (2013.01); *A61B 5/1455* (2013.01); *A61B 2562/227* (2013.01); *H01R 12/714* (2013.01); *H01R 12/721* (2013.01); *H01R 2201/12* (2013.01)

(58) Field of Classification Search
CPC .. H01R 13/64; H01R 13/641; H01R 13/6485; H01R 13/652; H01R 12/714; H01R 12/721; H01R 2201/12; A61B 5/021; A61B 5/1455; A61B 2562/227
See application file for complete search history.

(56) References Cited

U.S. PATENT DOCUMENTS

| | | | |
|---|---|---|---|
| 3,941,448 A * | 3/1976 | Evans | H01R 12/79 |
| | | | 439/631 |
| 4,960,128 A | 10/1990 | Gordon et al. | |
| 4,964,408 A | 10/1990 | Hink et al. | |
| 4,992,052 A | 2/1991 | Verhoeven | |
| 5,021,812 A | 6/1991 | Kohno et al. | |
| 5,026,292 A | 6/1991 | Pickles et al. | |
| 5,041,187 A | 8/1991 | Hink et al. | |
| 5,069,213 A | 12/1991 | Hink et al. | |
| 5,079,578 A | 1/1992 | Kohno et al. | |
| 5,163,438 A | 11/1992 | Gordon et al. | |
| 5,246,003 A | 9/1993 | DeLonzer | |
| 5,319,355 A | 6/1994 | Russek | |
| 5,330,370 A | 7/1994 | Reddersen | |
| 5,337,744 A | 8/1994 | Branigan | |
| 5,341,805 A | 8/1994 | Stavridi et al. | |
| 5,377,676 A | 1/1995 | Vari et al. | |
| 5,431,170 A | 7/1995 | Mathews | |
| 5,436,499 A | 7/1995 | Namavar et al. | |
| 5,452,717 A | 9/1995 | Branigan et al. | |
| 5,456,252 A | 10/1995 | Vari et al. | |
| 5,477,418 A | 12/1995 | MacGregor et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,522,737 A | 6/1996 | Brunker et al. | |
| 5,533,511 A | 7/1996 | Kaspari et al. | |
| 5,534,851 A | 7/1996 | Russek | |
| 5,590,649 A | 1/1997 | Caro et al. | |
| 5,602,924 A | 2/1997 | Durand et al. | |
| 5,632,272 A | 5/1997 | Diab et al. | |
| 5,637,018 A | 6/1997 | Gargiulo | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,813,883 A | 9/1998 | Lin | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,049 A | 7/1999 | Petersen et al. | |
| 5,919,064 A | 7/1999 | Petersen et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,954,520 A | 9/1999 | Schmidt | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,024,592 A | 2/2000 | Pai et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,061,584 A * | 5/2000 | Lovejoy | A61B 5/6826 |
| | | | 600/344 |
| 6,062,889 A | 5/2000 | Hyland et al. | |
| 6,066,204 A | 5/2000 | Haven | |
| 6,067,462 A | 5/2000 | Diab et al. | |
| 6,081,735 A | 6/2000 | Diab et al. | |
| 6,088,607 A | 7/2000 | Diab et al. | |
| 6,089,922 A | 7/2000 | Glad et al. | |
| 6,110,522 A | 8/2000 | Lepper, Jr. et al. | |
| 6,115,256 A | 9/2000 | Centofante | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,234,807 B1 | 5/2001 | Amini et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,256,523 B1 | 7/2001 | Diab et al. | |
| 6,261,130 B1 | 7/2001 | Huynh | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,280,381 B1 | 8/2001 | Malin et al. | |

(56) References Cited

U.S. PATENT DOCUMENTS

| | | |
|---|---|---|
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,398,507 B1 | 6/2002 | Choi |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,468,101 B2 | 10/2002 | Suzuki |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,764,347 B1 | 7/2004 | Plishner |
| 6,767,252 B2 | 7/2004 | McGrath et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,857,908 B2 * | 2/2005 | Burmeister ............ H01R 12/79 439/632 |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,981,887 B1 | 1/2006 | Mese et al. |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,153,155 B1 | 12/2006 | Lee et al. |
| 7,156,683 B2 | 1/2007 | Gupta et al. |
| 7,186,966 B2 | 3/2007 | Al-Ali |
| 7,190,261 B2 | 3/2007 | Al-Ali |
| 7,204,648 B2 | 4/2007 | Aronson |
| 7,207,819 B2 | 4/2007 | Chen |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,322,838 B1 | 1/2008 | Chen et al. |
| 7,328,053 B1 | 2/2008 | Diab et al. |
| 7,332,784 B2 | 2/2008 | Mills et al. |
| 7,340,287 B2 | 3/2008 | Mason et al. |

(56) References Cited

U.S. PATENT DOCUMENTS

| | | |
|---|---|---|
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,540,752 B1 * | 6/2009 | Tucker ............... H01R 13/631 439/269.1 |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,654,850 B2 | 2/2010 | Shimizu |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,744,427 B2 | 6/2010 | Zhang et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,798,820 B2 | 9/2010 | Hong |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,652 B2 | 3/2011 | Yang et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,705 B2 | 5/2011 | Murphy |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,011,950 B2 | 9/2011 | McGrath et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,047,865 B2 | 11/2011 | Patel et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,162,684 B1 | 4/2012 | Sochor |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,202,127 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,241,053 B2 | 8/2012 | Slippy |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,273,028 B2 | 9/2012 | Harshman |
| 8,274,360 B2 | 9/2012 | Sampath et al. |
| 8,280,473 B2 | 10/2012 | Al-Ali |
| 8,287,293 B1 | 10/2012 | Gao et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |

(56) References Cited

U.S. PATENT DOCUMENTS

| | | |
|---|---|---|
| RE43,860 E | 12/2012 | Parker |
| 8,337,403 B2 | 12/2012 | Al-Ali et al. |
| 8,344,747 B2 | 1/2013 | Kazama |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,312 B2 | 4/2013 | Hung |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,439,708 B2 | 5/2013 | Colantuono et al. |
| 8,454,388 B2 | 6/2013 | Song |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,475,211 B2 | 7/2013 | Wang et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,535,088 B2 | 9/2013 | Gao |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,597,056 B2 | 12/2013 | Blanchfield et al. |
| 8,597,057 B2 | 12/2013 | Yu et al. |
| 8,600,467 B2 | 12/2013 | Al-Ali et al. |
| 8,602,801 B2 | 12/2013 | Sylvester et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,635 B2 | 6/2014 | Lim et al. |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,784,123 B1 | 7/2014 | Leiba et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,894,441 B2 | 11/2014 | Wu et al. |
| 8,897,847 B2 | 11/2014 | Al-Ali |
| 8,909,310 B2 | 12/2014 | Lamego et al. |
| 8,911,262 B1 * | 12/2014 | Leiba .................. H01R 24/60 439/79 |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,956,187 B2 | 2/2015 | He et al. |
| 8,961,235 B2 | 2/2015 | Little et al. |
| 8,965,471 B2 | 2/2015 | Lamego |
| 8,968,021 B1 | 3/2015 | Kennedy |
| 8,968,033 B2 | 3/2015 | Little |
| 8,983,564 B2 | 3/2015 | Al-Ali |
| 8,986,049 B2 | 3/2015 | Kamarauskas |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,033,744 B2 | 5/2015 | Chen |
| 9,037,207 B2 | 5/2015 | Al-Ali et al. |

(56) References Cited

U.S. PATENT DOCUMENTS

| | | |
|---|---|---|
| 9,039,448 B2 | 5/2015 | Mason et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,088,108 B2 | 7/2015 | Zhao et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,136,646 B2 | 9/2015 | Naito et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,147,965 B2 | 9/2015 | Lee |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,231,356 B1 | 1/2016 | Ju et al. |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,318,858 B2 | 4/2016 | Saito et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,385,484 B2 | 7/2016 | Chen et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,537,272 B2 | 1/2017 | Chien et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,570,842 B2 | 2/2017 | Nordgren |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,853,402 B2 | 12/2017 | Talalayev et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |

(56) References Cited

U.S. PATENT DOCUMENTS

| | | |
|---|---|---|
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,991,640 B2 | 6/2018 | Tziviskos et al. |
| 9,993,207 B2 | 6/2018 | Al-Ali et al. |
| 9,997,876 B2 | 6/2018 | Kasar et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| 10,236,632 B2 | 3/2019 | Zhang et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,320,101 B2 | 6/2019 | Brogan et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,522,943 B1 | 12/2019 | Termini et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,651,612 B2 | 5/2020 | Cheng et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,804,635 B2 | 10/2020 | Song et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |

(56) References Cited

U.S. PATENT DOCUMENTS

| | | |
|---|---|---|
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| 11,031,725 B2 | 6/2021 | Tsai et al. |
| D925,597 S | 7/2021 | Chandran et al. |
| 11,063,385 B2 | 7/2021 | Gu |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,437,768 B2 | 9/2022 | Scruggs et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,894,640 B2 | 2/2024 | Scruggs et al. |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2002/0165440 A1 | 11/2002 | Mason et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0039272 A1 | 2/2004 | Abdul-Hafiz et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |

(56) References Cited

U.S. PATENT DOCUMENTS

| | | |
|---|---|---|
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0192696 A1 | 8/2010 | Schlitzkus |
| 2010/0234718 A1 | 9/2010 | Sampath et al. |
| 2010/0267261 A1 | 10/2010 | Lin et al. |
| 2010/0270257 A1 | 10/2010 | Wachman et al. |
| 2011/0001605 A1 | 1/2011 | Kiani et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0059642 A1 | 3/2011 | Slippy |
| 2011/0082711 A1 | 4/2011 | Poeze et al. |
| 2011/0087081 A1 | 4/2011 | Kiani et al. |
| 2011/0098733 A1 | 4/2011 | Huynh |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2012/0041316 A1 | 2/2012 | Al Ali et al. |
| 2012/0046557 A1 | 2/2012 | Kiani |
| 2012/0052708 A1 | 3/2012 | Herring |
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0143062 A1 | 6/2012 | Nordgren et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0337699 A1 | 12/2013 | Chen |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275873 A1* | 9/2014 | Fries ............... H05K 1/117 439/85 |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0017831 A1 | 1/2015 | Wang |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olser |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0118868 A1 | 4/2015 | Choi |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |

(56) References Cited

U.S. PATENT DOCUMENTS

| | | |
|---|---|---|
| 2015/0222037 A1* | 8/2015 | Bulmer ............... H01R 13/113 439/660 |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224216 A1 | 8/2017 | Al-Ali |
| 2017/0224231 A1 | 8/2017 | Al-Ali |
| 2017/0224233 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |

(56) References Cited

U.S. PATENT DOCUMENTS

| | | |
|---|---|---|
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216370 A1 | 7/2019 | Schurman et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0066868 A1 | 3/2021 | Scruggs et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0017784 A1 | 1/2023 | Scruggs et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |

(56) References Cited

U.S. PATENT DOCUMENTS

| | | |
|---|---|---|
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2025/0000458 A1 | 1/2025 | Abdul-Hafiz et al. |

FOREIGN PATENT DOCUMENTS

| | | |
|---|---|---|
| CA | 2 186 885 | 8/1996 |
| CN | 1336081 | 2/2002 |
| CN | 102043203 | 5/2011 |
| CN | 102576966 | 7/2012 |
| CN | 102914401 | 2/2013 |
| CN | 103311752 | 9/2013 |
| CN | 203300846 | 11/2013 |
| CN | 107405075 | 11/2017 |
| CN | 107431301 | 12/2017 |
| EP | 0 776 070 A2 | 5/1997 |
| EP | 1 672 742 | 4/2008 |
| JP | 49-124589 | 10/1974 |
| JP | 58-153230 | 9/1983 |
| JP | 60-062163 | 5/1985 |
| JP | 02-100526 | 4/1990 |
| JP | 04-058981 | 5/1992 |
| JP | 05-200017 | 8/1993 |
| JP | 10-340758 | 12/1998 |
| JP | 2004-532526 | 10/2004 |
| JP | 2006-173107 | 6/2006 |
| JP | 2010-267512 | 11/2010 |
| KR | 10-2005-0067660 | 7/2005 |
| KR | 10-2010-0041701 | 4/2010 |
| WO | WO 03/057030 | 7/2003 |
| WO | WO 2008/118993 | 10/2008 |
| WO | WO 2009/049101 | 4/2009 |
| WO | WO 2009/055091 | 4/2009 |
| WO | WO 2010/033901 | 3/2010 |
| WO | WO 2008/126682 | 7/2010 |
| WO | WO 2011/101922 | 8/2011 |
| WO | WO 2012/003174 | 1/2012 |
| WO | WO 2016/127125 | 8/2016 |
| WO | WO 2016/127131 | 8/2016 |

OTHER PUBLICATIONS

US 2022/0192529 A1, 06/2022, Al-Ali et al. (withdrawn)
US 2024/0016391 A1, 01/2024, Lapotko et al. (withdrawn)
Invitation to Pay Additional Fees with Partial International Search dated May 2, 2016 for PCT/US2016/016883.
International Search Report and Written Opinion for PCT Application No. PCT/US2016/016890 dated Aug. 4, 2016 in 17 pages.
International Search Report and Written Opinion for PCT Application No. PCT/US2016/016883 dated Jul. 14, 2016 in 10 pages.
International Preliminary Report on Patentability and Written Opinion for PCT Application No. PCT/US2016/016890 dated Aug. 17, 2017 in 12 pages.
International Preliminary Report on Patentability and Written Opinion for PCT Application No. PCT/US2016/016883 dated Aug. 17, 2017 in 15 pages.

* cited by examiner

POGO PIN CONNECTOR

INCORPORATION BY REFERENCE TO ANY PRIORITY APPLICATIONS

This application is a continuation of U.S. patent application Ser. No. 17/874,071, filed Jul. 26, 2022, which is a continuation of U.S. patent application Ser. No. 16/998,265, filed Aug. 20, 2020, which is a continuation of U.S. patent application Ser. No. 16/236,069, filed Dec. 28, 2018, which is a continuation of U.S. patent application Ser. No. 15/017,349, filed Feb. 5, 2016, which claims the priority benefit under 35 U.S.C. § 119 (e) of U.S. Provisional Application No. 62/113,054, filed Feb. 6, 2015, and U.S. Provisional Application No. 62/152,733, filed Apr. 24, 2015, the entire contents of which are hereby incorporated by reference and should be considered a part of this specification. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to electrical connectors. More specifically, the present disclosure relates to the connection of medical sensors to instruments responsive to signals from the sensors.

BACKGROUND

Energy is often transmitted through or reflected from a medium to determine characteristics of the medium. For example, in the medical field, instead of extracting material from a patient's body for testing, light or sound energy may be caused to be incident on the patient's body and transmitted (or reflected) energy may be measured to determine information about the material through which the energy has passed. This type of non-invasive measurement is more comfortable for the patient and can be performed more quickly Non-invasive physiological monitoring of bodily function is often required. For example, during surgery, blood pressure and the body's available supply of oxygen, or the blood oxygen saturation, are often monitored. Measurements such as these are often performed with non-invasive techniques where assessments are made by measuring the ratio of incident to transmitted (or reflected) light through a portion of the body, for example a digit such as a finger, or an earlobe, or a forehead.

Durable and disposable sensors are often used for such physiological measurements. These sensors have connectors which allow detachment from the instrument or cable from the instrument.

SUMMARY OF THE DISCLOSURE

The present disclosure relates to a connector that is configured to attach both disposable and durable sensors to instruments that are responsive to signals from the sensors or the cables from the instruments. To ensure proper operation, the connector is designed to prevent incorrect attachment of the probe to the connector. Additionally, the connector allows for easy connection and release, yet prevents accidental disconnection.

In some aspects of the present disclosure are disclosed a sensor that has a low profile structure and a connector that can be configured to accommodate various sensors that measure different bodily functions. In one embodiment, the connector can accommodate a plurality of staggered retractable contacts that interact with a sensor with a plurality of staggered electrical contacts on the sensor.

In some embodiments, the present disclosure involves a connector and sensor assembly. The sensor assembly includes a connector with an opening that has a first surface and a second surface that are opposite each other. In this example, a plurality of retractable electrical connectors can extend from the first surface and a lock structure can be located on the second surface. In this embodiment, the sensor assembly includes a body portion and a proximal end. The proximal end includes a top side and a bottom side, wherein the top side includes a plurality of electrical contacts and the bottom side comprises a key structure and detent structure configured to fit into the lock structure of the connector. In this example, the proximal end of the sensor assembly is configured to be removably inserted into the opening of the connector.

DETAILED DESCRIPTION

Figure 1A:
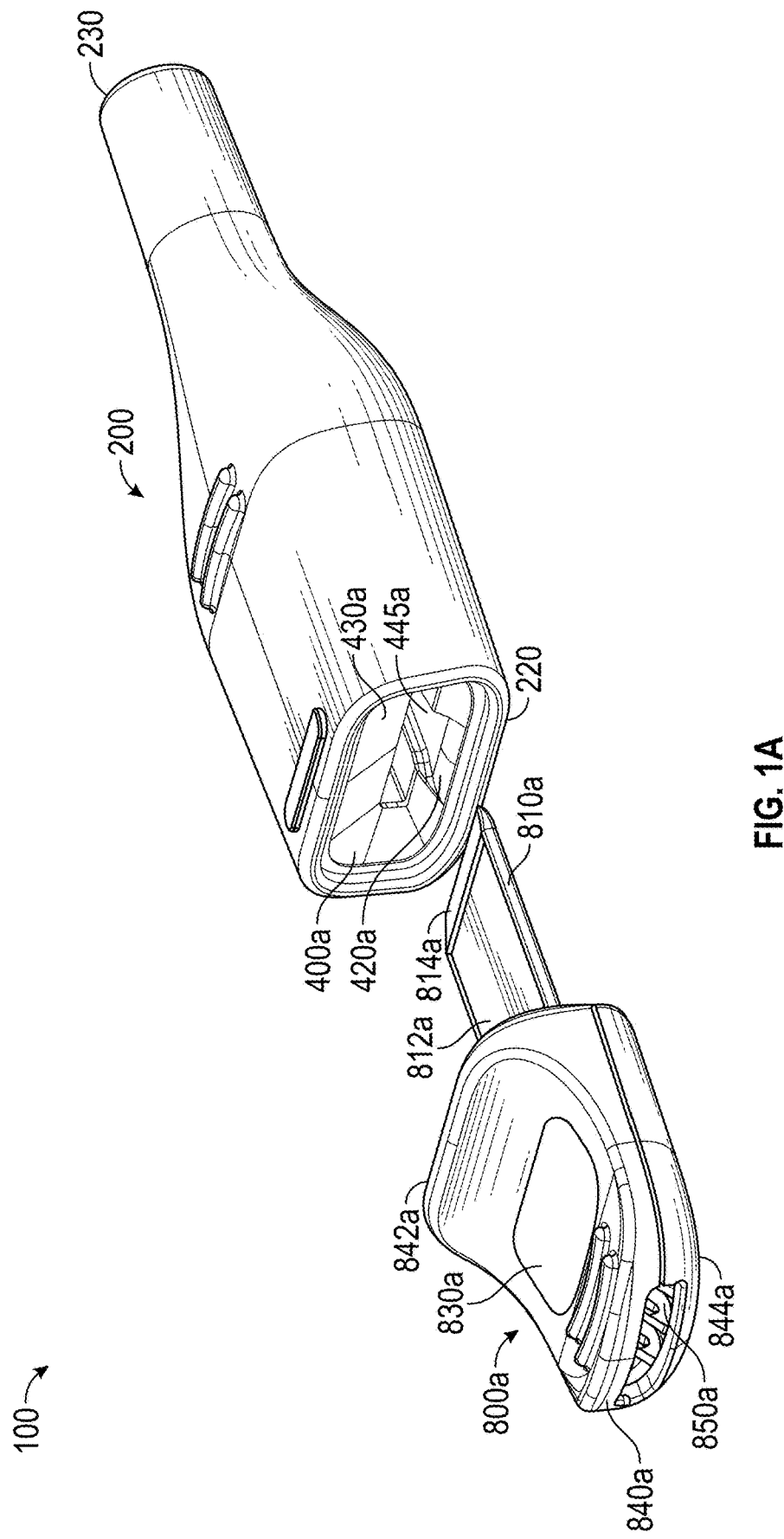
FIGS. 1A-1D illustrate perspective views of a complete assembly including one embodiment of a sensor assembly and one embodiment of a connector.
Figure 1B:
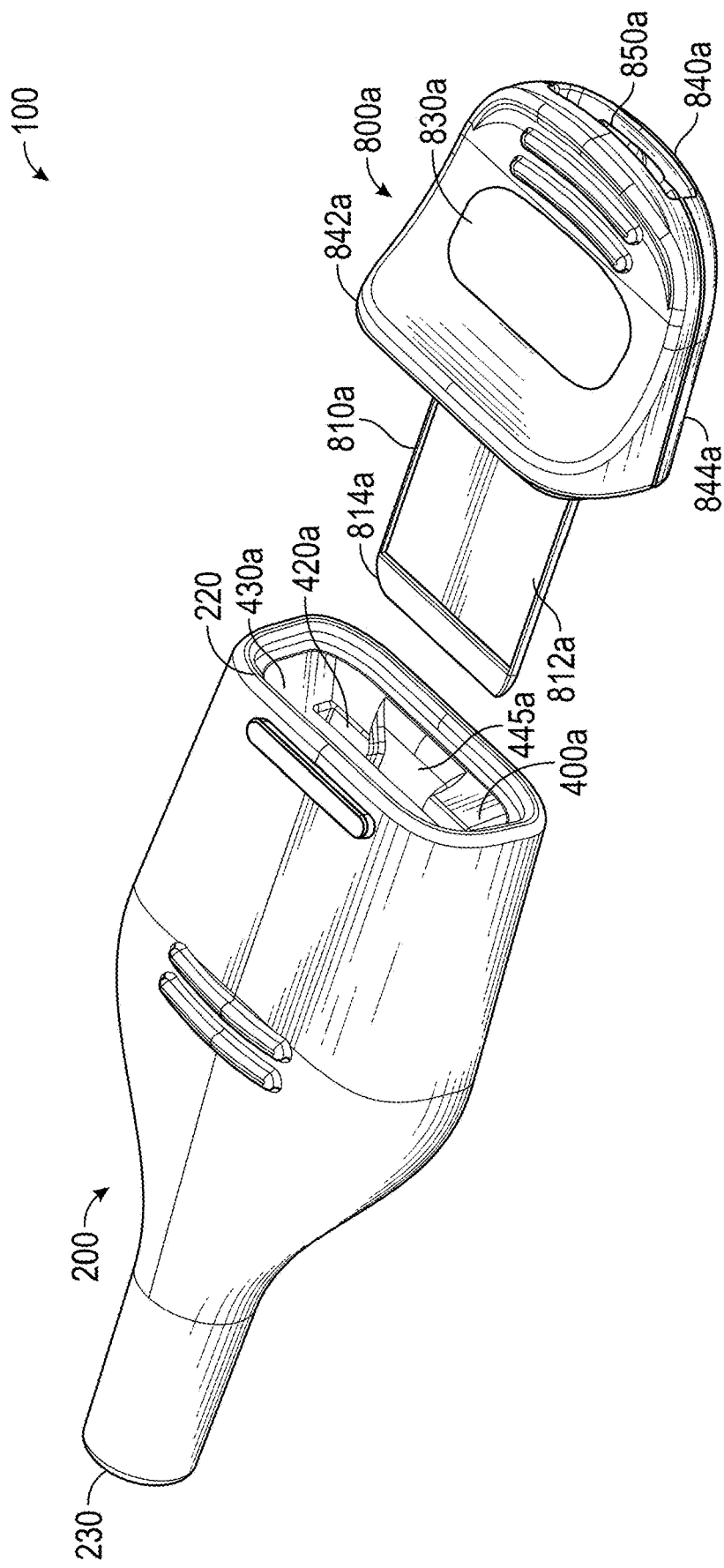
Figure 1C:
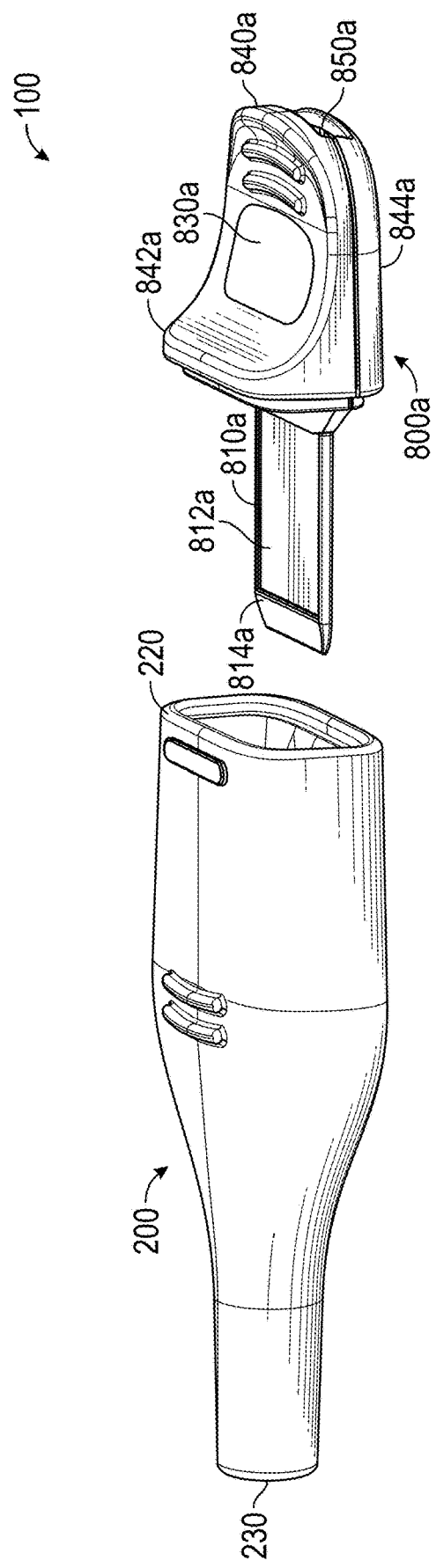

The present disclosure discloses a connector for attaching a sensor or probe to a monitor or processor so that signals from the sensor are transmitted to the processor or monitor. The connector provides easy connection and removal of the sensor to the connector while maintaining a solid connection. To ensure proper operation, the connector is designed to prevent incorrect attachment of the probe to the connector. Further, in some embodiments, the connector and sensor are configured such that both the connector and sensor structures can be adjusted to accommodate a variety of sensors that measure a variety of bodily functions.

As used in the specification, the terms "proximal" and "distal" should be understood as being relative to the contact point between the connector and sensor assembly described. Hence, the term distal means a portion of the connector and/or sensor assembly that is furthest away from the point of contact (connection point) between the connector and/or sensor. The term proximal means a portion of the connector and/or sensor assembly that is closest to the point of contact (connection point) between the connector and/or sensor assembly.

FIGS. 1A-1D illustrate a side perspective of an embodiment of the assembly 100 which includes a connector 200 and a sensor assembly 800a. The connector 200 is configured to connect with the sensor assembly 800a through the opening 420a at the proximal end of the connector 200. This allows the sensor tab 810a to be secured by the sensor assembly receiver 400a. Connector 200 can be configured to have electrical connectors that are configured to interact with a specific sensor assembly or a plurality of sensor assemblies. In one embodiment, to ensure that the proper sensor assembly is connected to the corresponding connector 200, the sensor assembly receiver 400a of the connector 200 can have an internal structure that is configured to accept only sensor assemblies with corresponding structures. This prevents errors in attaching sensors with incompatible connectors. In some examples, the connector 200 has a receptor that only accepts sensor assemblies with a corresponding key. As can be seen in FIGS. 1A-1D, the sensor assembly receiver 400a has a receptor 445a located along the bottom inner surface of the sensor assembly receiver 400a and the sensor tab 810a has a key 860a located on the underside of the sensor tab 810a. As discussed, the receptor 445a only allows a sensor assembly with a corresponding key 860a to fit into the connector 200. The location of the receptor 445a and the key 860a ensures that the user connects the sensor tab 810a with the connector 200 in the correct configuration such that the sensor side 812a sits face up.

Figure 1D:
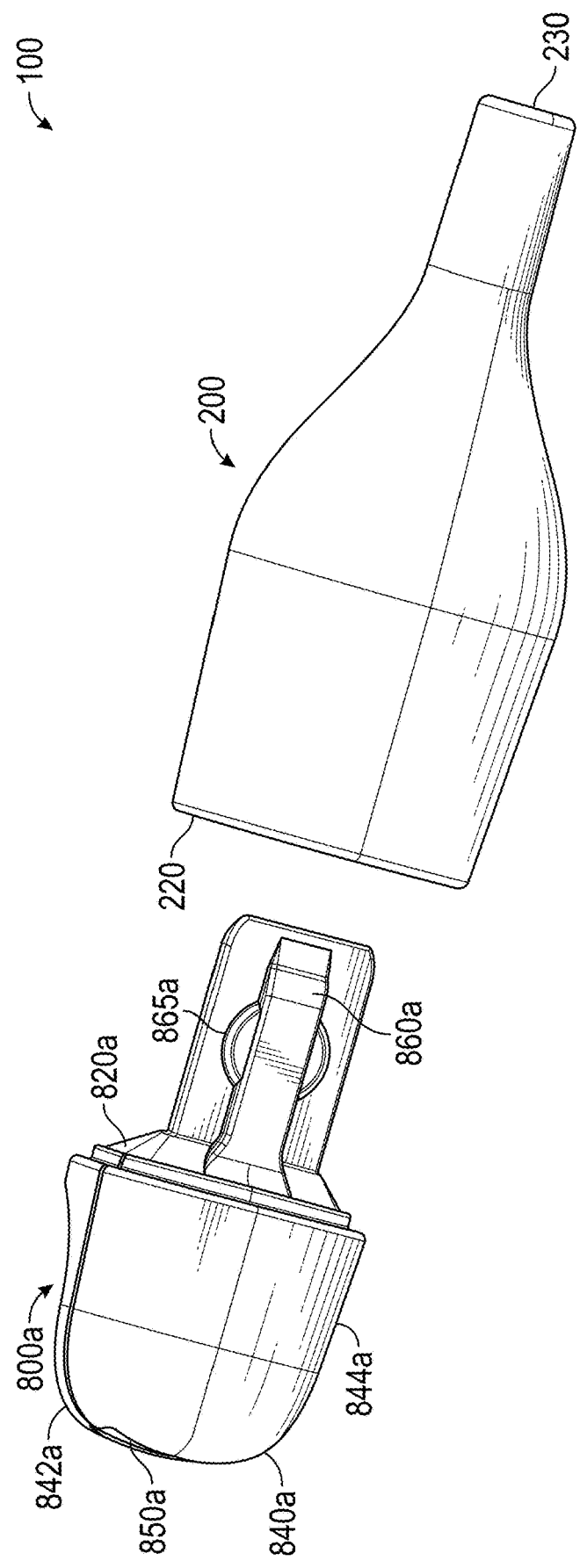

In some embodiments, the connector 200 and the sensor assembly 800a are further configured with a surface to facilitate the connection of the sensor assembly 800a with the connector 200. For example, the proximal end of the connector 200 has a front edge 220 and a tapered surface 430a which angles into the opening 420a of the sensor assembly receiver 400a. Similarly, as shown in FIG. 1D the sensor assembly 800a has a proximal end with a tapered surface 820a that is distal to the sensor tab 810a with the connector tab 840a. The angle of the tapered surface 820a corresponds with the angle of the tapered surface 430a of the connector 200 and provides a surface that allows the user to easily slide the sensor assembly 800a into the sensor assembly receiver 400a of the connector 200. The front edge 220 of the connector 200 extends to enclose the tapered surface 820a of the sensor assembly 800a such that the front edge 220 lies flush over the outer edge of the distal end of the tapered surface 820a. The flush connection between the connector 200 and the sensor assembly 800a provides a continuous structure or seal that indicates to the user that the connector 200 and the sensor assembly 800a are properly connected. The aforementioned structures allow the user to correctly attach the sensor with the connector by feel alone. This assists patients and medical practitioners in attaching the connector 200 with the sensor assembly 800a in situations where light is insufficient; thereby allowing the user to connect the connector 200 with the sensor assembly 800a without needing to look at the connector itself.

Figure 2A:
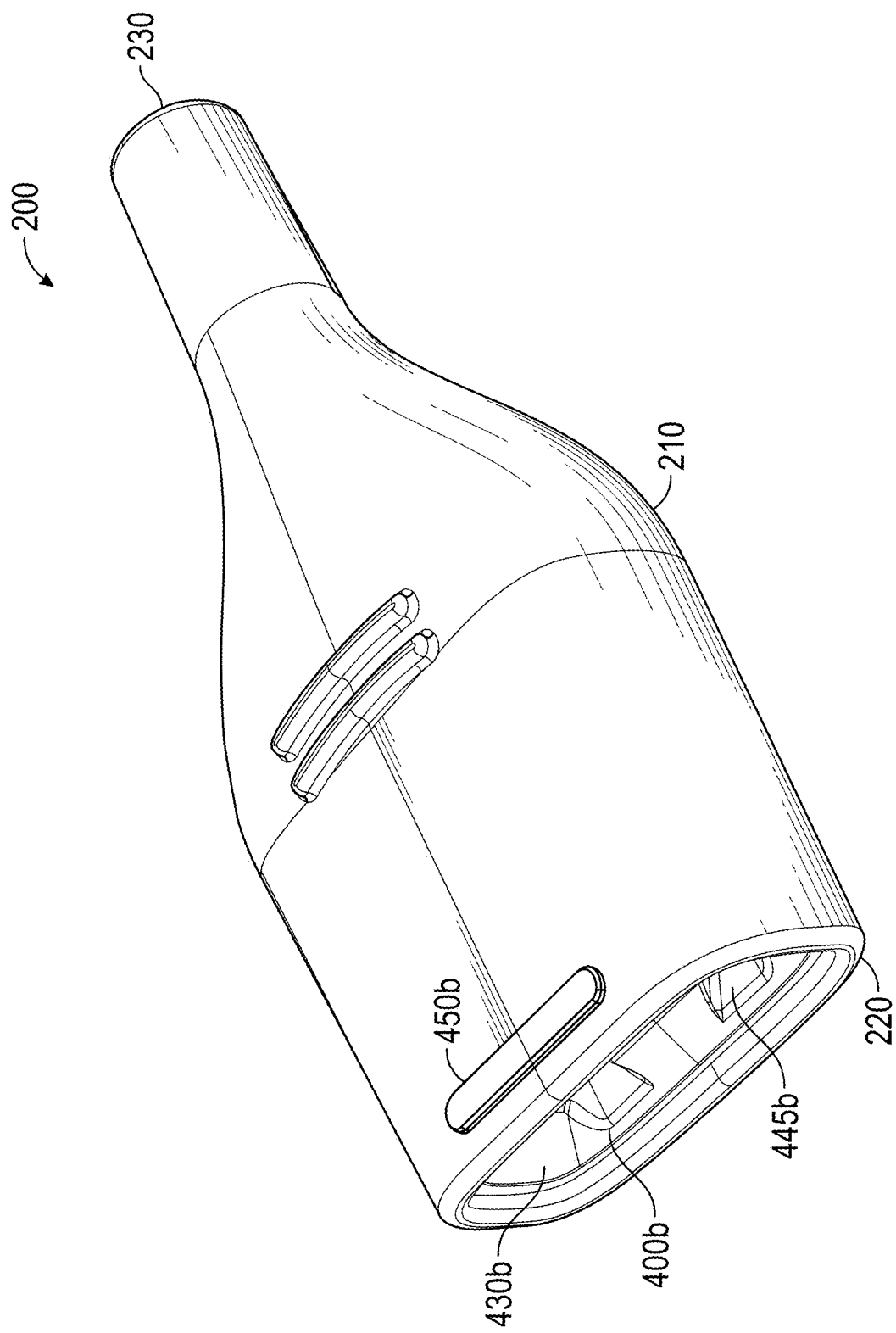
FIGS. 2A-2B illustrate a perspective and top view of one embodiment of a connector.
Figure 2B:
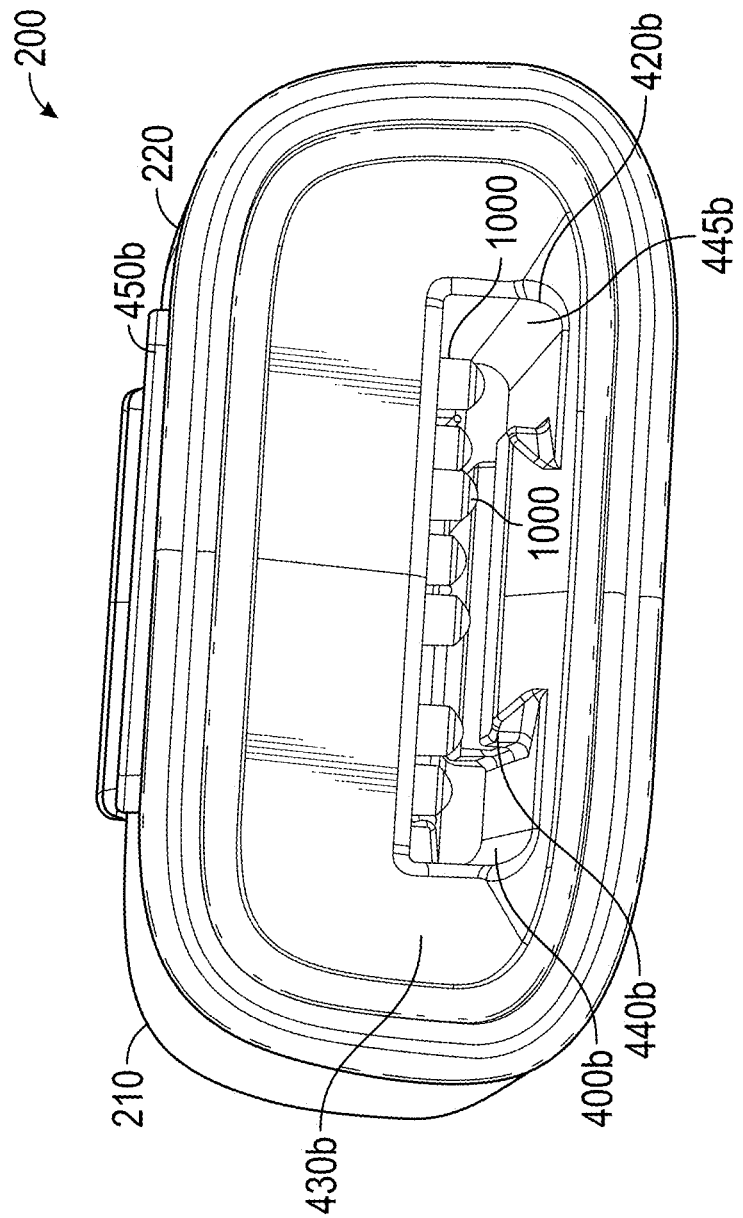
Figure 3:
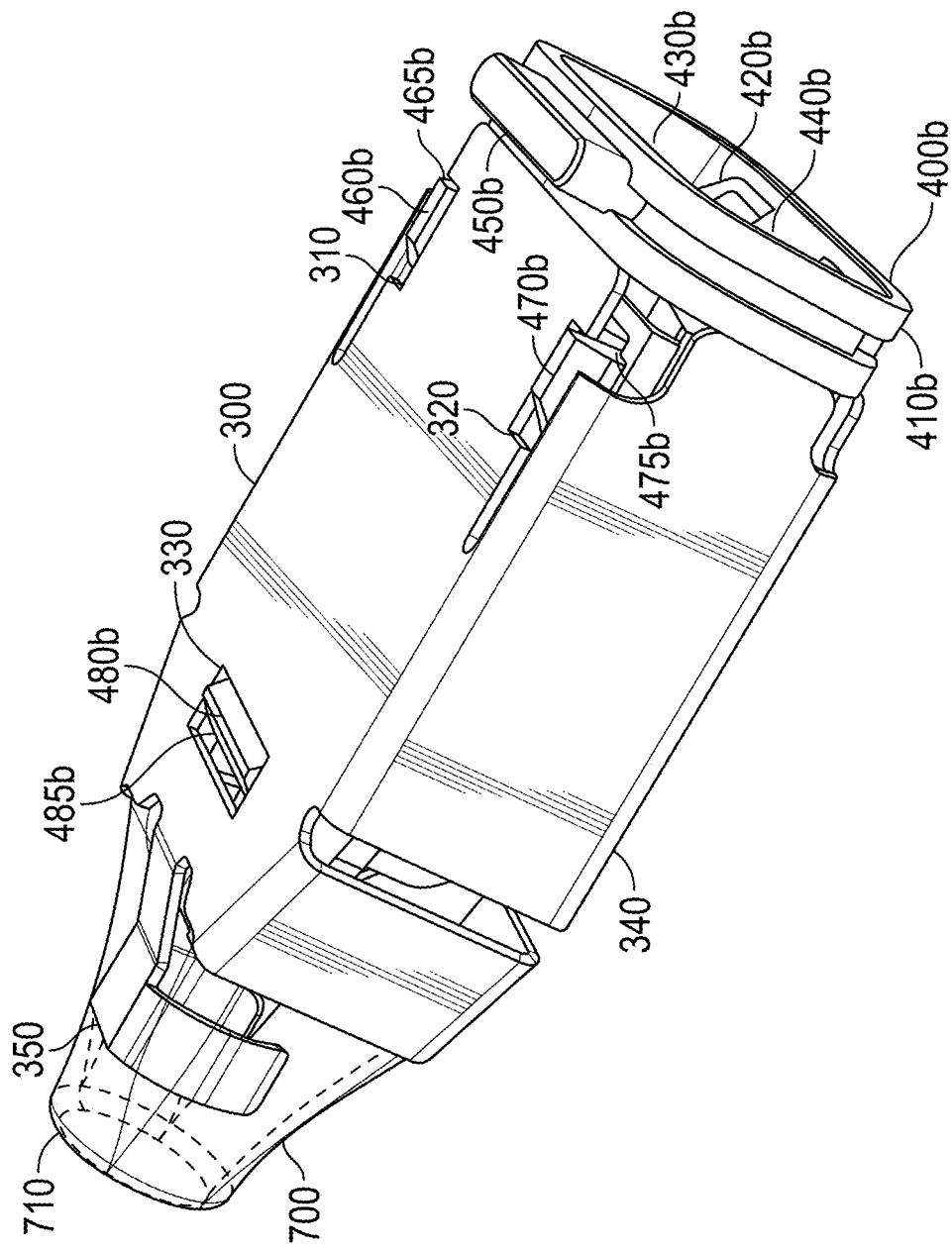
FIG. 3 illustrates side perspective view of one embodiment of a connector of FIGS. 2A-2B with the outer jacket removed.
Figure 4A:
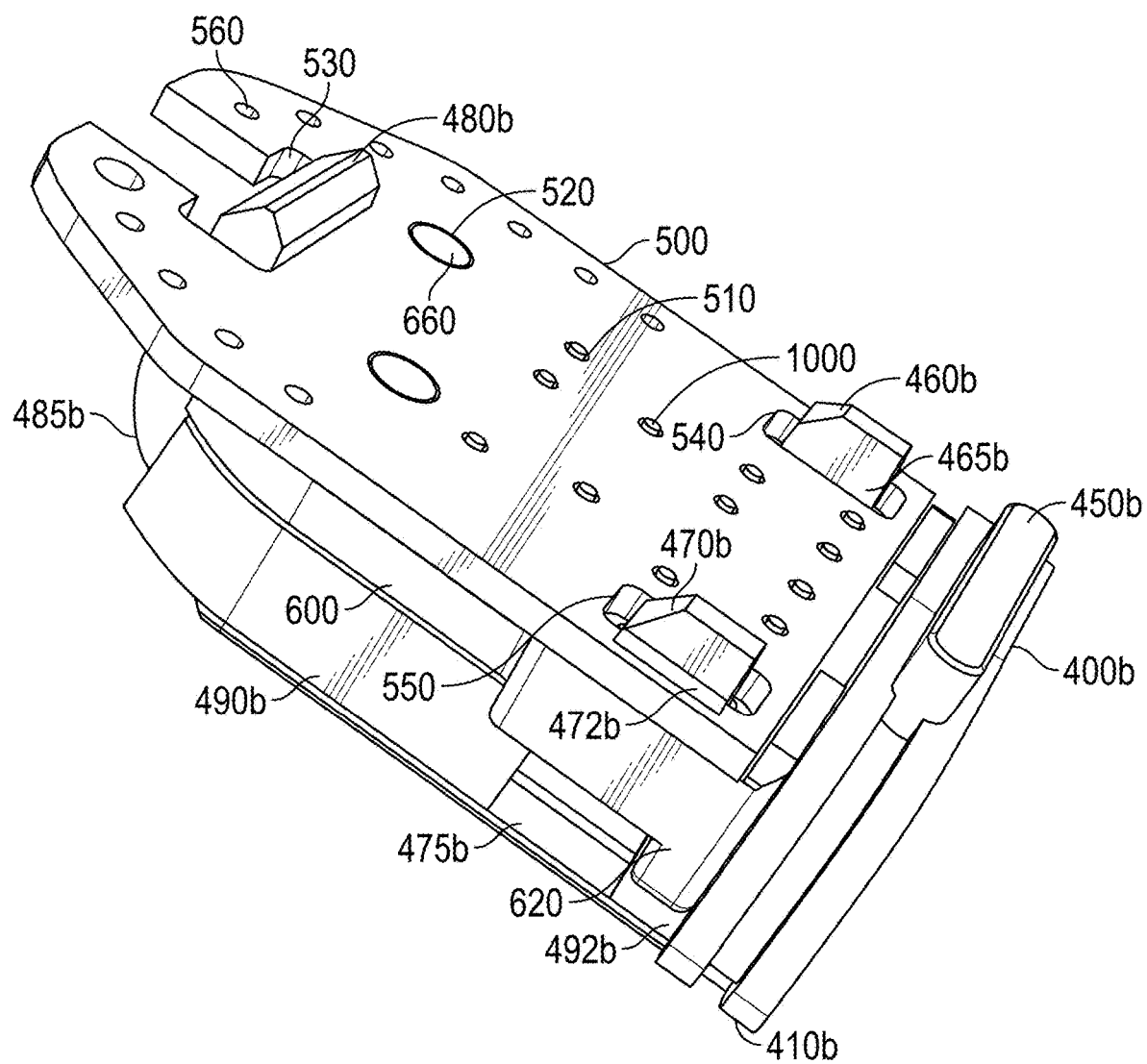
FIGS. 4A-4B illustrate a side and front perspective view of one embodiment of a connector of FIG. 3 with the outer shield removed.
Figure 4B:
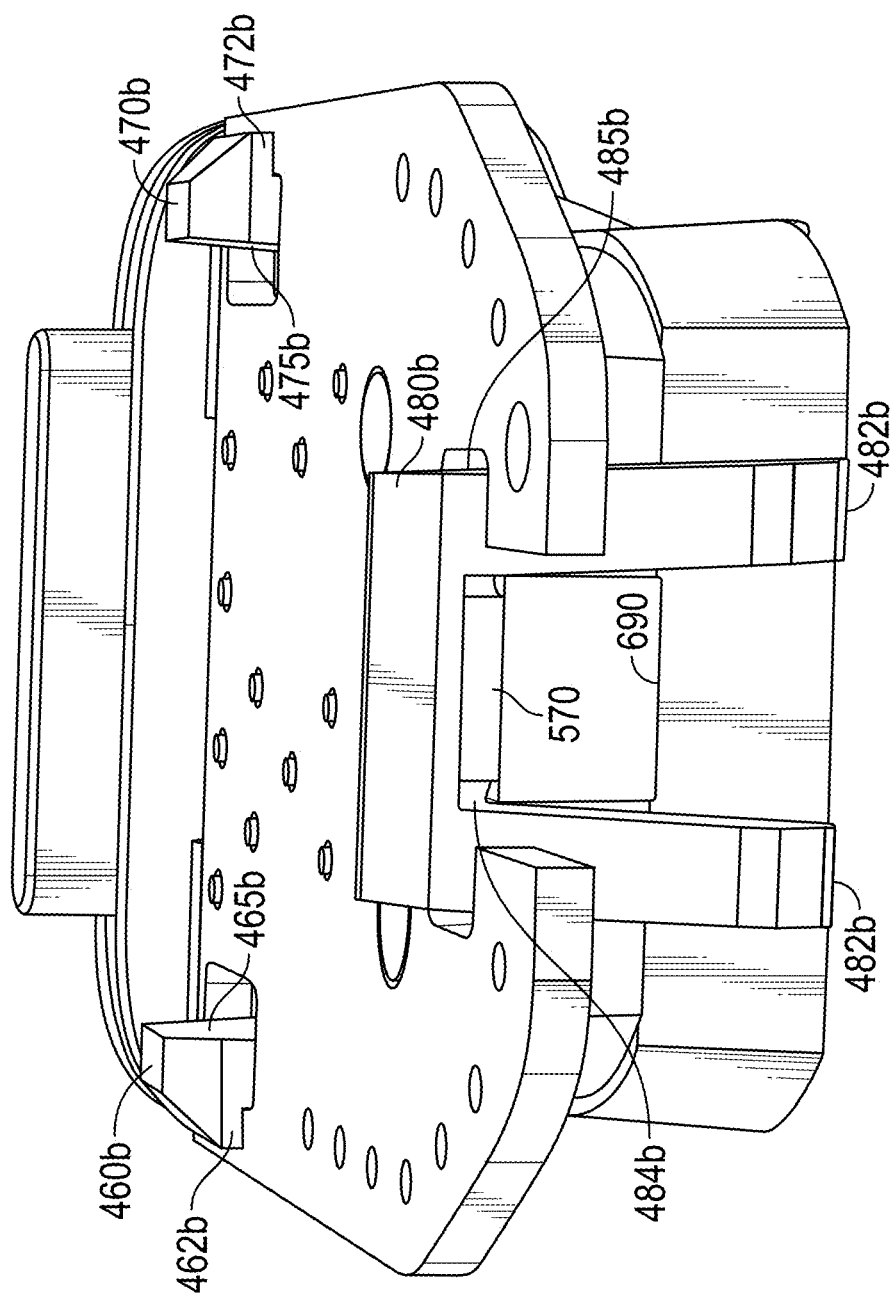
Figure 5A:
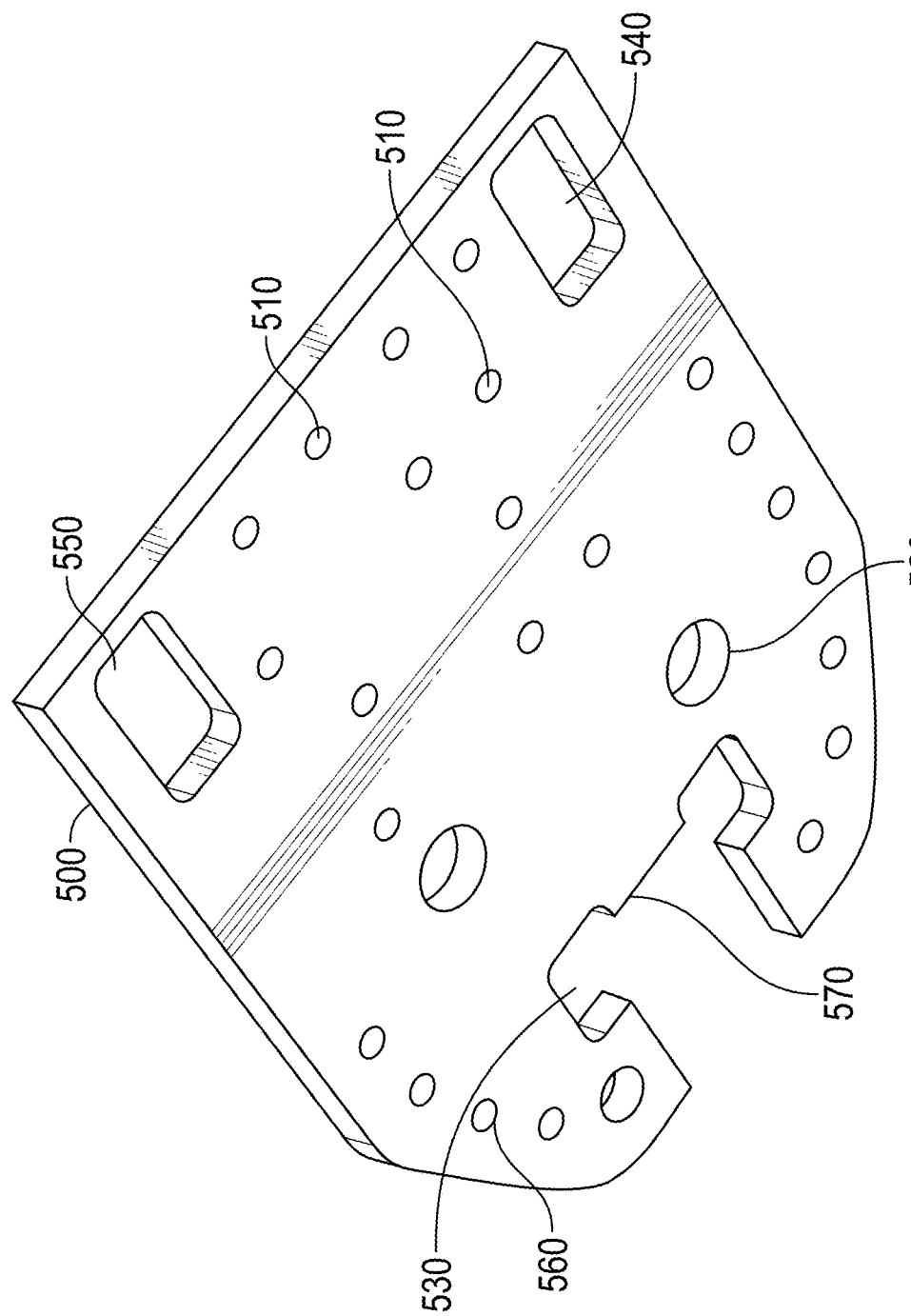
FIG. 5A illustrates a perspective bottom view of one embodiment of the printed circuit board.
Figure 6A:
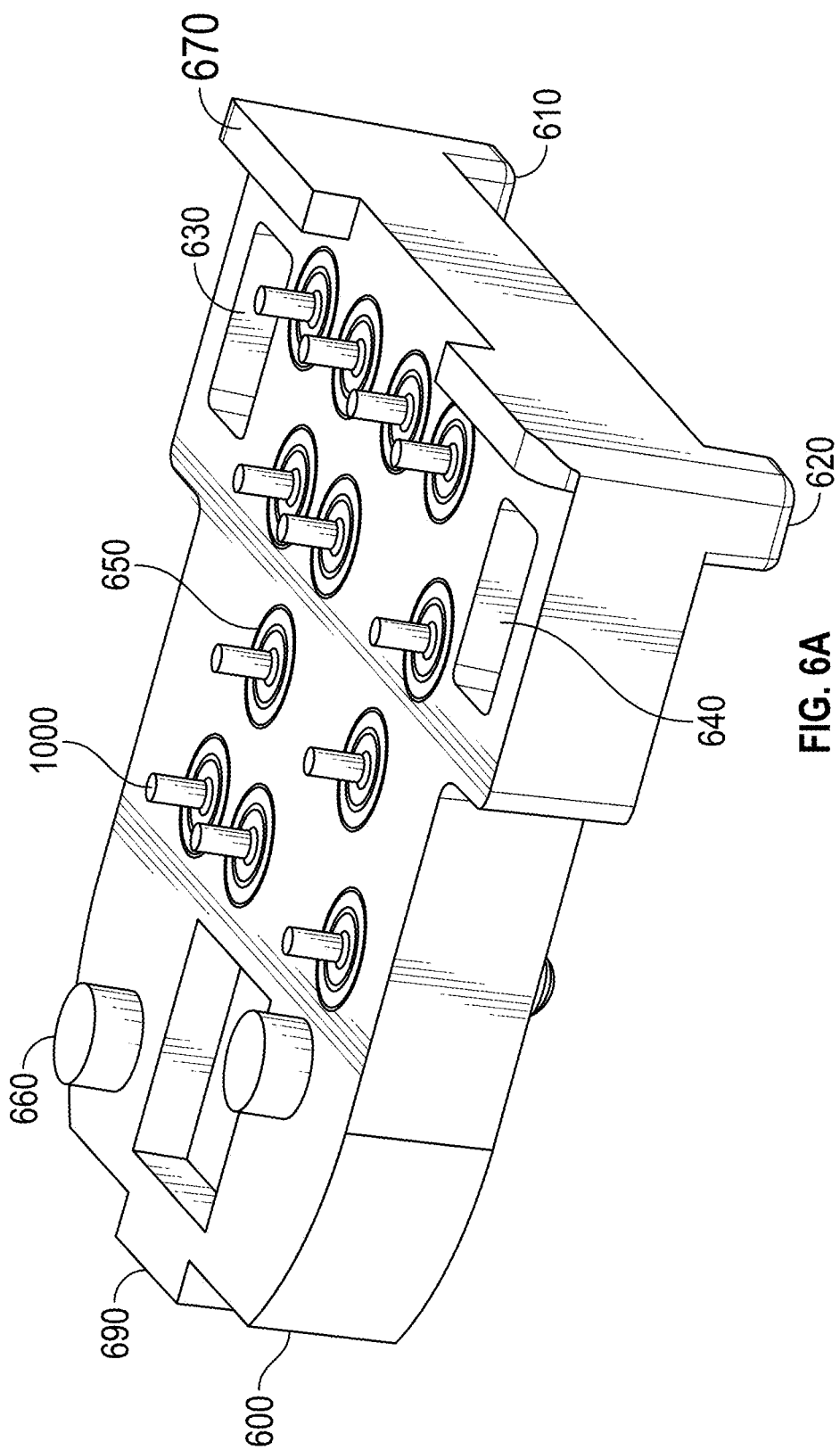
FIG. 6A illustrates a perspective view of one embodiment of the inner shield with pogo pins disposed within each of the pogo pin holes.
Figure 7A:
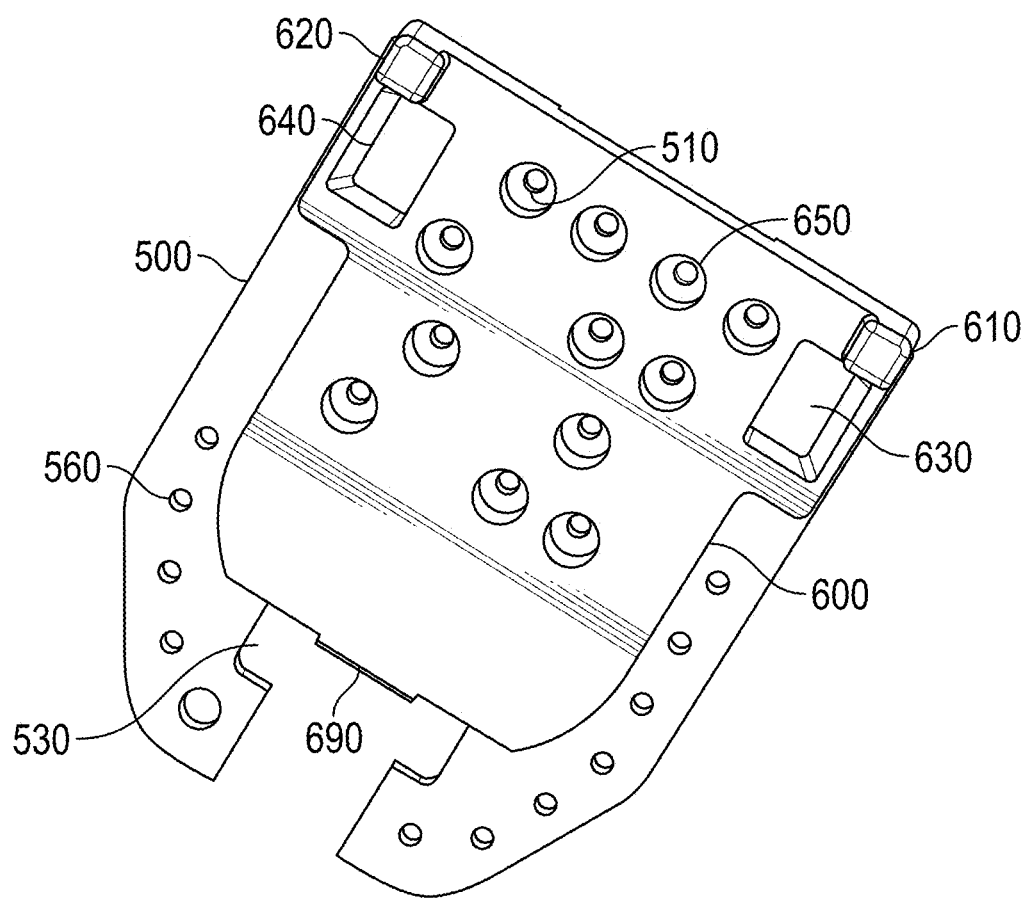
FIG. 7A illustrates a bottom view of one embodiment of the connector of FIGS. 5A & 6A with the pogo pins removed.
Figure 8A:
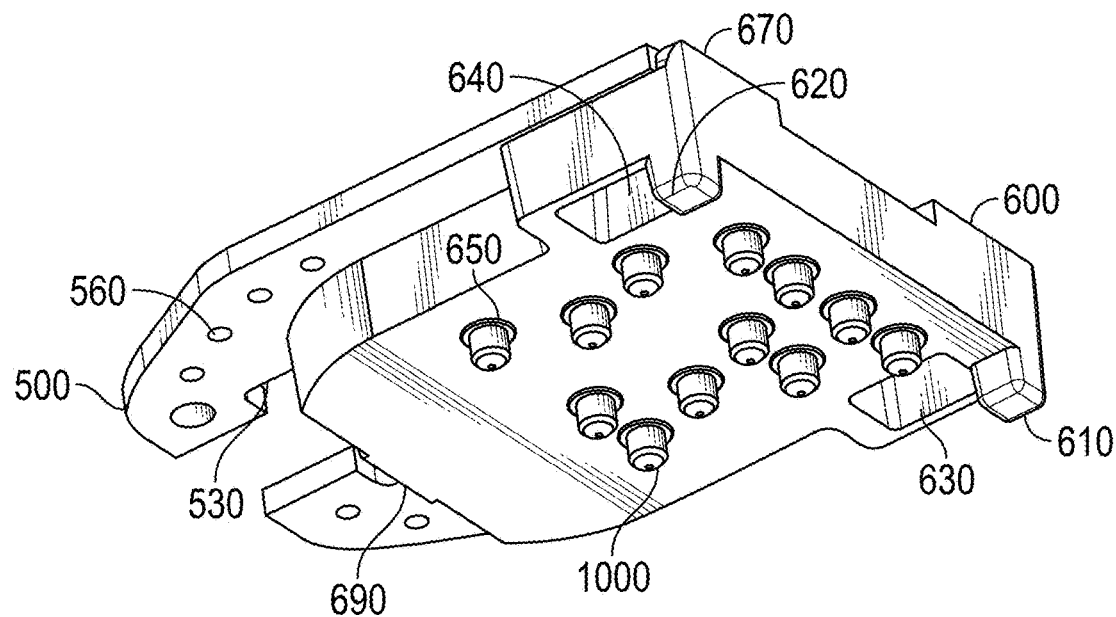
FIGS. 8A-8B illustrate a bottom perspective view of one embodiment of the connector of FIGS. 4A-4B with the inner shield removed.
Figure 8B:
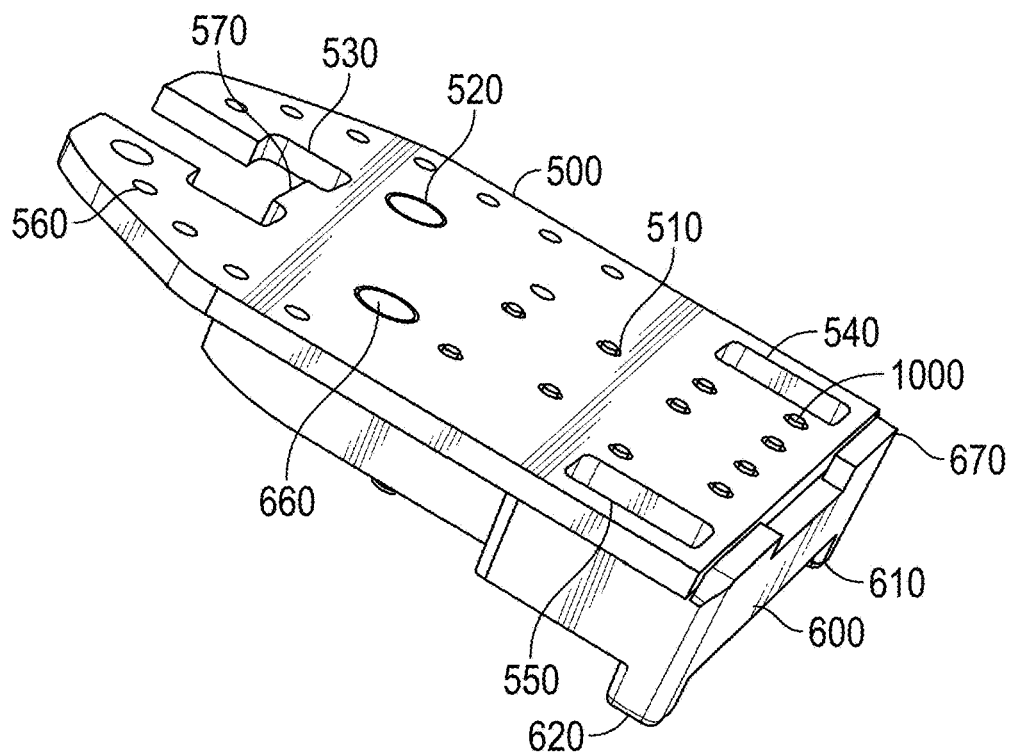

FIGS. 2A-2B provide various views of an embodiment of the connector 200. As well, FIGS. 2A-2B provide a perspective and front view of the connector 200. FIG. 3 illustrates the connector 200 with the outer jacket 210 removed such that additional internal structures of the connector 200 are visible. FIGS. 4A-4B illustrate two views of the connector 200 with the outer shield 300 removed such that the printed circuit board 500 and part of the inner shield 600 are visible. FIGS. 4A-4B also illustrate the plurality of pogo pins 1000 disposed in the holes of the printed circuit board 500 and inner shield 600. FIG. 5A illustrates a perspective view of the printed circuit board 500. FIG. 6A shows the embodiment shown in FIGS. 4A-4B with the printed circuit board 500 removed. FIG. 7A shows a bottom perspective view of the printed circuit board 500 and the inner shield 600. FIGS. 8A-8B illustrate a bottom and top perspective view of the embodiment shown in FIGS. 4A-4B with the inner shield 600 removed.

FIGS. 2A-2B illustrates a perspective and front view of the connector 200. The connector 200 includes a number of features that will be described in more detail below. The connector 200 has an outer jacket 210, a front edge 220 on the proximal end, and a cable attachment 230 at the distal end. As discussed above, the front edge 220 is configured to be disposed about the outer edge of the distal end of the tapered surface 820a. The cable attachment 230 at the distal end of the connector 200 is configured to be connected to and disposed about a cable. In some examples, the cable connects the connector 200 to a patient monitor. In some embodiments, the cable attachment 230 can be disposed about a cable with a diameter sufficient to surround a corresponding cable attachment.

FIG. 2B provides a frontal view of the connector 200. As can be seen, inside the front edge 220 of the connector 200, connector 200 has a tapered surface 430b that leads to the opening 420b of the sensor assembly receiver 400b. The top tab 450b of the sensor assembly receiver 400b protrudes from an opening on top of the outer jacket 210. This helps to retain the outer jacket 210 to the outside of the connector 200. In some embodiments, the sensor assembly receiver 400b can be one of a plurality of colors that corresponds with the color of the sensor assembly. In one example, the protruding top tab 450b can serve as a visual indicator to the user as to what sensor assembly the connector 200 can receive. The inside surface of the sensor assembly receiver 400b contains a receptor 445b that has a raised structure. As was discussed earlier, in some examples, the receptor 445b can couple with a keyed structure on the underside surface of a sensor tab such that the correct sensor assembly is connected to the proper connector 200. In some embodiments, the inside surface of the sensor assembly receiver 400b can include a detent 440b. As illustrated here, the detent 440b forms a groove on the sensor assembly receiver 400b. In some examples, the detent 440b can receive a key detent 865b. In some variants, the purpose of the detent 440b and key detent 865b is to provide the user with a tactile or mechanical feedback (e.g. a "click") to indicate to the user that the sensor assembly has been properly inserted. As will be seen and described further below, in some embodiments the connector 200 can be configured with a number of different sensor assembly receivers, each with a different receptor that is configured to accept a different shaped sensor key and different shaped detents. This provides certain manufacturing and assembly efficiencies as the outer jacket 210 and other internal components of the connector 200 can be used with sensors requiring different numbers of electrical contacts.

Connector 200 can also be structured such that it can be configured for a number of different sensors because of the manner in which the electrical connection is established between the sensor and the connector 200. As can be seen in FIG. 2B, the connector 200 can contain a plurality of electrical connectors that extend downward from the top surface of the connector 200. In some embodiments, the electrical connectors are pogo pins 1000. The configuration of the pogo pins 1000 can be adapted to connect to sensors with one of a number of electrical contacts. As will be discussed in further detail below, the pogo pins 1000 of the connector 200 can be in a staggered configuration. This configuration allows the connector 200 to accommodate sensors with varying numbers of electrical contacts.

FIGS. 3A and 4A-4B illustrate various views of the connector 200 with various parts of the connector 200 removed so as to better visualize the internal connections between the parts of the connector 200. FIG. 3A shows the connector 200 with the outer jacket 210 removed such that the outer shield 300, sensor assembly receiver 400b, and the hot melt 700 are visible.

FIGS. 4A-4B show the connector 200 with the outer shield 300 removed. In this figure, the outer shield 300, sensor assembly receiver 400b, printed circuit board 500, and inner shield 600 are visible. FIG. 4A shows a side perspective view of the connector 200 with the outer shield 300 removed. FIG. 4B shows a back perspective view of the connector 200 with the outer shield 300 removed.

As can be seen in FIG. 3, in some embodiments, the outer shield body 340 of the outer shield 300 is disposed about the various parts of the connector 200. The outer shield body 340 is disposed about the sensor assembly receiver 400b such that the proximal end 410b of the sensor assembly receiver 400b extends past the proximal end of the outer shield body 340. The top tab 450b can be located on the top of the proximal end 410b of the sensor assembly receiver 400b. At the distal end, the outer shield body 340 has a distal end holder 350. In some embodiments, the distal end holder 350 has a circular structure that can be disposed about the surface of a cable. As discussed above, the cable enters the outer jacket 210 of the connector 200 through the cable attachment 230 where it is held in place by the distal end holder 350 of the outer shield body 340. In some embodiments, to secure the cable to the connector 200, the cavity of the distal end of the connector 200 includes a hot melt 700 that secures the cable to the distal end holder 350 of the outer shield body 340. In some embodiments, the hot melt distal end 710 of the hot melt 700 secures the cable attachment 230 at the distal end of the outer jacket 210 to the cable. Depending on the internal cavity of the distal end of the connector 200, the hot melt 700 can come in a variety of sizes and shapes and can be made of a variety of materials so long as it serves to secure the cable to the connector 200.

The outer shield body 340 of the outer shield 300 can have a plurality of openings on the top surface of the outer shield body 340 in order to secure the plurality of parts of the connector 200 together. The outer shield body 340 can have two proximal openings—a first proximal opening 310 and a second proximal opening 320—located on either side of the proximal end of the outer shield body 340 and a distal opening 330 located near the distal end of the top surface of the outer shield body 340. As will be seen in subsequent figures, the sensor assembly receiver 400b has a plurality of arms that retain the plurality of interior parts of the connector 200. Each of these arms can have an end that protrudes from the outer openings of the outer shield 300 discussed above so as to retain the interior parts of the connector 200. In the embodiment pictured in FIG. 3, the sensor assembly receiver 400b has a first arm 465b with a first proximal tab 460b and a second arm 475b with a second proximal tab 470b. Both the first proximal tab 460b and the second proximal tab 470b has a top end that protrudes from the first proximal opening 310 and the second proximal opening 320 respectively. Similarly, the distal arm 485b has a pointed end 480b. The pointed end 480b has a top end that protrudes from the distal opening 330. Each of the openings of the sensor assembly receiver 400b help to contain the top ends of the first proximal tab 460b, second proximal tab 470b, and the pointed end 480b to keep the sensor assembly receiver 400b retained in the proper configuration. In some embodiments, the outer shield 300 can provide electrical shielding to the connector 200. In some embodiments, the outer shield 300 shields the connector 200 from other noise in the surrounding area.

FIGS. 4A-4B illustrate a perspective side and back view of the connector 200 with the outer shield 300 removed. As discussed above, the outer shield 300 retains a plurality of interior parts of the connector 200. In some embodiments, this includes the sensor assembly receiver 400b, the printed circuit board 500, and the inner shield 600. As will be discussed in more detail, the proximal and distal arms of the sensor assembly receiver 400b extend through openings in the printed circuit board 500 and the inner shield 600 to retain and secure the parts within the connector 200. As pictured here, the inner shield 600 and the printed circuit board 500 are stacked and located above the sensor assembly receiver 400b. In some configurations, the inner shield 600 is sandwiched between the printed circuit board 500 and the sensor assembly receiver 400b.

Similar to the outer shield body 340 discussed above, the printed circuit board 500 has a plurality of openings so as to secure the inner shield 600 and sensor assembly receiver 400b together through the arms of the sensor assembly receiver 400b. The printed circuit board 500 can have two proximal openings—a first proximal opening 540 and a second proximal opening 550—located on either side of the proximal end of the printed circuit board 500. The printed circuit board 500 can also have a distal opening 530 located at the distal end of the printed circuit board 500. As will be seen in subsequent figures, the arms of the sensor assembly receiver 400b extend through a plurality of openings in the inner shield 600 and then through the plurality of openings of the printed circuit board 500. The first arm 465b and the second arm 475b each include a lipped end—the first proximal tab 460b and the second proximal tab 470b respectively. As seen in FIG. 4B, in one embodiment, the lip 462b of the first proximal tab 460b and the lip 472b of the second proximal tab 470b extend over the first proximal opening 540 and the second proximal opening 550 and onto the outer surface of the printed circuit board 500. The lip 462b and lip 472b help to secure the sensor assembly receiver 400b to the printed circuit board 500 and the inner shield 600.

The distal opening 530 of the printed circuit board 500 and the distal arm 485b of the sensor assembly receiver 400b can also be configured to secure the printed circuit board 500 and inner shield 600 together with the sensor assembly receiver 400b. The printed circuit board 500 and the inner shield 600 can have structures that interact with the distal arm 485b. In one embodiment, the distal arm 485b has a pair of legs 482b that form an opening 484b. In this example, the printed circuit board 500 has a distal opening 530 with a distal tab 570 and the inner shield 600 has a distal tab 690. As seen in FIG. 4B, the opening 484b is disposed about the distal tab 690 and distal tab 570 that protrude from the distal ends of the inner shield 600 and printed circuit board 500 respectively. The legs 482b of the distal arm 485b extend from the base of the body 490b of the sensor assembly receiver 400b past the surface of the printed circuit board 500 to form the pointed end 480b. In one example, the size of the opening 484b is the distance between the top surface of the body 490b of the sensor assembly receiver 400b and the top surface of the distal tab 570. The opening 484b can be configured such that it contains the distal tab 570 and distal tab 690 in order to prevent the printed circuit board 500 and inner shield 600 from moving relative to each other.

FIGS. 5-8 provide various views of the printed circuit board 500 and inner shield 600 with and without the pogo pins 1000 inserted through the printed circuit board 500 and inner shield 600. FIG. 5 shows a bottom perspective view of the printed circuit board 500. FIG. 6 shows a perspective view of the inner shield 600 with a plurality of pogo pins 1000 located through the holes of the printed circuit board 500. FIG. 7 shows a bottom view of the interconnected printed circuit board 500 and inner shield 600 without the pogo pins 1000. Finally, FIGS. 8A-8B illustrate a top and bottom perspective view of the interconnected printed circuit board 500 and inner shield 600 with a plurality of pogo pins 1000 inserted in the aligned holes of the printed circuit board 500 and inner shield 600.

As shown in FIGS. 5-8, in some embodiments, the printed circuit board 500 and inner shield 600 house can retain the pogo pins 1000 that form the electrical connections between the electrical contacts in the connector 200 and the sensor. In order to retain the pogo pins 1000 and provide for their movement, the printed circuit board 500 and inner shield 600 have a plurality of holes. The holes for the printed circuit board 500 and inner shield 600 must be aligned in the connector 200 to allow for movement of the pogo pins 1000. In some embodiments, as discussed above, the printed circuit board 500 and inner shield 600 are retained in the proper configuration in the connector 200 by the plurality of arms of the sensor assembly receiver 400b.

As seen in FIG. 5, the printed circuit board 500 can be thin with a flat proximal end and a curved distal end. As discussed above, the printed circuit board 500 can have a first proximal opening 540 and a second proximal opening 550 on either side of the proximal end of the printed circuit board 500. As shown in FIG. 4A, each of these openings is configured to be disposed about the arms of the sensor assembly receiver 400b. As well, the printed circuit board 500 has a distal opening 530 at the distal end of the printed circuit board 500. In the distal opening 530, a distal tab 570 protrudes into the distal opening 530. As was discussed earlier with regard to FIG. 4B, the distal tab 570 fits in the opening 484b of the distal arm 485b. The opening 484b can secure both the distal tab 570 and the distal tab 690 against the sensor assembly receiver 400b to prevent the printed circuit board 500 and inner shield 600 from moving relative to each other.

The printed circuit board 500 can also include a plurality of small holes 510, large holes 520, and outer holes 560. In one embodiment, the small holes 510 accommodate the plurality of pogo pins 1000. In some embodiments, the large holes 520 can accommodate the plurality of connector pins 660 of the inner shield 600. The plurality of connector pins 660 can retain the printed circuit board 500 to the inner shield 600. This can provide additional structure to secure the inner shield 600 with the circuit board. As seen in FIG. 5, in one embodiment, the small holes 510 are located on the printed circuit board 500 in a staggered configuration. In some embodiments, electrical contacts can be located on top side of the printed circuit board 500. Finally, in some embodiments, the printed circuit board 500 can include a plurality of outer holes 560 located near the border of the printed circuit board 500 for case in manufacturing and assembly.

FIG. 6 illustrates the inner shield 600 with a plurality of pogo pins 1000 located in the inner shield 600. In some embodiments, the inner shield 600 includes a plurality of structures that ensures the proper positioning of the inner shield 600 in the connector 200. Like the printed circuit board 500 and the outer shield 300, the inner shield 600 can include a plurality of openings and tabs to interact with the arms of the sensor assembly receiver 400b such that the inner shield 600 is retained in a proper configuration on the sensor assembly receiver 400b and in the connector 200. The inner shield 600 has a first opening 630, a second opening 640, and a distal tab 690. As discussed earlier, the first opening 630 and second opening 640 are aligned with the first proximal opening 540 and second proximal opening 550 of the printed circuit board 500 respectively. These openings are disposed about the first arm 465b and second arm 475b of the sensor assembly receiver 400b. As well, the printed circuit board 500 and inner shield 600 are secured by the first proximal tab 460b and the second proximal tab 470b. The inner shield 600 further has a distal tab 690. The distal tab 690 protrudes from the distal end of the inner shield 600 and, as described above, can be retained by the opening 484b of the distal arm 485b of the sensor assembly receiver 400b.

The inner shield 600 can also include a plurality of legs to secure the inner shield 600 on the sensor assembly receiver 400b. As shown in FIG. 6, the inner shield 600 has a first leg 610 and a second leg 620 located at the proximal end of the inner shield 600. As can be seen in FIG. 4A, the sensor assembly receiver 400b has a plurality of gaps 492b that are located on either side of the proximal end of the sensor assembly receiver 400b. In some embodiments, the gaps 492b are formed on the side of the sensor assembly receiver 400b by the space between the proximal end of the arm (e.g. the first arm 465b or the second arm 475b) and the distal side of the proximal end 410b of the sensor assembly receiver 400b. The gaps 492b can be configured to fit the width of the legs (e.g. the first leg 610 and second leg 620) and secure the inner shield 600 in place to prevent it from moving relative to the sensor assembly receiver 400b. In this embodiment, the first leg 610 and second leg 620 bring the proximal shelf 670 such that it lies flush against the distal side of the proximal end 410b of the sensor assembly receiver 400b.

The inner shield 600 can also include a number of structures so as to retain and properly position the printed circuit board 500 on the surface of the printed circuit board 500. As shown in FIG. 6, the inner shield 600 can have a plurality of connector pins 660 and a proximal shelf 670. As discussed above the plurality of connector pins 660 can align with the plurality of large holes 520 of the printed circuit board 500 such that the large holes 520 are configured to be disposed about the connector pins 660. The inner shield 600 also includes a plurality of pogo pin holes 650. The plurality pogo pin holes 650 are located in a staggered configuration such that each of the plurality of the pogo pin holes 650 can be aligned to correspond with the small holes 510 of the printed circuit board 500. The connector pin 660 of the inner shield 600 can interact with the large holes 520 to maintain the passageway created by the small holes 510 and pogo pin holes 650. This connection can be further seen in FIG. 7. FIG. 7 shows a bottom view of the inner shield 600 with the printed circuit board 500 aligned over it. The pogo pin holes 650 of the inner shield 600 can be larger in diameter than the small holes 510 of the printed circuit board 500. In the embodiment shown in FIG. 7, each of the small holes 510 can be coaxially aligned with each of the pogo pin holes 650 so as to allow a pogo pin 1000 to be retained and move within the passage (e.g. channel, pathway) created by the pogo pin hole 650 and small hole 510.

As can be seen in FIGS. 8A and B, the pogo pin holes 650 are configured such that the plurality of pogo pins 1000 are positioned in the pogo pin holes 650 such that both ends of each of the pogo pins 1000 can protrude from the inner shield 600. The distal end 1110 of the pogo pins 1000 contacts the printed circuit board 500 and allows for an electrical connection to be formed between the printed circuit board 500 and the pogo pins 1000. As will be further discussed below, the small holes 510 of the printed circuit board 500 and the internal structure of each of the pogo pin holes 650 help to retain each of the pogo pins 1000 to prevent it from moving out of the pogo pin holes 650 of the inner shield 600. Also, as will be discussed below, the pogo pins 1000 are retained in a staggered configuration that can accommodate sensors with a range of electrical contacts. This staggered configuration can help to reduce the profile of the connector 200 and allow the same connector 200 structure to be used in a large number of sensors.

In some examples, the connector 200 can have internal components (e.g. the sensor assembly receiver, printed circuit board, and inner shield) with different configurations. FIGS. 4C-4D, 5B, 6B, 7B, and 8C-8D, illustrate another embodiment of the internal components of the connector 200.

Figure 4C:
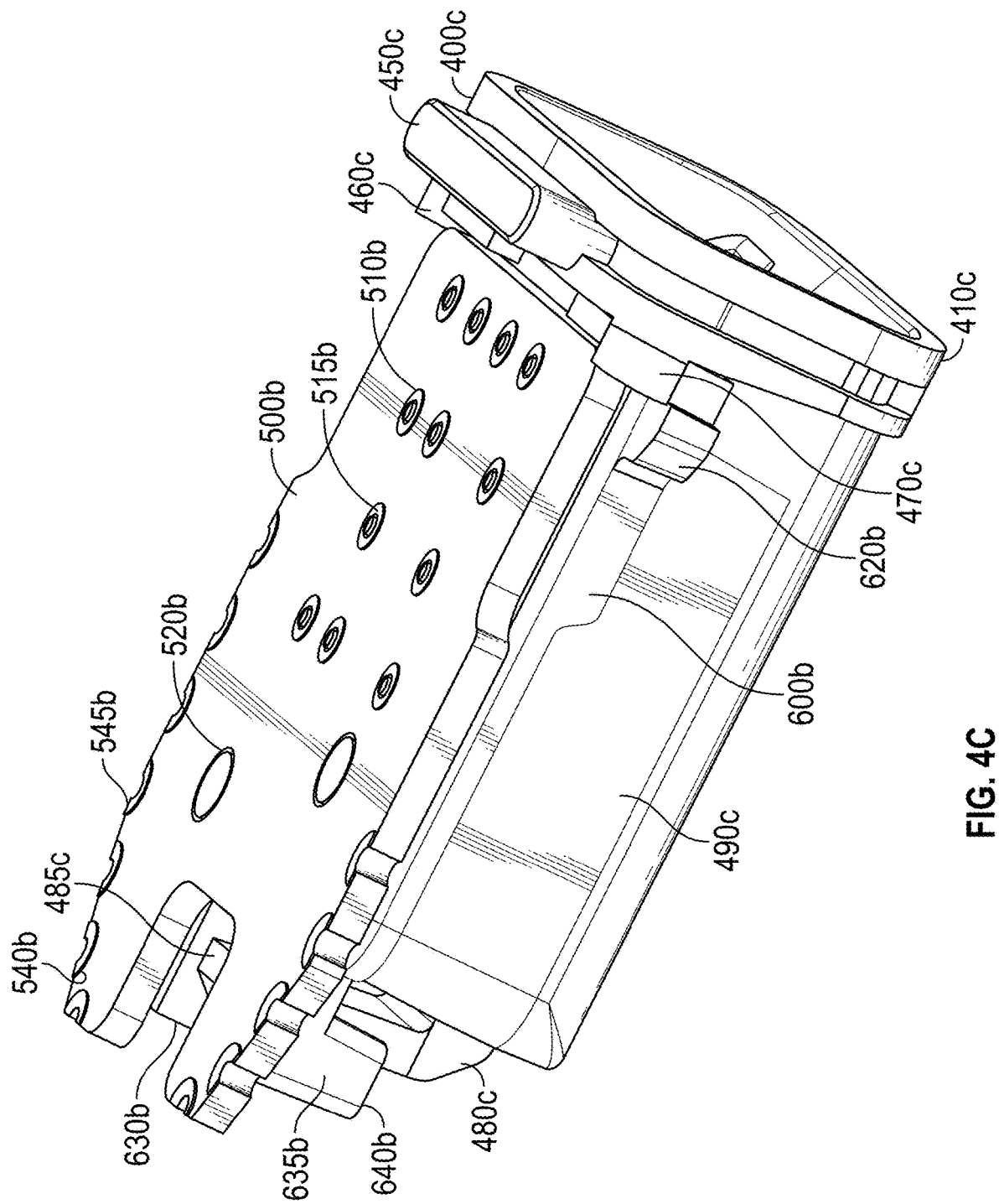
FIGS. 4C-4D illustrate a side and front perspective view of another embodiment of a connector of FIG. 3 with the outer shield removed.
Figure 4D:
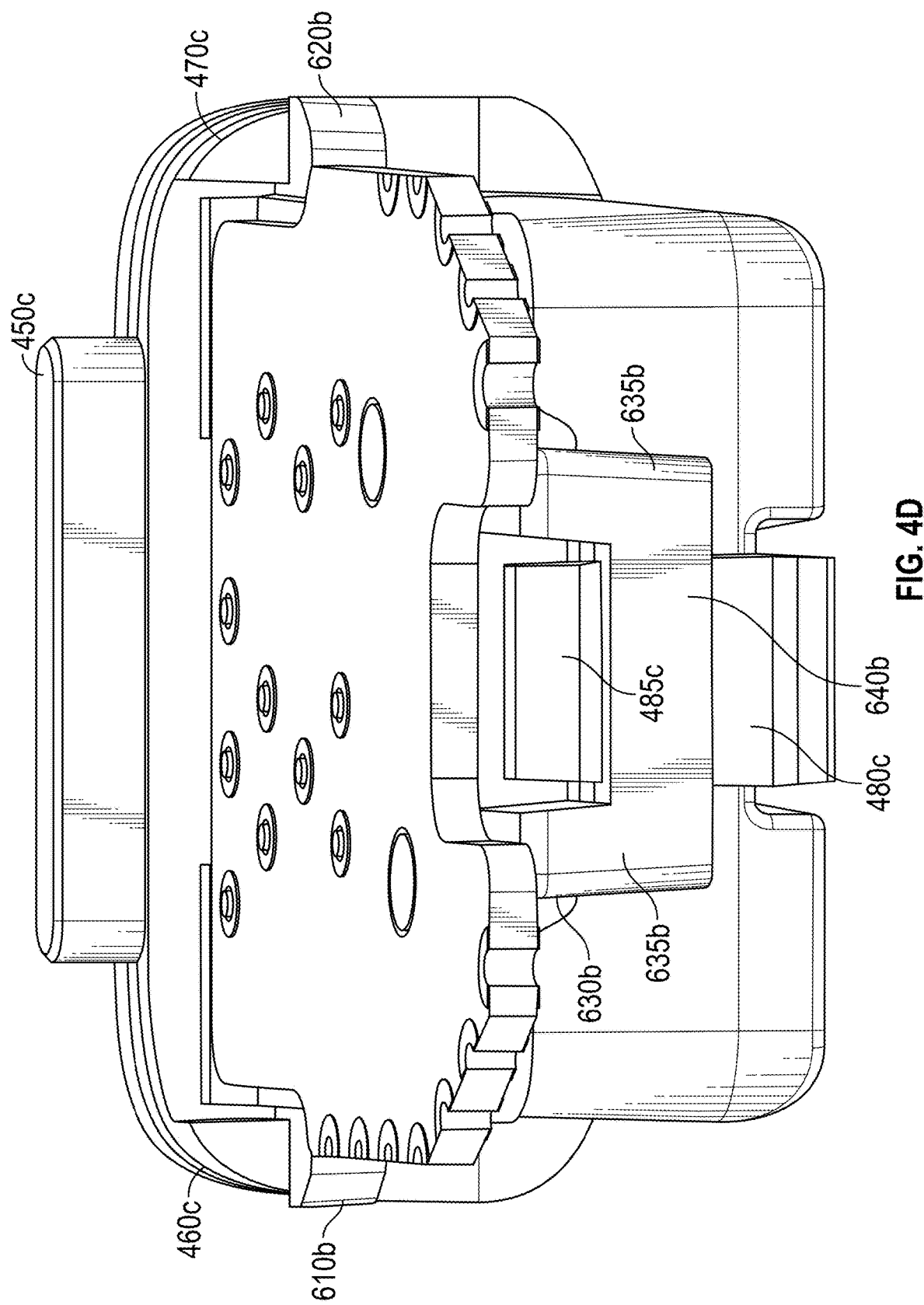

FIGS. 4C-4D illustrate a perspective side and back view of another embodiment of connector 200 with the outer shield 300 removed. As discussed above, the outer shield 300 retains a plurality of interior parts of the connector 200. In some embodiments, this includes the sensor assembly receiver 400c, the printed circuit board 500b, and the inner shield 600b. As pictured here, the inner shield 600b and the printed circuit board 500b can be stacked and located above the sensor assembly receiver 400c. In some configurations, the inner shield 600b can be sandwiched between the printed circuit board 500b and the sensor assembly receiver 400c.

The printed circuit board 500b can have a plurality of openings so as to secure the printed circuit board 500b on the inner shield 600b. As will be discussed in more detail below, the printed circuit board 500b can include a plurality of large holes 520b that are disposed about the connector pin 660b of the inner shield 600b.

The sensor assembly receiver 400c can include a plurality of arms that secure the inner shield 600b to the sensor assembly receiver 400c so as to prevent movement of the inner shield 600b relative to the sensor assembly receiver 400c. In some embodiments the sensor assembly receiver 400c can include a first arm 460c, a second arm 470c, and a distal arm 480c. As seen in FIGS. 4C and 4D, in some embodiments the first arm 460c and second arm 470c can be located on the proximal end 410c of the sensor assembly receiver 400c. In one embodiment, the first arm 460c and second arm 470c extend away from the body 490c.

Similarly, in some embodiments, the inner shield 600b can include a plurality of arms that are configured to engage with the sensor assembly receiver 400c in order to secure the sensor assembly receiver 400c to the inner shield 600b. In one embodiment, the inner shield 600b can include a first arm 610b, a second arm 620b, and a distal arm 630b. In some embodiments, the first arm 610b and second arm 620b can be located on the proximal end of the inner shield 600b and the first arm 610b and second arm 620b extend outward from the inner shield 600b. The distal arm 630b can be located on the distal end of the first arm 610b. In some embodiments, the distal arm 630b can be composed of two legs 635b that extend away from the distal end of the inner shield 600b. In some embodiments, the two legs 635b bend away from the distal end of the inner shield 600b. In some embodiments, the ends of the two legs 635b have a connected end 640b and form an opening.

FIGS. 4C-4D illustrate one example of the connections between the sensor assembly receiver 400c and the inner shield 600b on the proximal end. In some embodiments, the first arm 460c and second arm 470c can extend outward to engage the proximal end of the inner shield 600b. In some variants, this engagement can allow the proximal shelf 670b to lie flush against the distal surface of the proximal end 410c of the sensor assembly receiver 400c. In some embodiments, the proximal shelf 670b is located between the first arm 460c and the second arm 470c.

FIG. 4D provides an illustration of one example of the connection between the sensor assembly receiver 400c and the inner shield 600b. As illustrated, the two legs 635b of the connected end 640b of the distal arm 630b can form an opening. As seen in FIG. 4D, the opening can allow the distal tab 485c of the distal arm 480c to protrude over the top surface of the connected end 640b. In some embodiments, this connection can prevent the inner shield 600b and sensor assembly receiver 400c from moving relative to each other. As well, as was discussed above, this securement can ensure the proper placement of the plurality of pogo pins 1000 within the body of the sensor assembly receiver 400c.

Figure 5B:
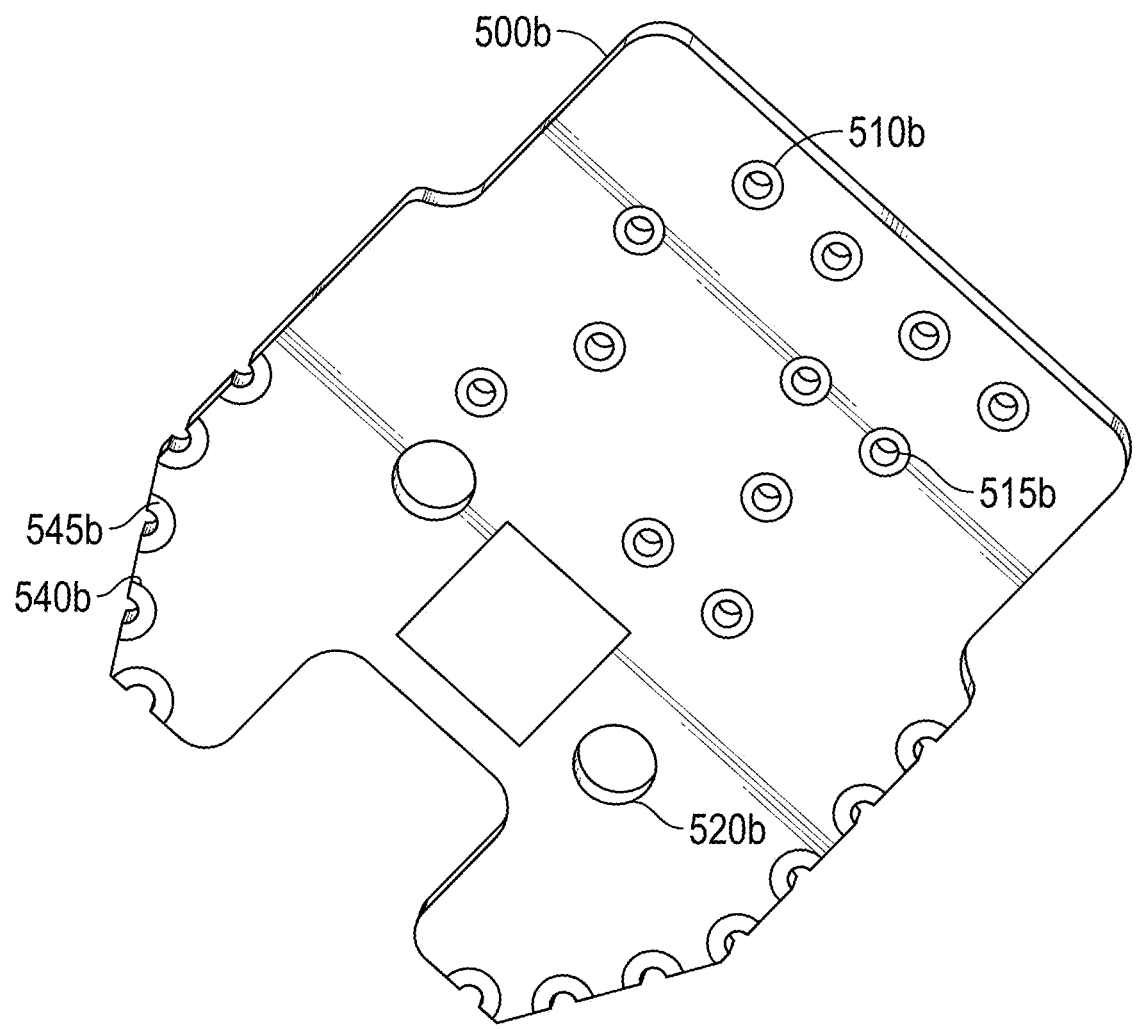
FIG. 5B illustrates a perspective bottom view of another embodiment of the printed circuit board.
Figure 6B:
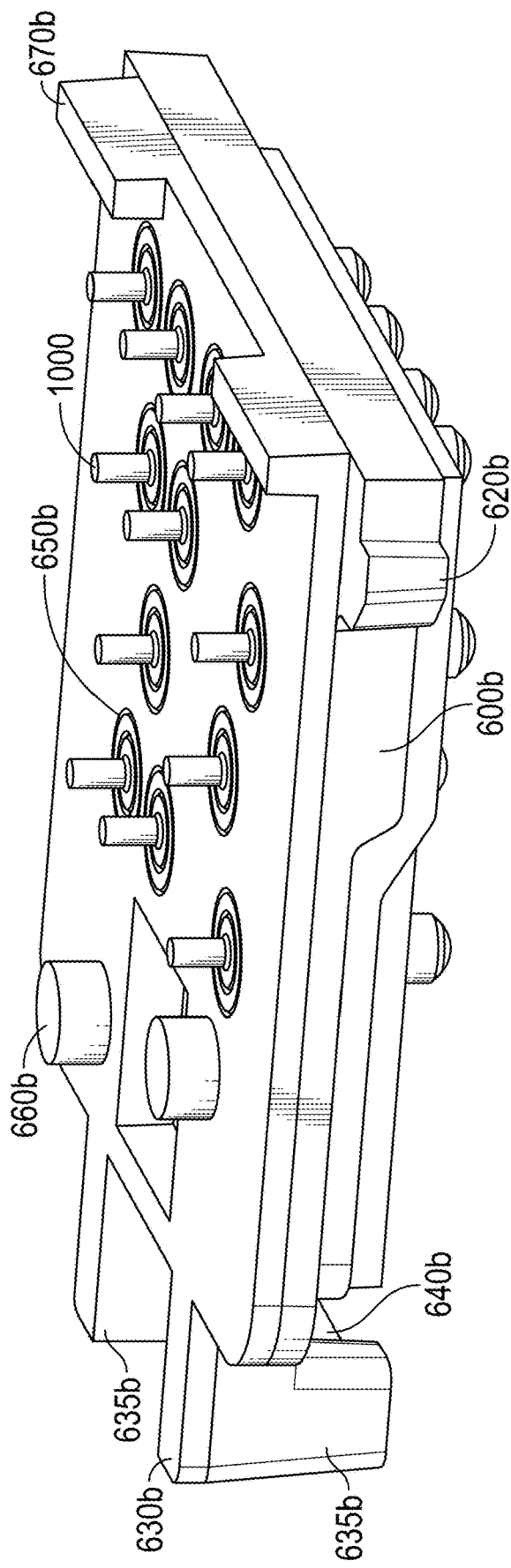
FIG. 6B illustrates a perspective view of another embodiment of the inner shield with pogo pins disposed within each of the pogo pin holes.
Figure 6C:
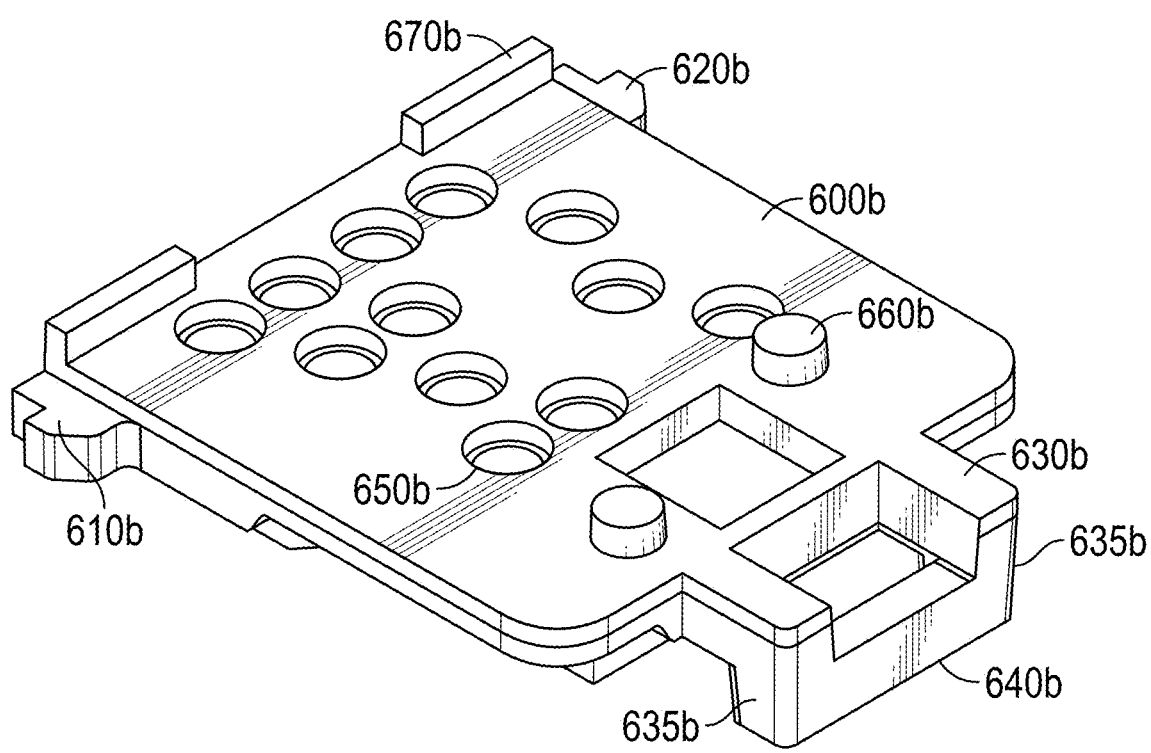
FIG. 6C illustrates a perspective view of the embodiment of the inner shield of FIG. 6B with the pogo pins removed.
Figure 7B:
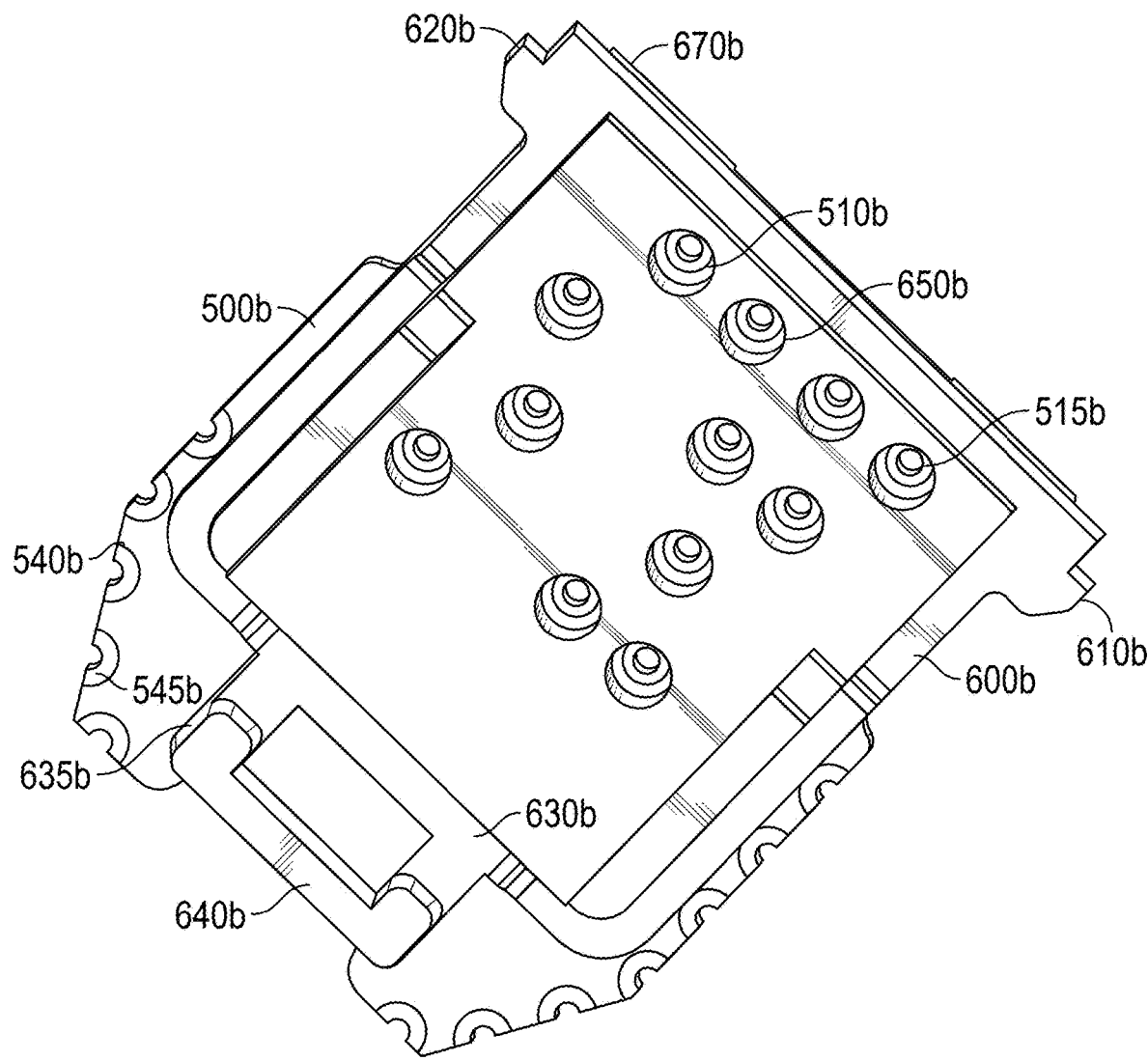
FIG. 7B illustrates a bottom view of another embodiment of the connector of FIGS. 5B & 6B with the pogo pins removed.
Figure 8C:
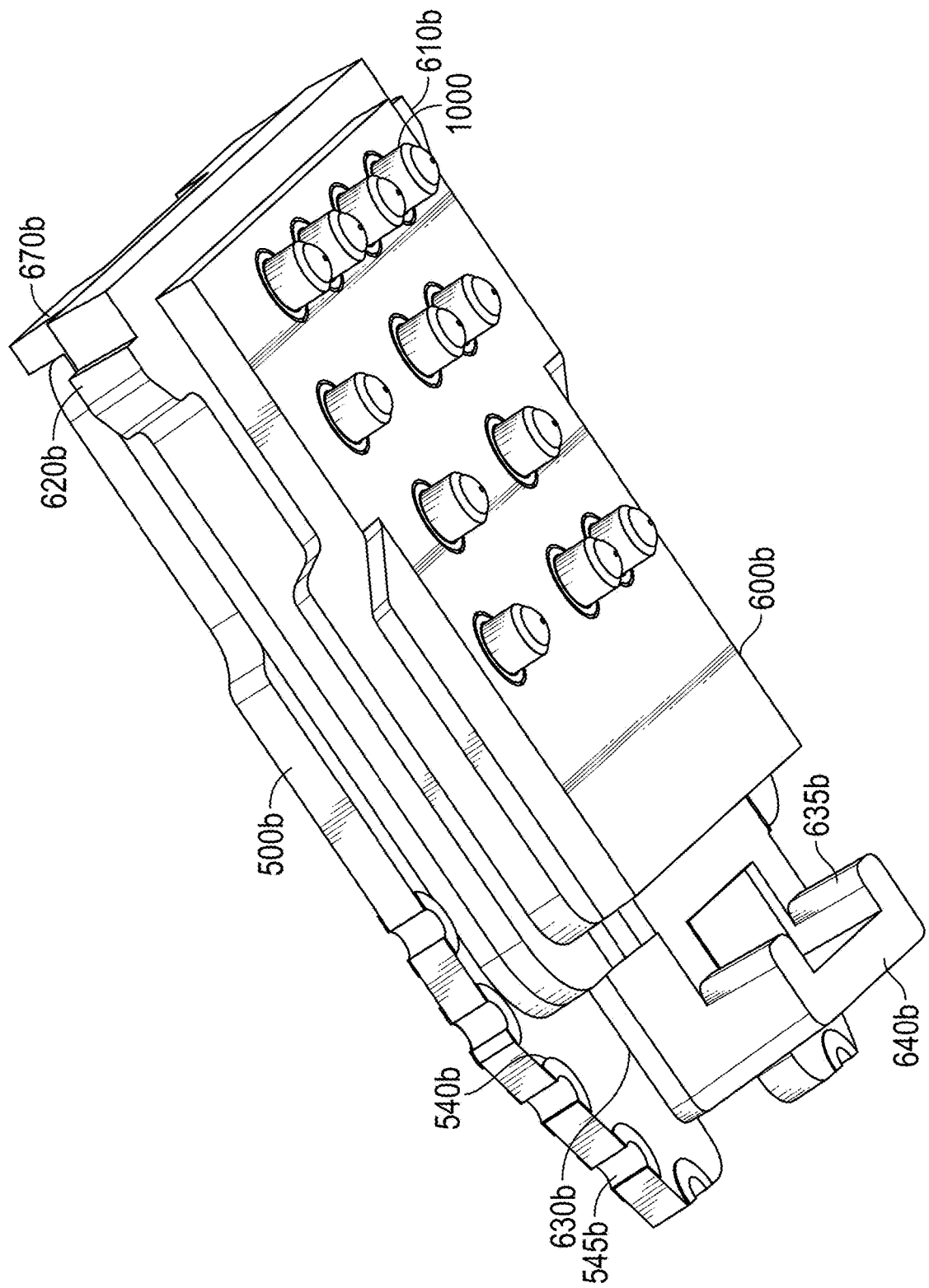
FIGS. 8C-8D illustrate a bottom perspective view of another embodiment of the connector of FIGS. 4C-4D with the inner shield removed.
Figure 8D:
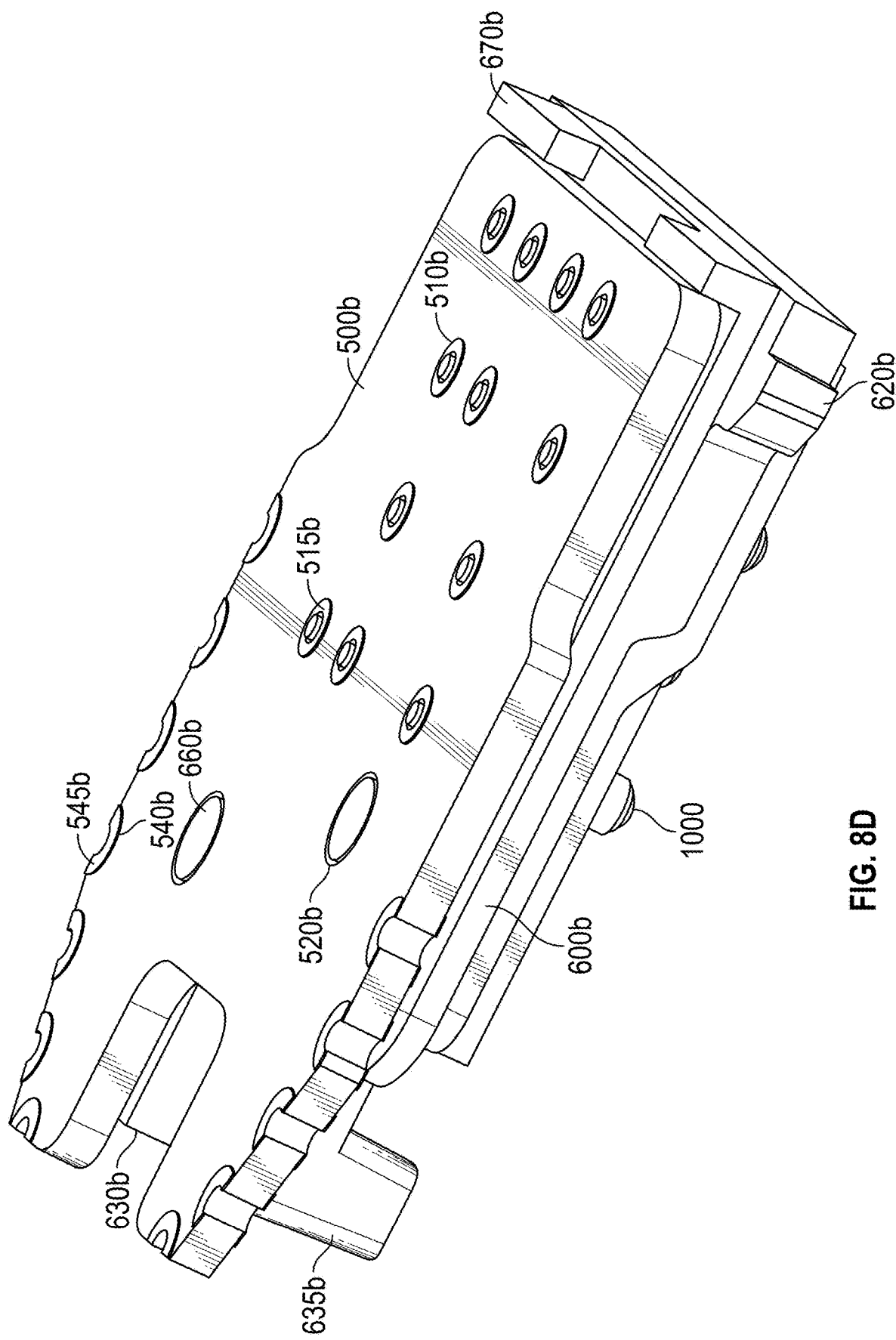

FIGS. 5B, 6B-6C, 7B, and 8C-8D provide various views of alternative embodiments of the printed circuit board 500*b* and inner shield 600*b* with and without the pogo pins 1000 inserted through the printed circuit board 500*b* and inner shield 600*b*. FIG. 5B shows a bottom perspective view of the printed circuit board 500*b*. FIG. 6B shows a perspective view of the inner shield 600*b* with a plurality of pogo pins 1000 located through the holes of the printed circuit board 500*b*. FIG. 6C illustrates another perspective view of the inner shield 600*b* with the pogo pins 1000 removed. FIG. 7B shows a bottom view of the interconnected printed circuit board 500*b* and inner shield 600*b* without the pogo pins 1000. Finally, FIGS. 8C-8D illustrate a top and bottom perspective view of the interconnected printed circuit board 500*b* and inner shield 600*b* with a plurality of pogo pins 1000 inserted in the aligned holes of the printed circuit board 500*b* and inner shield 600*b*.

The printed circuit board 500*b* is similar to the printed circuit board 500 described above in FIG. 5. Like the printed circuit board 500, the printed circuit board 500*b* can include a plurality of small holes 510*b*, large holes 520*b*, and outer holes 540*b*. Like the printed circuit board 500, the printed circuit board 500*b* can include small holes 510*b* that can accommodate the plurality of pogo pins 1000. As well, like the large holes 520 of the printed circuit board 500, the large holes 520*b* can accommodate the plurality of connector pins 660*b* of the inner shield 600*b*. As noted above, in some embodiments, the plurality of connector pins 660*b* can retain the printed circuit board 500*b* to the inner shield 600*b*. As seen in FIG. 5B, the small holes 510 can be located on the printed circuit board 500*b* in a staggered configuration. Each of the small holes 510*b* can be disposed about a pogo pin 1000 and allow for a portion of the pogo pin 1000 to protrude through the printed circuit board 500*b*. In some embodiments, electrical contacts 515*b* can be located on the inside surface of each of the small holes 510*b*. Finally, in some embodiments, the printed circuit board 500*b* can include a plurality of outer holes 540*b* located near the border of the printed circuit board 500*b*. In some embodiments, each of the outer holes 540*b* can include electrical contacts 545*b* on the inside surface of the outer holes 540*b*. In some examples, the electrical contacts 545*b* can provide an electrical connection between the printed circuit board 500*b* and the attached cable.

FIG. 6B illustrates another embodiment of the inner shield. FIG. 6B illustrates an inner shield 600*b* with a plurality of pogo pins 1000 located inner shield 600*b*. In some embodiments, the inner shield 600*b* can include a plurality of structures that ensures the proper positioning of the inner shield 600*b* in the connector 200*b*. As discussed above, the inner shield 600*b* can include a plurality of structures to interact with sensor assembly receiver 400*c* and the printed circuit board 500*b* such that the inner shield 600*b* is retained in a proper configuration on the sensor assembly receiver 400*c* and in the connector 200.

The inner shield 600*b* can also include a number of structures so as to retain and properly position the printed circuit board 500*b* on the surface of the printed circuit board 500*b*. As shown in FIG. 6C, the inner shield 600*b* can have a plurality of connector pins 660*b* and a proximal shelf 670*b*. As discussed above the plurality of connector pins 660*b* can align with the plurality of large holes 520*b* of the printed circuit board 500*b* such that the large holes 520*b* are configured to be disposed about the connector pins 660*b*. The inner shield 600*b* can also include a plurality of pogo pin holes 650*b*. The plurality pogo pin holes 650*b* can be located in a staggered configuration such that each of the plurality of the pogo pin holes 650*b* can be aligned to correspond with the small holes 510*b* of the printed circuit board 500*b*. The connector pin 660*b* of the inner shield 600*b* can interact with the large holes 520*b* to maintain the passageway created by the small holes 510*b* and pogo pin holes 650*b*.

This connection can be further seen in FIG. 7B. FIG. 7B shows a bottom view of the inner shield 600*b* with the printed circuit board 500*b* aligned over it. The pogo pin holes 650*b* of the inner shield 600*b* can be larger in diameter than the small holes 510*b* of the printed circuit board 500*b*. In the embodiment shown in FIG. 7B, each of the small holes 510*b* can be coaxially aligned with each of the pogo pin holes 650*b* so as to allow a pogo pin 1000 to be retained and move within the passage (e.g. channel, pathway) created by the pogo pin hole 650*b* and small hole 510*b*.

As can be seen in FIGS. 8C-8D, as was illustrated above in FIGS. 8A-8B, the pogo pin holes 650*b* can be configured such that the plurality of pogo pins 1000 are positioned in the pogo pin holes 650*b* such that both ends of each of the pogo pins 1000 can protrude from the inner shield 600*b*. The distal end 1110 of the pogo pins 1000 contacts the printed circuit board 500*b* and allows for an electrical connection to be formed between the electrical contacts 545*b* of the printed circuit board 500*b* and the pogo pins 1000. As will be further discussed below, the small holes 510*b* of the printed circuit board 500*b* and the internal structure of each of the pogo pin holes 650*b* can help to retain each of the pogo pins 1000 to prevent it from moving out of the pogo pin holes 650*b* of the inner shield 600*b*. Also, as will be discussed below, the pogo pins 1000 are retained in a staggered configuration that can accommodate sensors with a range of electrical contacts. This staggered configuration can help to reduce the profile of the connector 200 and allow the same connector 200 structure to be used in a large number of sensors. This is partly because the staggered configuration allows more separate connection points than would otherwise fit in the same space without a staggered configuration.

Each connector 200 contains a plurality of pogo pins 1000 that help to establish the electrical connection between the electrical contacts of the sensor assembly 800*a* and the connector 200 as seen in the complete assembly 100 of FIG. 1. Pogo pins can be made in a variety of shapes and sizes and usually take the form of a slender cylinder containing two spring loaded pins.

Figure 9A:
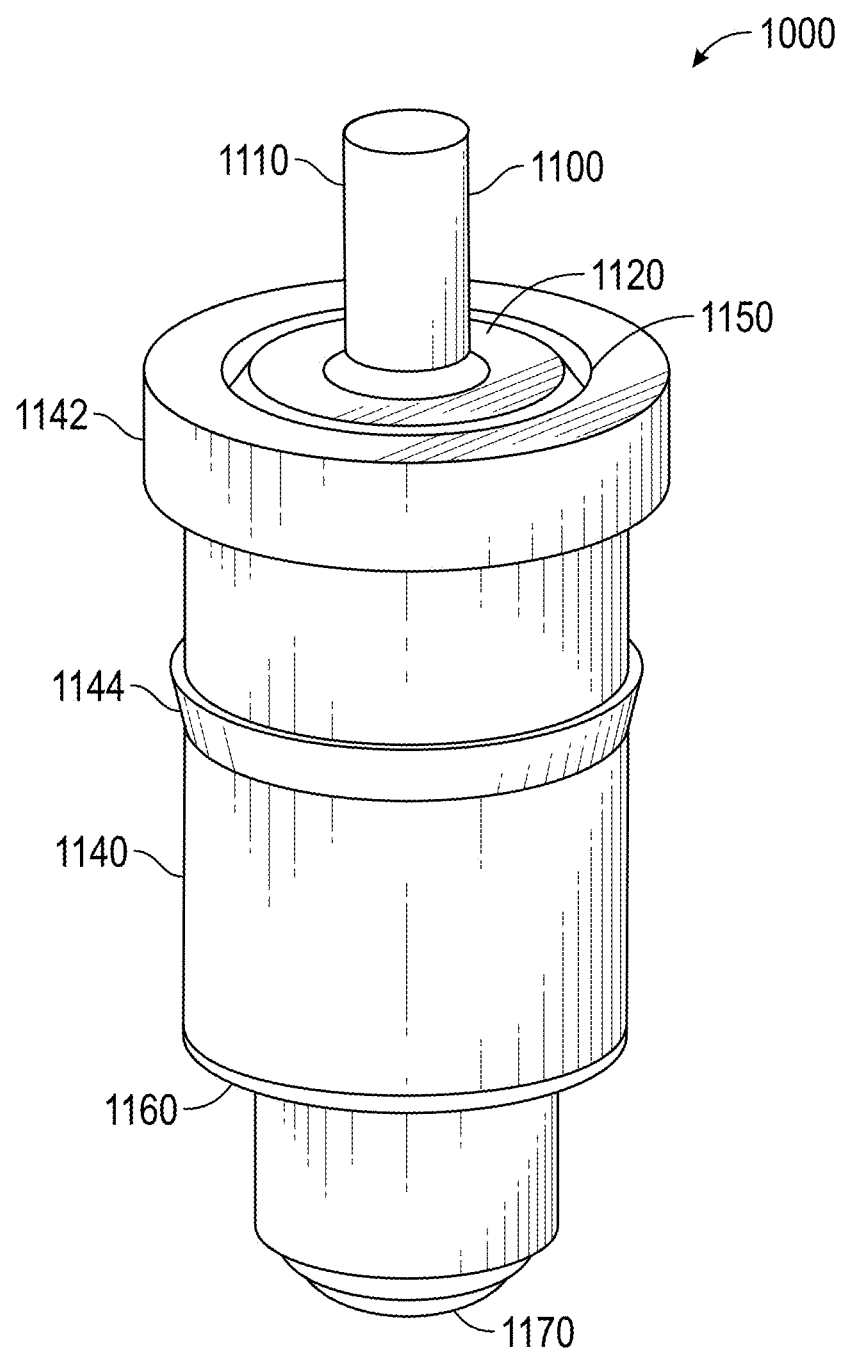
FIGS. 9A-9C illustrate perspective and cross-sectional views of one embodiment of a pogo pin.
Figure 9B:
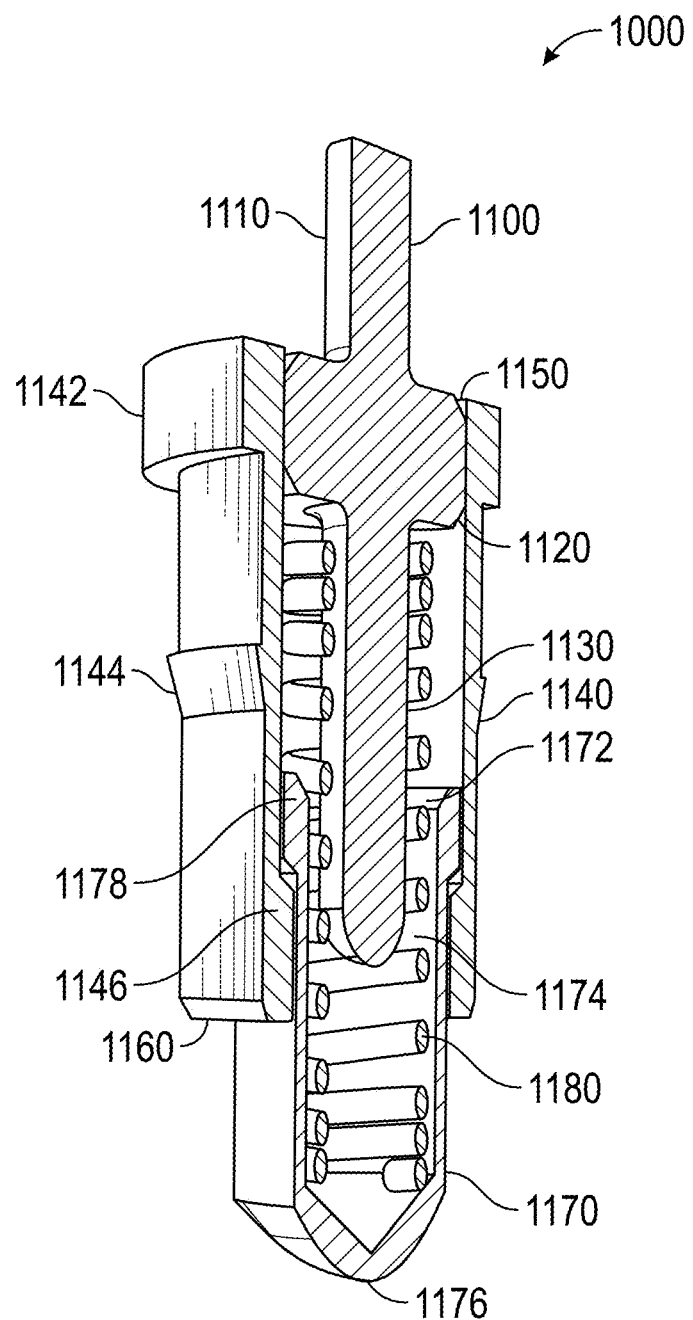
Figure 9C:
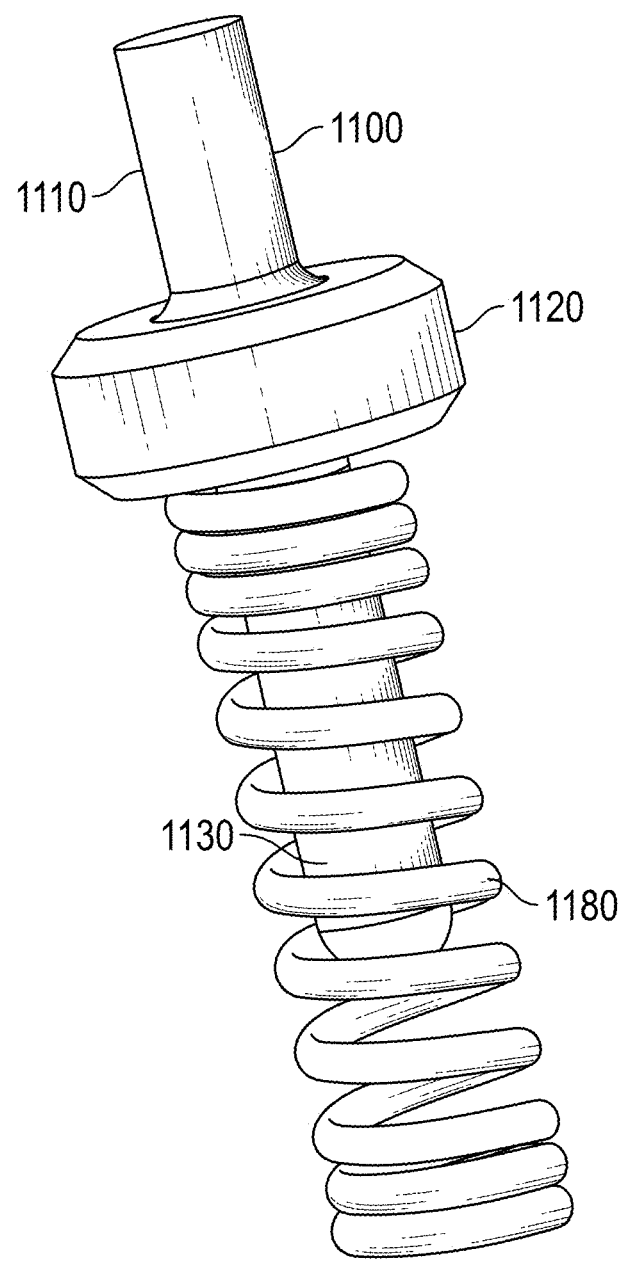
Figure 9D:
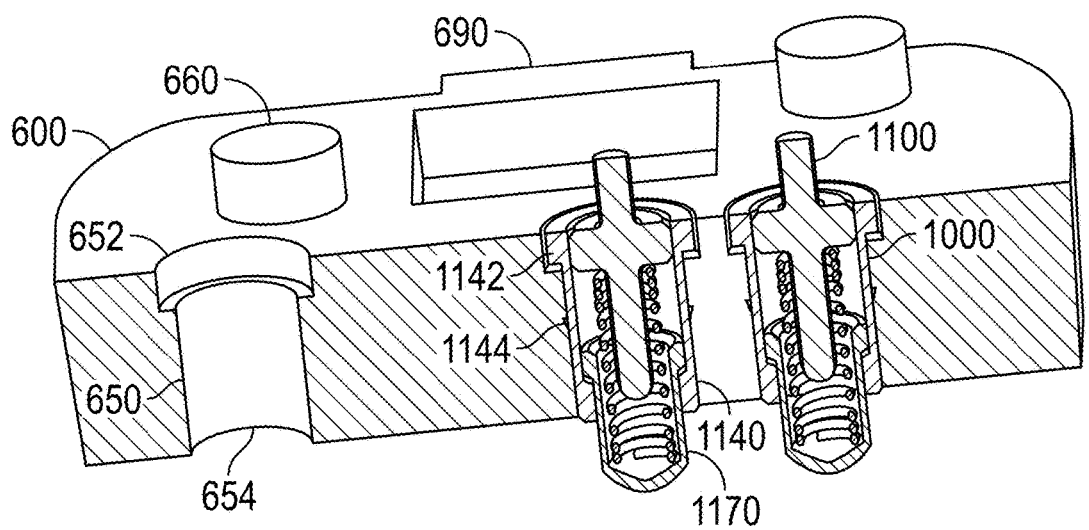
FIGS. 9D-9E illustrate cross-sectional views of one embodiment of a plurality of pogo pins retained between the inner shield and the printed circuit board.
Figure 9E:
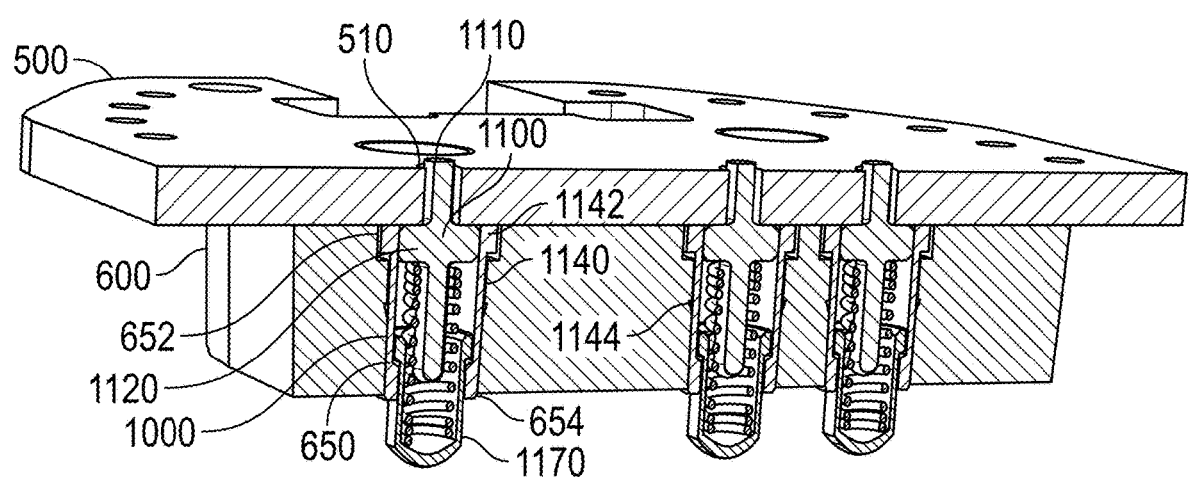

FIG. 9A-9C illustrate multiple views of some embodiments of a pogo pin 1000. FIG. 9A shows a perspective view of a pogo pin 1000, FIG. 9B shows a cross section of the pogo pin 1000, and FIG. 9C shows the inside components of the pogo pins 1000. FIG. 9D-9E illustrate two figures showing the pogo pins 1000 retained between the printed circuit board 500 and inner shield 600. FIG. 9D provides a cross-sectional example of the inner shield 600 with a plurality of pogo pins 1000 disposed within the pogo pin holes 650 of the inner shield 600. FIG. 9E provides a cross-sectional example of a plurality of pogo pins 1000 contained between the printed circuit board 500 and inner shield 600.

As can be seen in FIGS. 9A-9C, in one embodiment the pogo pin 1000 can include four structures—a plunger 1100, a hollow barrel 1140, a spring 1180, and a contact tip 1170. The hollow barrel 1140 houses the plunger 1100, spring 1180, and contact tip 1170. Further, the hollow barrel 1140 disposed about the spring 1180. The pogo pins 1000 can be made of a conductive material and are configured such that the spring 1180 can push against both the plunger 1100 and the contact tip 1170 to move both parts such that an electrical connection is established through the pogo pin 1000.

The hollow barrel 1140 has a distal opening 1150 and proximal opening 1160 to allow the plunger 1100 and contact tip 1170 to protrude from the hollow barrel 1140 respectively. As can be seen in FIG. 9A-9B, the hollow barrel 1140 includes a distal edge 1142 and a proximal edge 1144 that helps to contain the pogo pins 1000 in the interior structure of the pogo pin holes 650 of the inner shield 600. As will be discussed further below, the interior structure of the pogo pin holes 650 along with the location of the small holes 510 of the printed circuit board 500 retain the pogo pins 1000 between the printed circuit board 500 and inner shield 600. The hollow barrel 1140 can also include an inner lip 1146 on the inside surface of the hollow barrel 1140 near the proximal opening 1160. As will be discussed in more detail, the inner lip 1146 can interact with the outer surface of the distal end of the contact tip 1170 to prevent the contact tip 1170 from exiting out from the proximal opening 1160 of the hollow barrel 1140.

The plunger 1100 includes a distal end 1110, stopper 1120, and cylindrical proximal end 1130. As is seen in FIGS. 9B and 9C, the cylindrical proximal end 1130 is disposed within the coils of the spring 1180. The stopper 1120 is located distal to the cylindrical proximal end 1130 and has a cylindrical structure with a diameter that can be greater than the diameter of the coils of the spring 1180 but smaller than the diameter of the inside surface of the hollow barrel 1140. The diameter of the stopper 1120 allows the spring 1180 to collapse against the surface of the stopper 1120. The distal end 1110 of the plunger 1100 can have a cylindrical shape that has a diameter less than or equal to the diameter of the inside surface of the hollow barrel 1140. In one embodiment, the diameter and length of each of the distal ends 1110 of the pogo pins 1000 is configured to be coaxially disposed within one of the small holes 510 of the printed circuit board 500. In some embodiments, distal end 1110 is configured to engage with an electrical contact within the connector 200.

The spring 1180 can be disposed coaxially within the hollow barrel 1140 and assists in the driving of the plunger 1100 and the contact tip 1170. The spring 1180 can be made of a conductive material which allows the spring 1180 to connect the sensor with the electrical contacts on the printed circuit board 500. As seen in FIG. 9B, the spring 1180 is partially disposed within the hollow barrel 1140 and can extend past the proximal opening 1160 of the hollow barrel 1140. As discussed earlier, the cylindrical proximal end 1130 of the plunger 1100 is coaxially disposed within the coils of the spring 1180. The stopper 1120 of the plunger 1100 maintains the distal most position of the distal end of the spring 1180. A proximal portion of the spring 1180 extends out from the proximal opening 1160 of the hollow barrel 1140 and is coaxially disposed within the hollow center 1174 of the contact tip 1170. As will be discussed in more detail, the contact tip 1170 can interact with the spring 1180 (e.g. compressing, shortening, extending, lengthening) as the contact tip 1170 moves axially along the inside surface of the hollow barrel 1140.

The contact tip 1170 can protrude from the proximal opening 1160 of the hollow barrel 1140. The contact tip 1170 has a distal end opening 1172, a hollow center 1174 with an internal surface, a proximal end 1176, and a distal lip 1178 on the outer surface of the distal end of the contact tip 1170. The contact tip 1170 can be made of a conductive material. The distal end opening 1172 of the contact tip 1170 allows the spring 1180 to extend coaxially into the hollow center 1174 of the contact tip 1170. As discussed above, the hollow center 1174 of the contact tip 1170 is disposed about the proximal end of the spring 1180 and movement of the contact tip 1170 within the hollow barrel 1140 causes the interaction of the inside surface of the contact tip 1170 with the proximal end of the spring 1180. This interaction causes the spring 1180 to either compress (e.g. shorten) or extend (e.g. lengthen). The proximal end 1176 of the contact tip 1170 can be configured such that it can interact with the electrical contact of the sensor assembly 800a. In some configurations, the proximal end 1176 can be tapered to provide a consistent connection with the electrical contact of the sensor assembly 800a. In other configurations, the proximal end 1176 has a rounded end in order to prevent damaging the surface of the electrical contact on the sensor assembly 800a. Finally, the distal lip 1178 can have a structure that retains the contact tip 1170 within the hollow barrel 1140. As seen in FIG. 9B, the distal lip 1178 of the distal end of the contact tip 1170 interacts with the inner distal lip 1178 of the hollow barrel 1140 such that a distal portion of the contact tip 1170 is retained in the hollow barrel 1140. In one embodiment, the diameter of the inner surface of the hollow barrel 1140 at the inner lip 1146 is configured to be narrower than the diameter of the distal lip 1178 but wide enough to allow the body of the contact tip 1170 to fit through. In this configuration, the interaction between the distal lip 1178 of the contact tip 1170 and the inner lip 1146 of the hollow barrel 1140 prevent the contact tip 1170 from fully exiting from the proximal opening 1160 of the hollow barrel 1140.

FIGS. 9D-9E illustrate how the pogo pins 1000 are retained between the printed circuit board 500 and inner shield 600. As can be seen in FIG. 9D, each of the pogo pin holes 650 of the inner shield 600 has a distal opening 652 and a proximal opening 654. The diameter of the distal opening 652 is wider than the diameter of the proximal opening 654 and the pogo pin holes 650 is configured to retain the hollow barrel 1140 of the pogo pin 1000. In one configuration, the distal opening 652 is configured to retain the distal edge 1142 of the hollow barrel 1140 and the proximal opening 654 is configured to retain the proximal body portion of the hollow barrel 1140. This configuration retains the pogo pin 1000 in the inner shield 600. To prevent the pogo pins 1000 from moving out of the inner shield 600 in a distal direction, the printed circuit board 500 is placed over inner shield 600. The small holes 510 of the printed circuit board 500 are configured to retain the distal end 1110 of the plunger 1100. This can serve a multitude of purposes. For example, because the small holes 510 have a diameter that accommodates the distal end 1110 but is not wide enough to accommodate the stopper 1120 of the plunger 1100, this retains the components of the pogo pins 1000 that are contained within the hollow barrel 1140. As well, the small holes 510 are configured to allow the plunger 1100 to come in contact with the electrical contacts on the printed circuit board 500.

In operation, the position of both the printed circuit board 500 and the inner shield 600 allow the establishment of a secure electric connection between the electrical contact on the printed circuit board 500 and the electrical contact on the sensor assembly 800a. As will be discussed in further detail below, as the sensor assembly 800a is positioned in the connector 200, the profile of the sensor assembly 800a pushes the contact tip 1170 in a distal direction such that the contact tip 1170 further retracts into the hollow barrel 1140. This movement causes the proximal end of the hollow center 1174 of the contact tip 1170 to compress the spring 1180.

This compression force can then, in turn, force the stopper 1120 in a distal direction that brings the distal end 1110 of the plunger 1100 in contact with the electrical contacts on the printed circuit board 500. As the pogo pins 1000 are made of a conductive material, this ensures that an electrical connection is established between the electrical contacts on the printed circuit board 500 of the connector 200 and the electrical contact on the sensor assembly.

The connector and sensor of the complete assembly 100 are designed such that the same general assembly of the connector and sensor could be used for a number of different types of sensors. As discussed previously, the configuration of the plurality of pogo pins 1000 in the connector 200 allows the connector 200 to be adapted to accommodate a sensor with a wide range of electrical contacts. This design provides a manufacturing benefit as the general design of the complete assembly 100 does not need to be redesigned to accommodate every individual sensor. Instead, the configuration of the small holes 510 and pogo pin holes 650 of the printed circuit board 500 and inner shield 600 can vary depending on the location of the electrical contacts on the sensor.

Because the same complete assembly 100 can be used for a number of different sensors, to assist a patient and/or medical practitioner in connecting the correct sensor with the correct connector, the connector and sensor of the complete assembly 100 can be configured with a number of helpful structures and/or characteristics. FIGS. 10A-10D and FIGS. 11A-11E illustrate two examples of corresponding connectors and sensors respectively that are configured to assist a user with properly connecting the correct connector to the correct sensor. FIGS. 10A-10D illustrate two examples of connectors that are configured to only accept the proper sensor assembly. Similarly, FIGS. 11A-11E illustrate two examples of corresponding sensor assemblies that are configured to only connect with the proper connector.

Figure 10A:
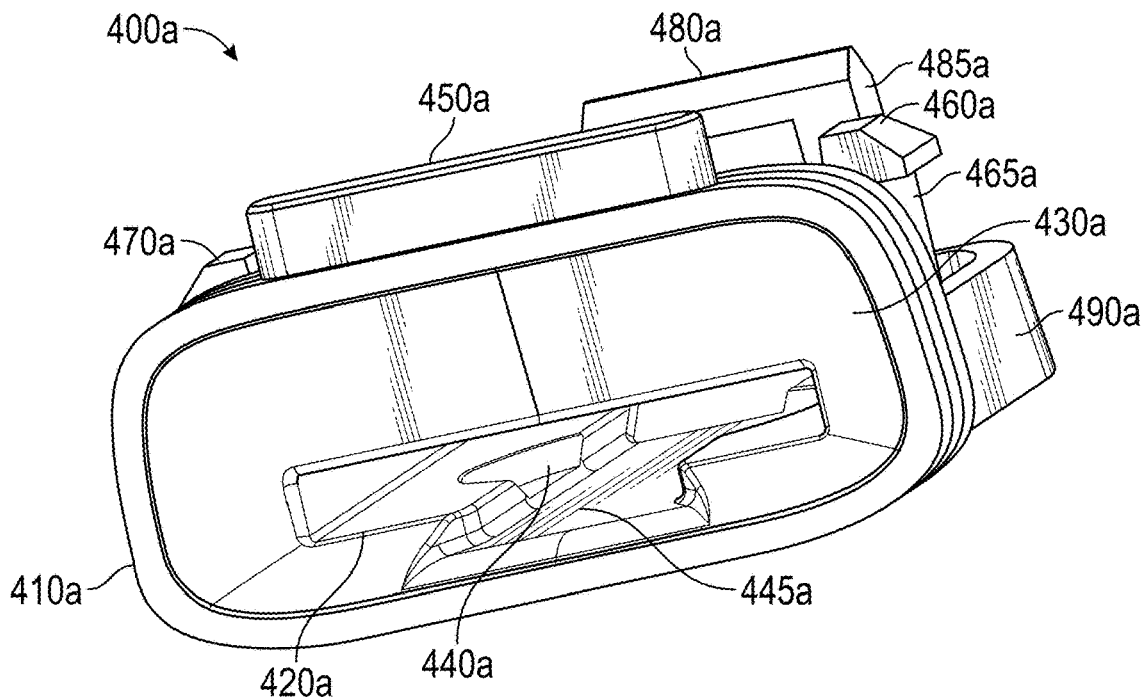
FIGS. 10A-10K illustrate various views of five embodiments of sensor assembly receivers.
Figure 10B:
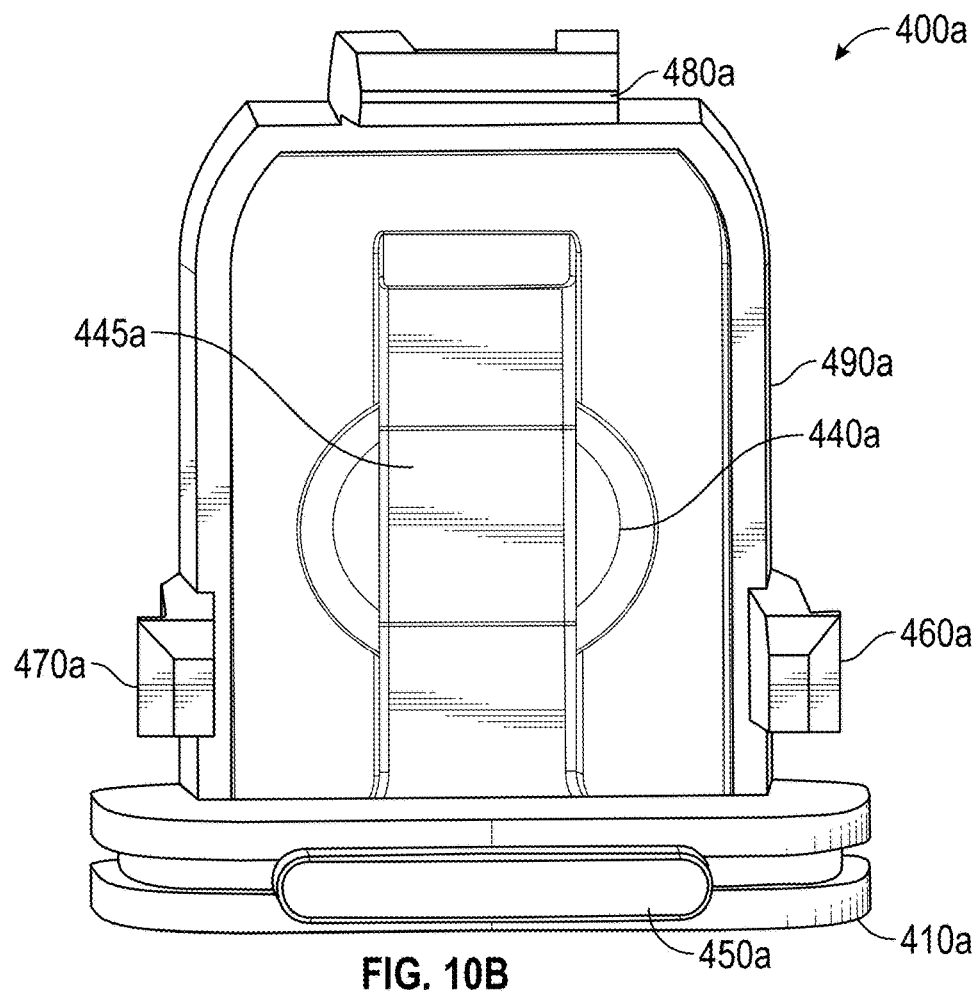

FIGS. 10A-10B show a front and top view of the sensor assembly receiver 400a. As described above, the sensor assembly receiver (here the sensor assembly receiver 400a) has a body 490a to accommodate the male connector portion of the sensor assembly. As discussed above, the sensor assembly receiver 400a also has a plurality of arms—the first arm 465a, second arm 475a, and distal arm 485a—that help to retain the printed circuit board 500 and inner shield 600 as discussed above. The body 490a has a proximal end 410a with a tapered surface 430a that leads to the opening 420a of the body 490a. As discussed earlier, the tapered surface can help to guide the sensor into the opening 420a of the body 490a. The body 490a can include a receptor 445a that accommodates a key on the sensor. This is further shown in FIG. 10B, wherein the body 490a can only accommodate a sensor with a key in the shape of the receptor 445a. Further, the body 490a can also include a detent 440a that can interact with a similarly shaped detent on the sensor. As discussed below, the detent 440a and the detent located on the underside of the sensor can provide mechanical feedback to the user.

Figure 11A:
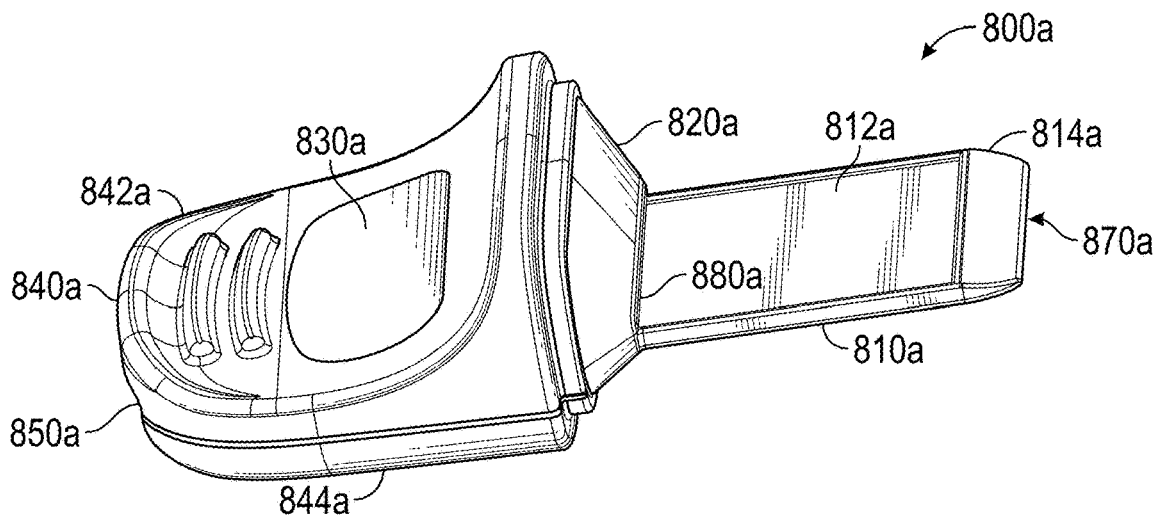
FIGS. 11A-11H illustrate various views of five embodiments of sensor assemblies.
Figure 11B:
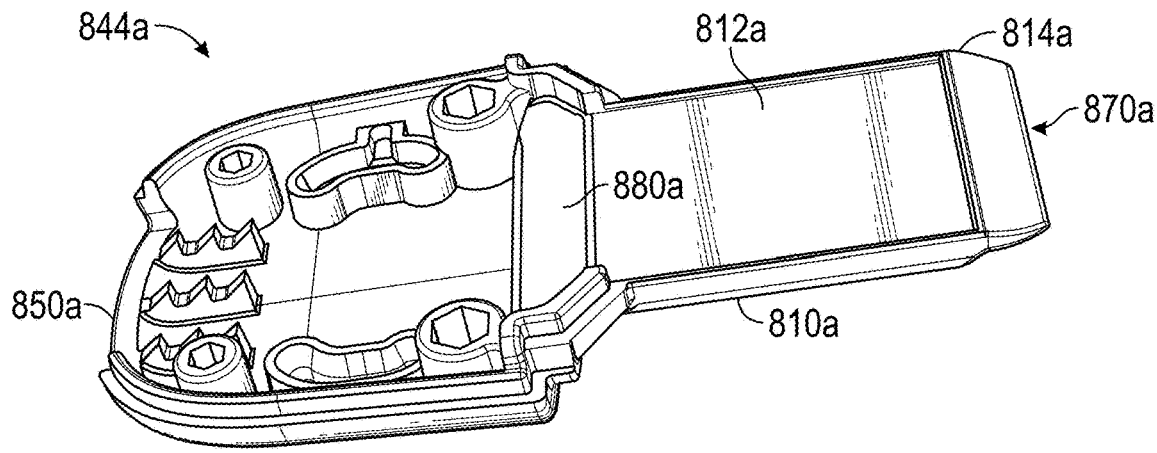
Figure 11C:
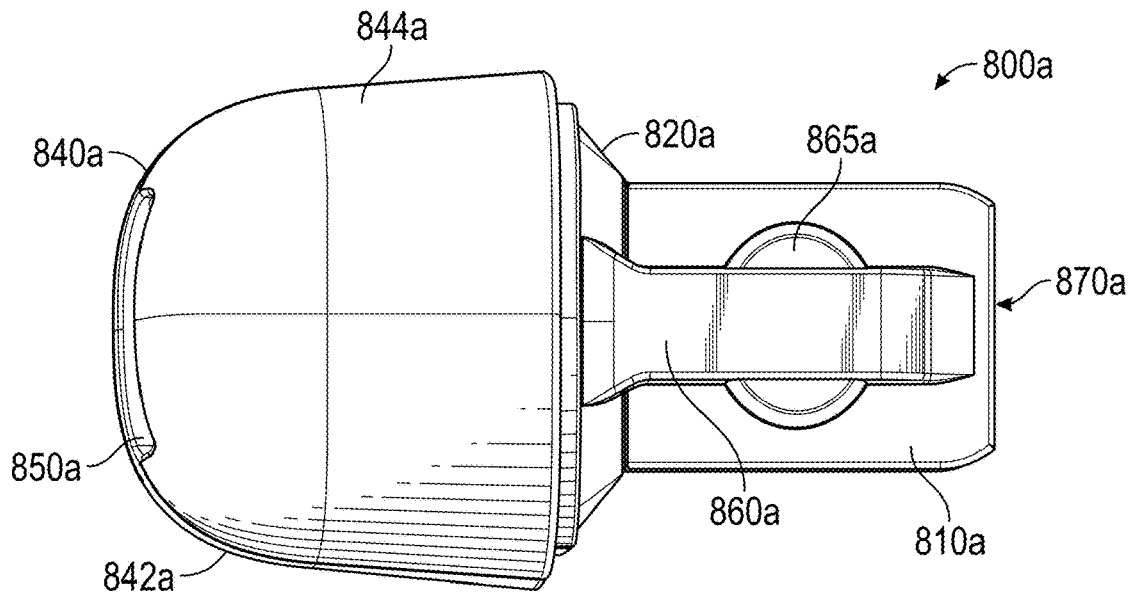

FIGS. 11A-11C shows a front and bottom view of the sensor assembly 800a that is configured to fit into the body 490a of the sensor assembly receiver 400a. The sensor assembly 800a has a connector assembly 840a that can accommodate a sensor. As can be seen in FIGS. 11A-11B, the connector assembly 840a includes a top connector assembly 842a and a bottom connector assembly 844a. The top connector assembly 842a can connect with the distal portion of the bottom connector assembly 844a. As the top connector assembly 842a and bottom connector assembly 844a are connected, the distal end 850a and the opening 880a can accommodate a sensor between the two parts of the connector assembly 840a. The proximal end of the top connector assembly 842a has a tapered surface 820a that is configured to fit against the tapered surface 430a of the sensor assembly receiver 400b. The top connector assembly 842a can accommodate a label 830a. As will be discussed further below, the label 830a can vary so as to indicate the type of sensor accommodated by the sensor assembly 800a. As can be seen in FIGS. 11A-11C, the proximal end 870a of the bottom connector assembly 844a includes a sensor tab 810a that has a sensor side 812a, lip 814a, and a key 860a and a key detent 865a on the bottom of the sensor side 812a. The sensor side 812a has an opening that accommodates for the sensor and the lip 814a on the proximal end of the sensor tab 810a ensures the placement of the sensor on the sensor side 812a. On the reverse side of the sensor tab 810a is a key 860a. As will be discussed in further detail, the key 860a is configured to fit the detent 440a of the sensor assembly receiver 400a discussed above. As well, as will be discussed in further detail below, the key 860a is configured to engage with the receptor 445a of the sensor assembly receiver 400a.

In operation, as discussed earlier, the sensor assembly 800a can have a number of configurations to facilitate the connection between the sensor assembly 800a and the sensor assembly receiver 400a. Further, the sensor assembly 800a and sensor assembly receiver 400a can have a number of other configurations to ensure that the correct sensor assembly 800a is connected to the proper sensor assembly receiver 400a. As discussed above, the tapered surface 820a corresponds with the tapered surface 430a of the sensor assembly receiver 400a and can help to guide the sensor tab 810a into the opening 420a of the body 490a. As discussed above, each sensor assembly has a key that corresponds with the detent of the corresponding sensory assembly receiver of the connector 200. Here, the key 860a from FIG. 11C is configured to fit the receptor 445a of the sensor assembly receiver 400a. As can be seen in FIGS. 10B and 11C, the shape of the receptor 445a is shaped to receive the key 860a of the sensor assembly 800a. The location of the key 860a and the receptor 445a also ensure that the sensor assembly 800a is inserted into the sensor assembly receiver 400a with the sensor side 812a up. Further, as discussed above, the underside of the sensor tab 810a includes a key detent 865a that can be engaged with the detent 440a located on the bottom surface of the sensor assembly receiver 400a. Once inserted, the sensor tab 810a and the detent 440a can engage to provide mechanical feedback to the user. As will be discussed in further detail below, the sensor has a number of electrical contacts that will interact with the pogo pins 1000 shown in previous figures. This connection will ensure that an electrical connection is created between the connector 200 and the sensor assembly.

Finally, in some embodiments, the sensor assembly receiver 400a can have the same color as the label 830a of the sensor assembly 800a. For example, the sensor assembly receiver 400a and the label 830a of the sensor assembly 800a can both have a red color, a blue color, a black color, or a gray color. In this embodiment, when the sensor assembly receiver 400a is assembled inside the connector 200, the colored top tab 450a and the colored tapered surface 430a are visible from the outer jacket 210 of the connector 200. The matching colors of the visible portions of the sensor assembly receiver 400a and the label 830a allow the user to identify visually whether the correct connector 200 is attached to the correct sensor assembly. In some embodiments, the sensor assembly receiver 400a can have a color indicator on the tapered surface 430a and the top tab 450a. In some examples, this provides the user with a visual indicator as to what sensor assembly can be properly inserted into the connector. Because the tapered surface 430a of the sensor assembly receiver 400a is no longer visible once the sensor assembly 800a is inserted, in some embodiments, the top tab 450a can serve as a visual indicator to the user regarding the type of sensor the complete assembly 100 includes.

Figure 10C:
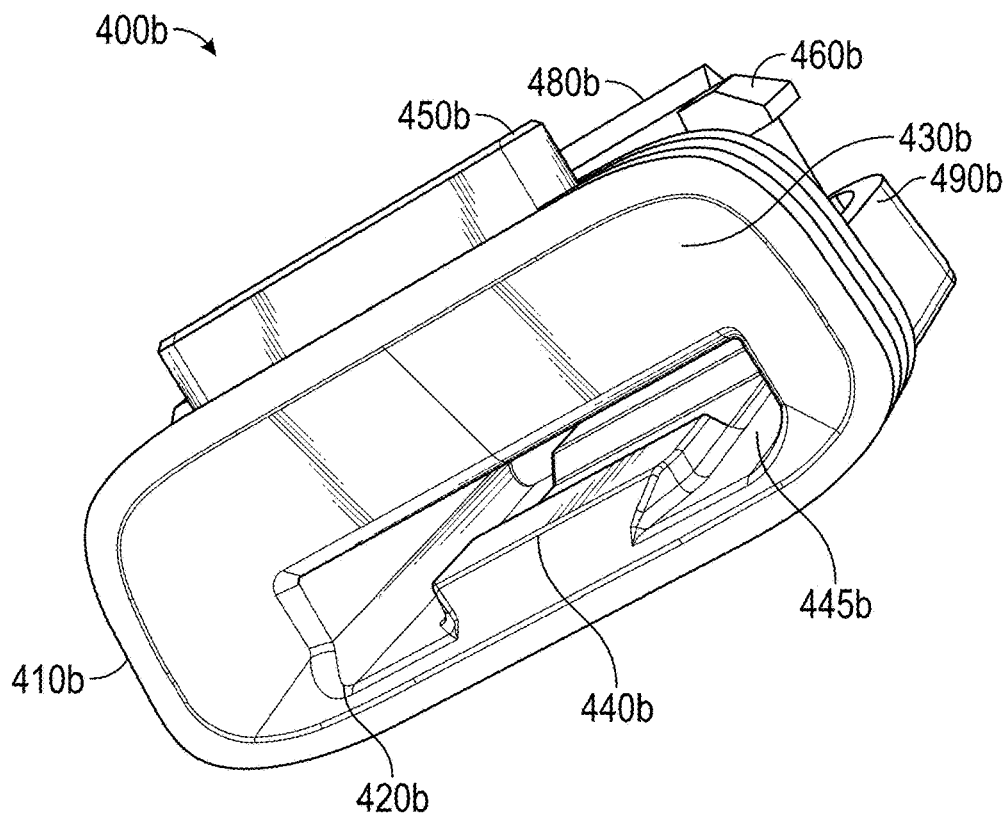
Figure 10D:
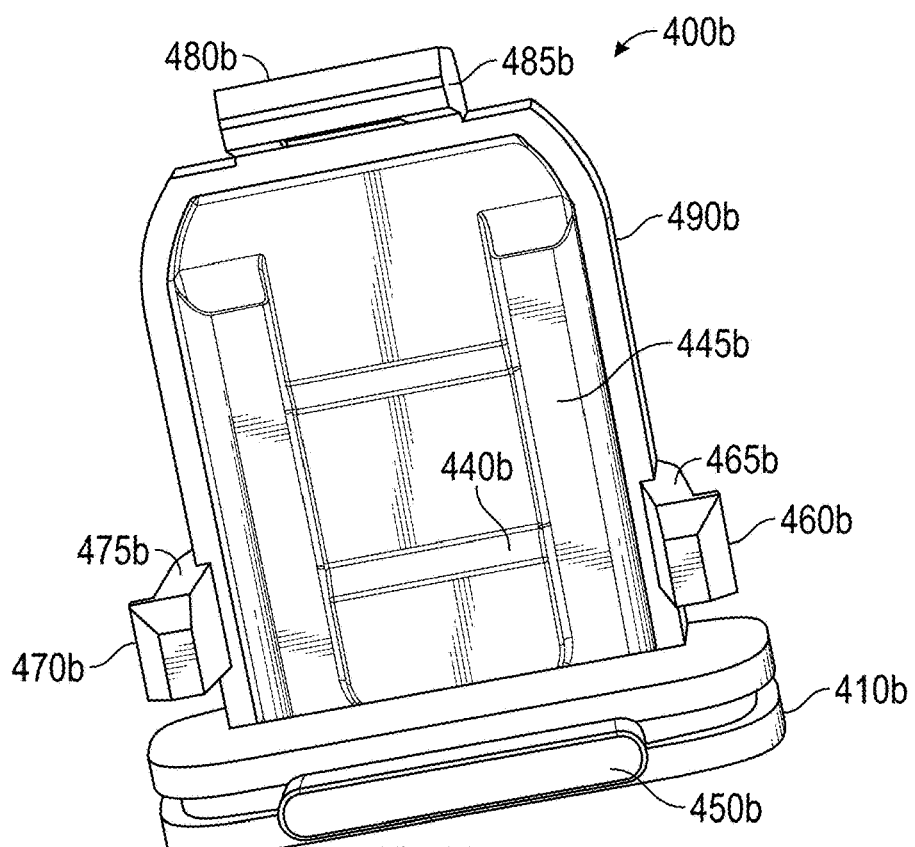
Figure 11D:
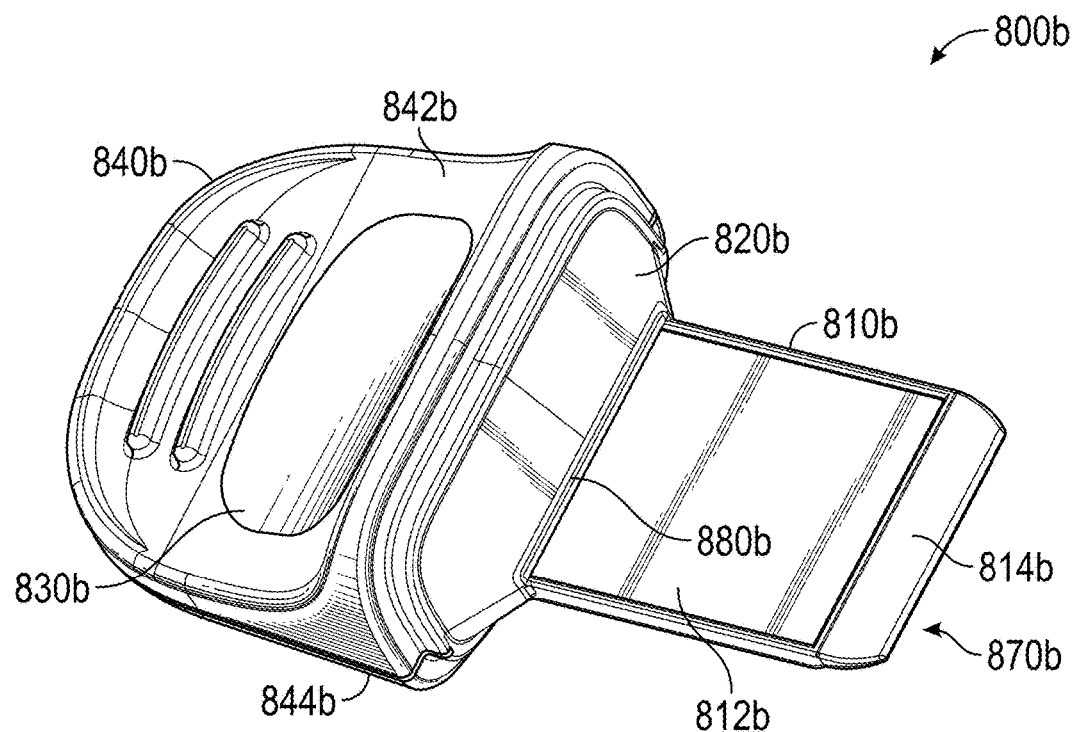
Figure 11E:
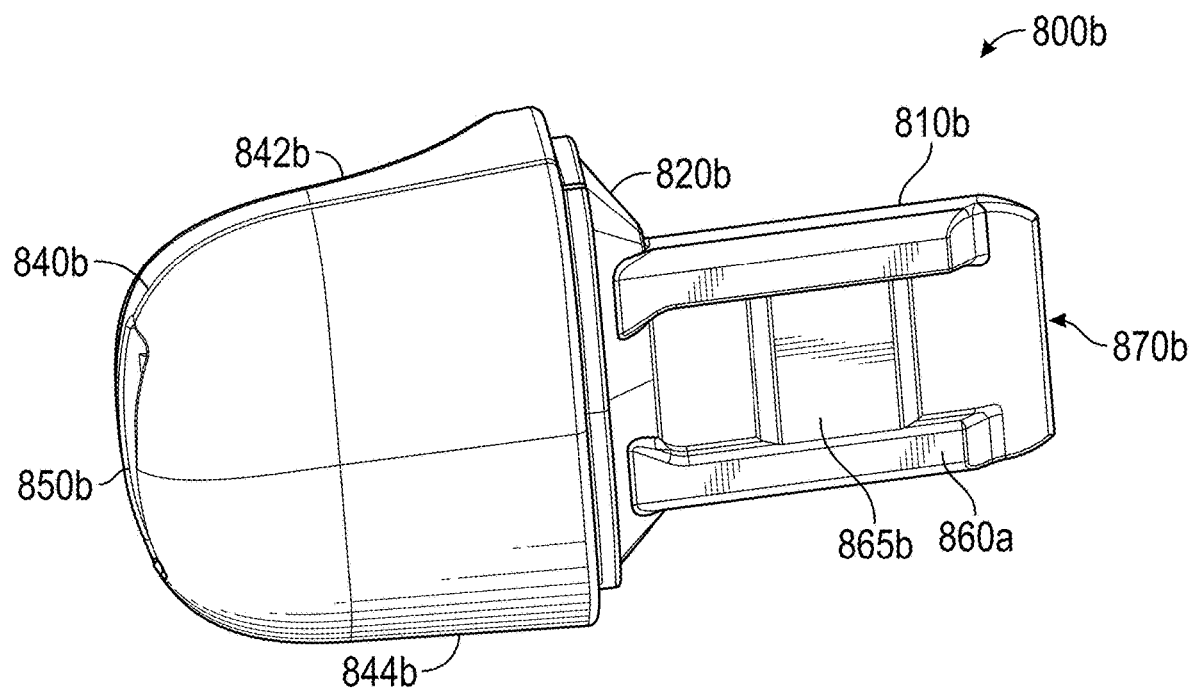

In order to prevent improper connections between different connectors and sensor assemblies, different connectors can have different detents. The corresponding sensor assemblies, in turn, will have keys that correspond with the connecting detent. FIGS. 10C-10D and FIGS. 11D-11E illustrate another example complete assembly 100 where the sensor assembly receiver 400b and sensor assembly 800b have corresponding receptor 445b and key 860b and corresponding detent 440b and key detent 865b. As seen in FIGS. 10C-10D, the sensor assembly receiver 400b has the same construction as the sensor assembly receiver 400a except the receptor 445b and detent 440b of the body 490b have a different configuration than the receptor 445a and detent 440a of the sensor assembly receiver 400a. FIGS. 11D-11E illustrate the sensor assembly 800b that has the same construction as the sensor assembly 800a except the key 860b has a different configuration than the key 860a. The key 860b is configured to interact with the receptor 445b. Therefore, the sensor assembly receiver 400b is configured such that it can only be inserted into a connector 200 with a sensor assembly 800b. Further, as discussed earlier, the label 830b has a different design than the label 830a and can help a user identify the sensor attached to the sensor assembly 800b. As well, the sensor assembly receiver 400b can have the same color as the label 830b of the sensor assembly 800b. As discussed earlier, the sensor assembly receiver 400b and label 830b of the sensor assembly 800b can both have a red color, a blue color, a black color, or a gray color. Because the top tab 450b and the 320b are visible from the outer jacket 210 of the connector 200, the user is readily able to identify that the sensor assembly 800b can be properly inserted into the connector 200 with a sensor assembly receiver 400b.

As discussed above, the detent can provide the user with a mechanical "locking" feel as the proximal end of the sensor assembly is inserted into the connector. In addition to the interaction between the detent located on the sensor assembly and sensor assembly receiver, this is accomplished by the interaction between the pogo pins 1000 and the sensor side 812a of the sensor tab 810a. In the connector 200, as seen in FIG. 2B, the pogo pins 1000 extend from the inner shield 600 into the body 490a of the sensor assembly receiver 400a. As the sensor tab 810a is inserted into the body 490a the key detent 865a of the sensor assembly 800a begins to engage with the detent 440a of the sensor assembly receiver 400a. The insertion of the sensor tab 810a causes the surface of the sensor side 812a to contact the proximal end 1176 and retract the contact tip 1170 distally into the hollow barrel 1140. Once the proximal end of the sensor assembly 800a is fully inserted into the body 490a, the spring force of the springs 1180 in the plurality of pogo pins 1000 can push the contact tip 1170 in a proximal direction—causing the contact tip 1170 to extend out of the proximal opening 1160 of the hollow barrel 1140. As the contact tip 1170 of the plurality of pogo pins 1000 extend outwards, the proximal end of the sensor assembly receiver 400a will be pushed downward such that the key detent 865a and detent 440a are activated (e.g. fully engaged). This interaction can further provide the user with a mechanical "locking" feel which provides a tactile indication to the user that the sensor assembly has been properly inserted into the connector 200.

FIGS. 10E-10K and FIGS. 11F-11H provide an alternative embodiment of the engagement between the sensor assembly and sensor assembly receiver. In some embodiments, the sensor assembly receiver and sensor assembly can engage to reduce the wear on the electrical contacts on the surface of the sensor assembly. In some embodiments, the sensor assembly includes a structure on the proximal end to prevent jamming and to ensure that the sensor assembly enters the sensor assembly receiver at the correct angle.

In some embodiments, the sensor assembly receiver and sensor assembly can be configured to reduce the wear on the surface of the sensor assembly. As discussed above, as the sensor assembly is inserted into the sensor assembly receiver, the pogo pins can contact the traces located on the surface of the sensor assembly. As will be discussed below, because the pogo pins can be spring loaded in order to better contact the traces located on the surface of the sensor assembly, repeated insertions of the sensor assembly can cause significant wear on the surface of the sensor assembly receiver. FIGS. 10E-10K, 11F-11I, and 14A-14I illustrate an embodiment of the sensor assembly and sensor assembly receiver that can be configured to reduce the wear on the sensor surface of the sensor assembly.

Figure 10E:
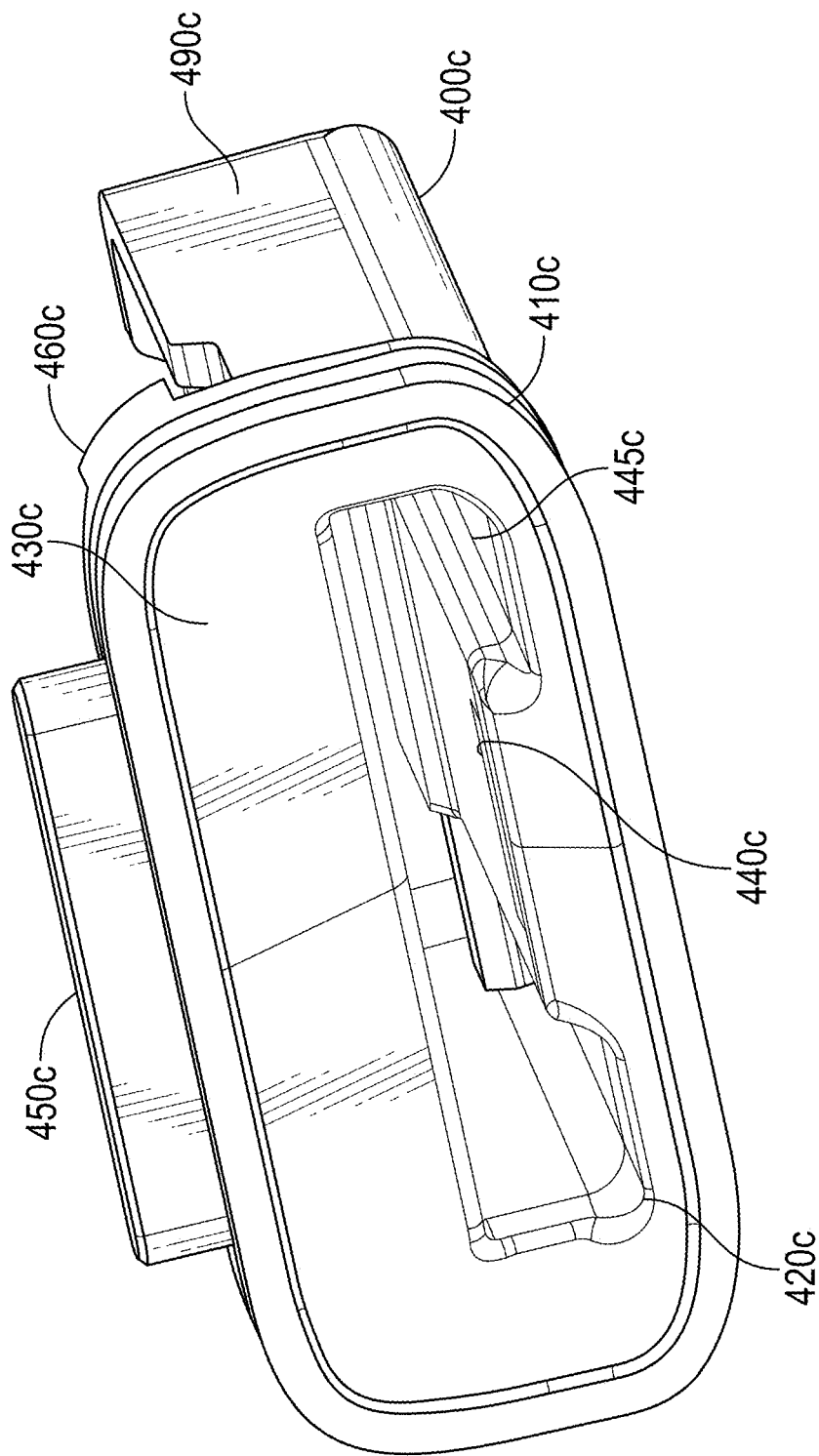
Figure 10F:
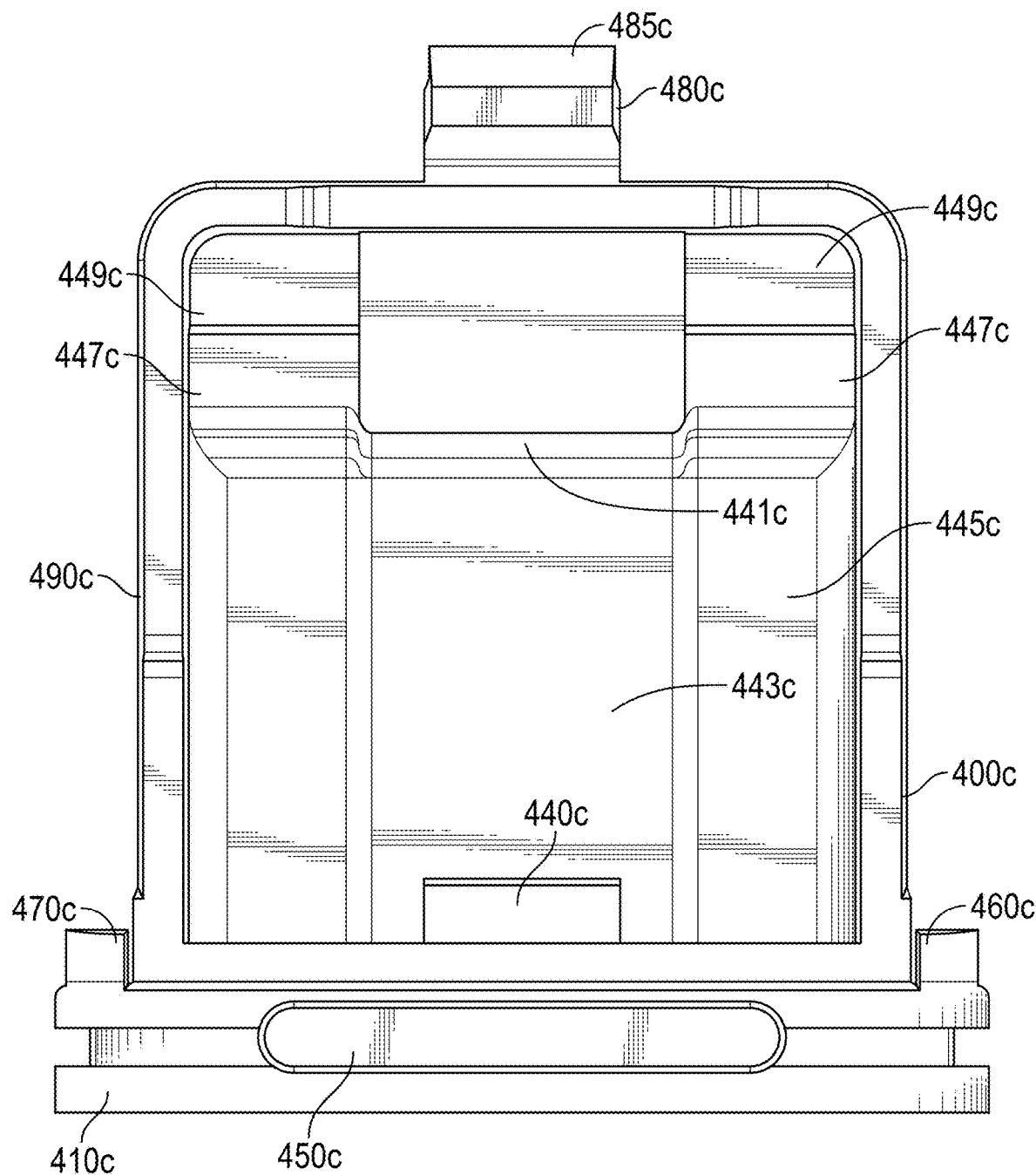
Figure 10G:
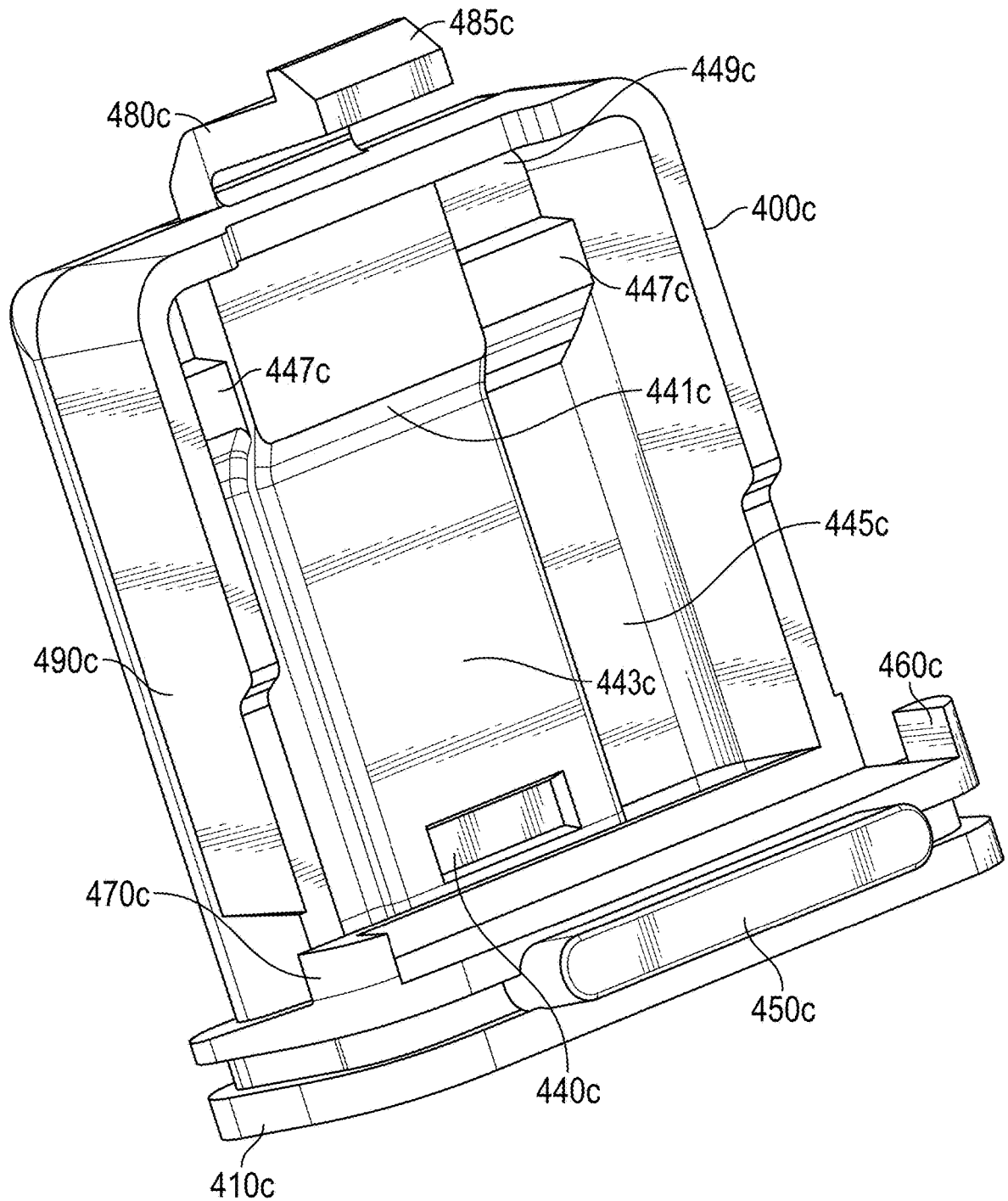
Figure 10H:
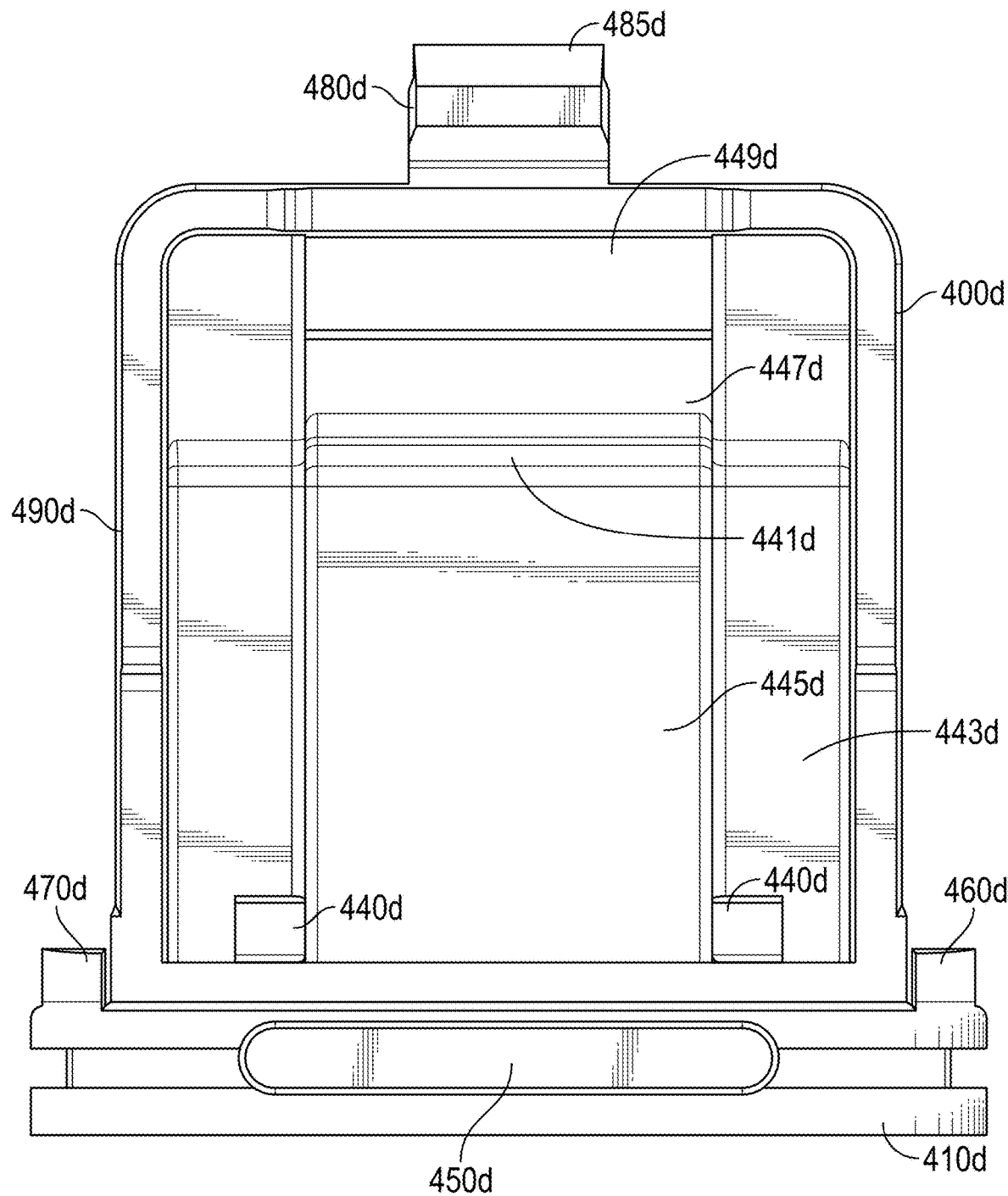
Figure 10I:
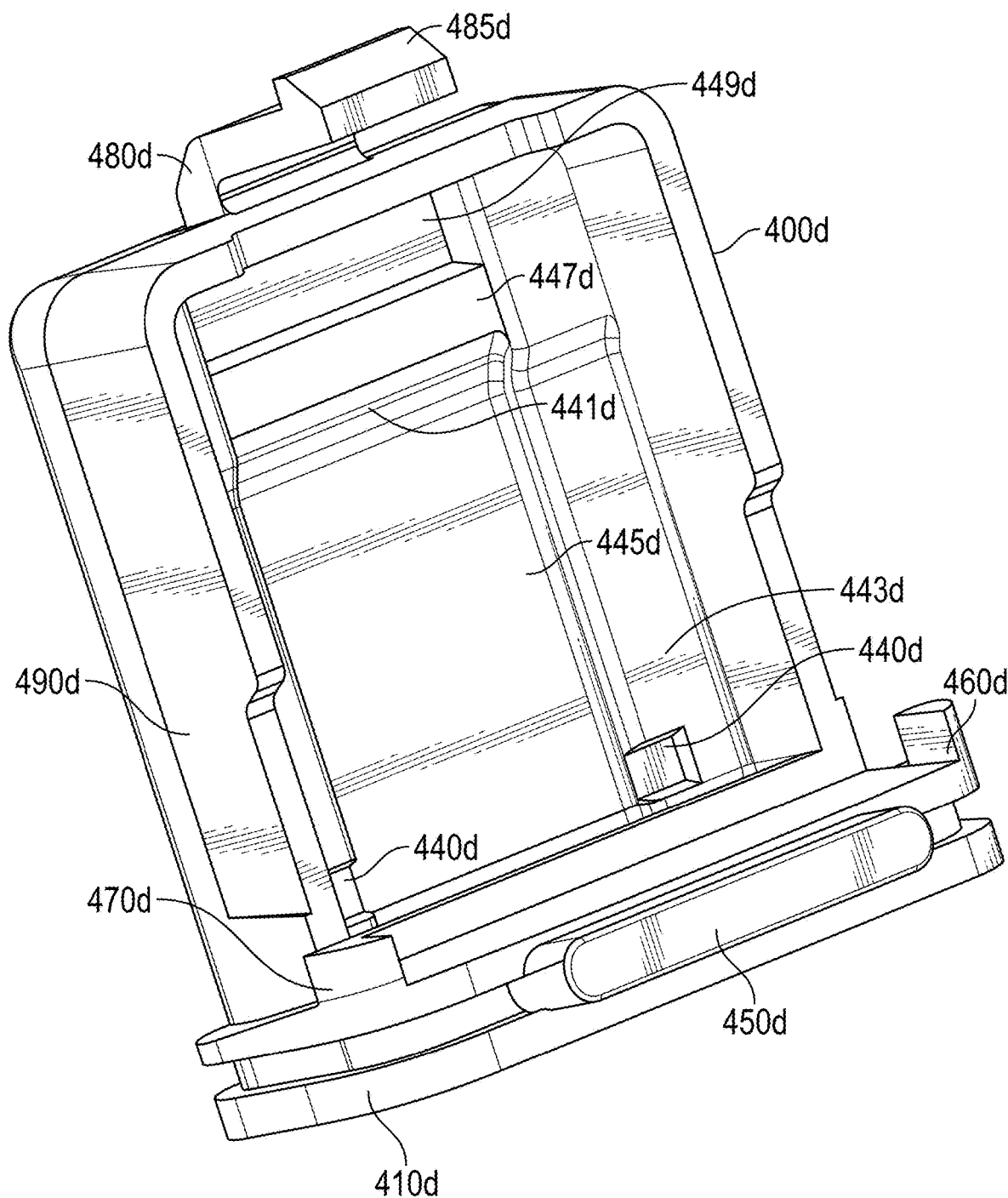
Figure 10J:
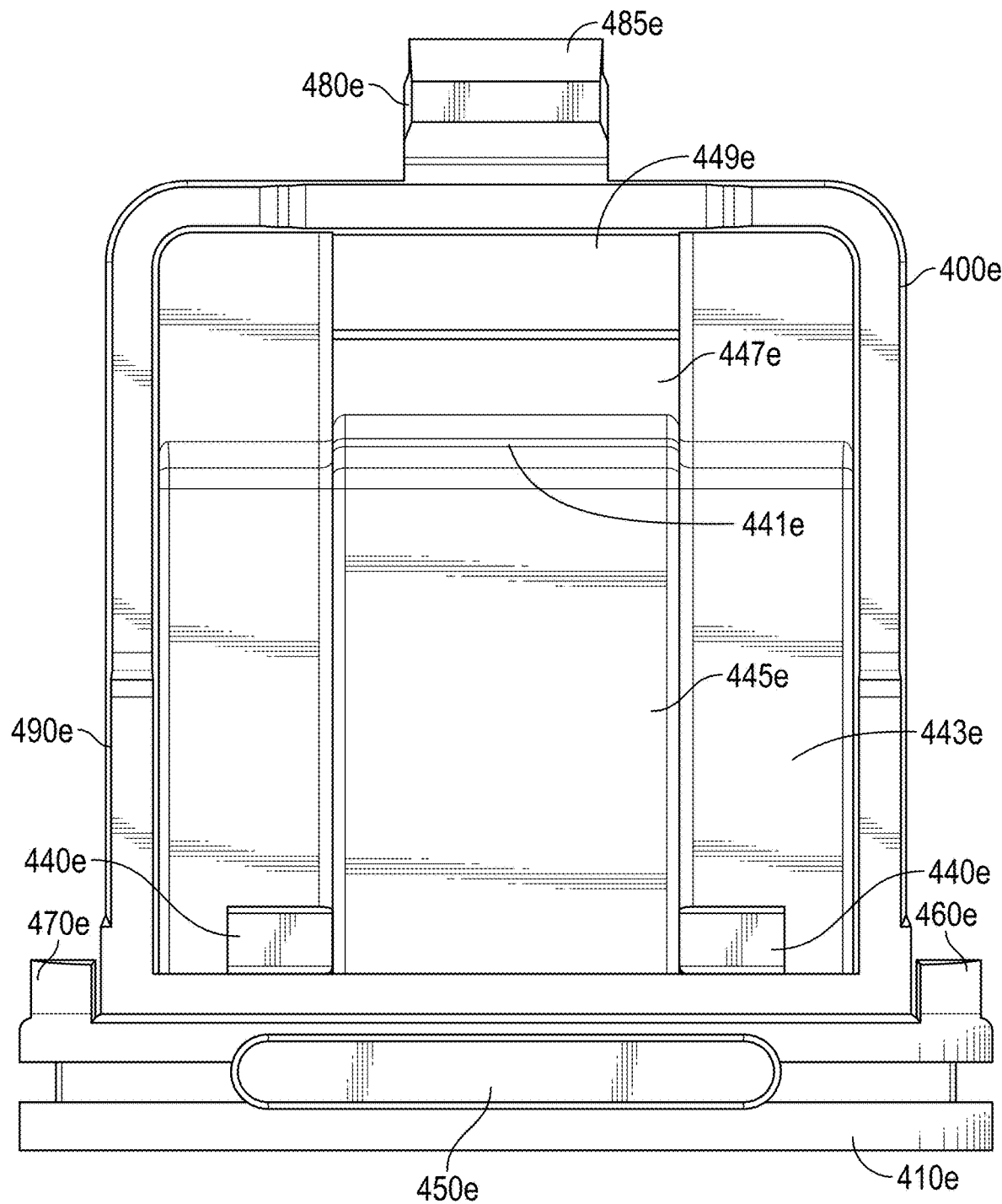
Figure 10K:
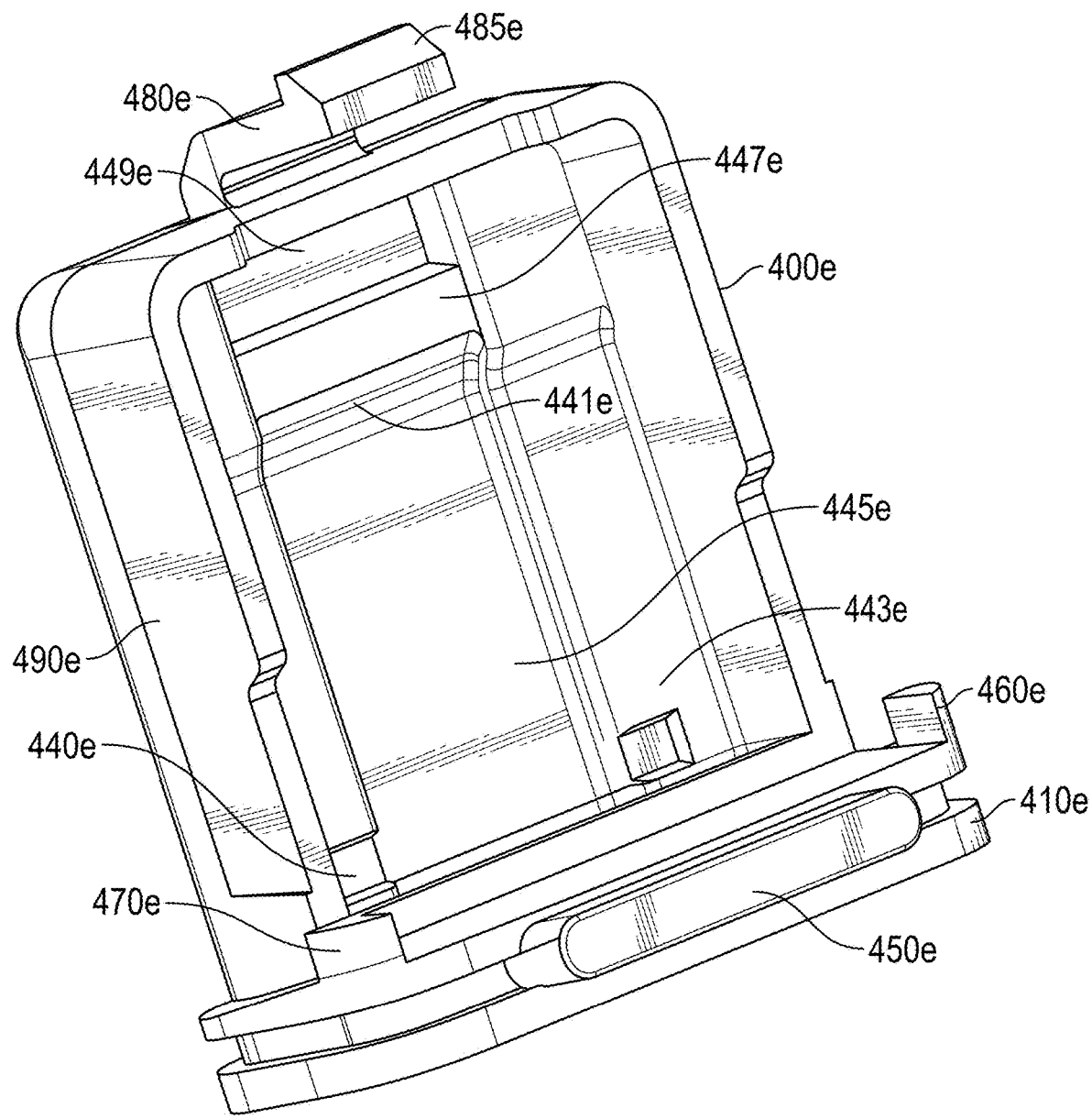

FIGS. 10E-10G illustrates one embodiment of a sensor assembly receiver configured to reduce the wear of the sensor surface of the sensor assembly. As can be seen, in some embodiments, the sensor assembly receiver 400c is very similar to the sensor assembly receiver illustrated in FIGS. 10A-10D. The sensor assembly receiver 400c can include a proximal end 410c and a body 490c. In some embodiments, the proximal end 410c can include a tapered surface 430c and an opening 420c. In some embodiments, the proximal end 410c includes a top tab 450c. As discussed above, the top tab 450c and the tapered surface 430c of the proximal end 410c can have a color that corresponds with a portion of the sensor assembly in order to provide a visual indication to the user that the correct sensor assembly has been attached to the property connector with the corresponding sensor assembly receiver. In some embodiments, as discussed above, the sensor assembly receiver 400c can include a plurality of arms that allow the sensor assembly receiver 400c to be secured within the connector 200. Like the sensor assembly receivers discussed above, the sensor assembly receiver 400c can include a first arm 460c, a second arm 470c, distal arm 480c, and distal tab 485c. FIGS. 10H-10K illustrates two additional embodiments of sensor assembly receivers configured to reduce the wear of the sensor surface of the sensor assembly. FIGS. 10H-10I illustrates the sensor assembly receiver 400d and FIGS. 10J-10K illustrates the sensor assembly receiver 400c. The sensor assembly receiver 400d and sensor assembly receiver 400e can similarly include the parts described with regard to sensor assembly receiver 400a, sensor assembly receiver 400b, and sensor assembly receiver 400c described above.

The sensor assembly receiver embodiments illustrated in FIGS. 10E-10K, like the sensor assembly receivers illustrated in FIGS. 10A-10D, is configured to receive a key from a corresponding sensor assembly. In some embodiments, the sensor assembly receiver embodiments are also configured to include a detent structure that can interact with a corresponding detent structure on the underside of the sensor assembly to provide mechanical feedback. In some embodiments, the sensor assembly receiver includes a ramp that can raise the sensor assembly within the sensor assembly receiver.

FIGS. 10E-10G, illustrates a sensor assembly receiver 400c that can include a receptor 445c and a detent 440c. As can be better seen in FIGS. 10F-10G, the sensor assembly receiver 400c includes a receptor 445c that is located on two sides of the bottom surface 443c of the sensor assembly receiver 400c. The receptor 445c of the sensor assembly receiver 400c can include receptor protrusions 447c near the distal end of the sensor assembly receiver 400c. The receptor protrusion 447c creates a raised portion from the receptor 445c. The receptor 445c can also include a receptor end 449c located at the distal end of the sensor assembly receiver 400c that is no longer elevated. The sensor assembly receiver 400c can also include a detent 440c. As can be seen in FIG. 10F, the detent 440c can be located near the proximal end of the sensor assembly receiver 400c and form a groove in the bottom surface 443c of the sensor assembly receiver 400c. As well, in some embodiments, the sensor assembly receiver 400c can include an angled surface 441c. As can be seen in FIG. 10G, the angled surface 441c raises the bottom surface 443c.

The two embodiments illustrated in FIGS. 10H-10K provide similar structures as discussed above. FIGS. 10H-10I illustrates a sensor assembly receiver 400d that has a receptor 445d that is located at the center of the bottom surface 443d of the sensor assembly receiver 400d. The receptor 445d of the sensor assembly receiver 400d can include receptor protrusion 447d near the distal end of the sensor assembly receiver 400d. The receptor protrusion 447d creates a raised portion from the receptor 445d. The receptor 445d can also include a receptor end 449d located at the distal end of the sensor assembly receiver 400d that is not elevated. The sensor assembly receiver 400d can also include a detent 440d. As can be seen in FIG. 10H, the detent 440d is composed of two portions that are located on either side of the proximal end of the receptor 445d and form grooves in the bottom surface 443d of the sensor assembly receiver 400d. As well, in some embodiments, the sensor assembly receiver 400d can include an angled surface angled surface 441d. As can be seen in FIG. 1, the angled surface 441d raises the bottom surface 443c. FIGS. 10J-10K illustrates a sensor assembly receiver 400e that has a similar configuration to the sensor assembly receiver 400d described above. In the embodiment illustrated in sensor assembly receiver 400c, compared to the sensor assembly receiver 400d, the receptor 445e is narrower and the two detents 440e are longer.

Figure 11F:
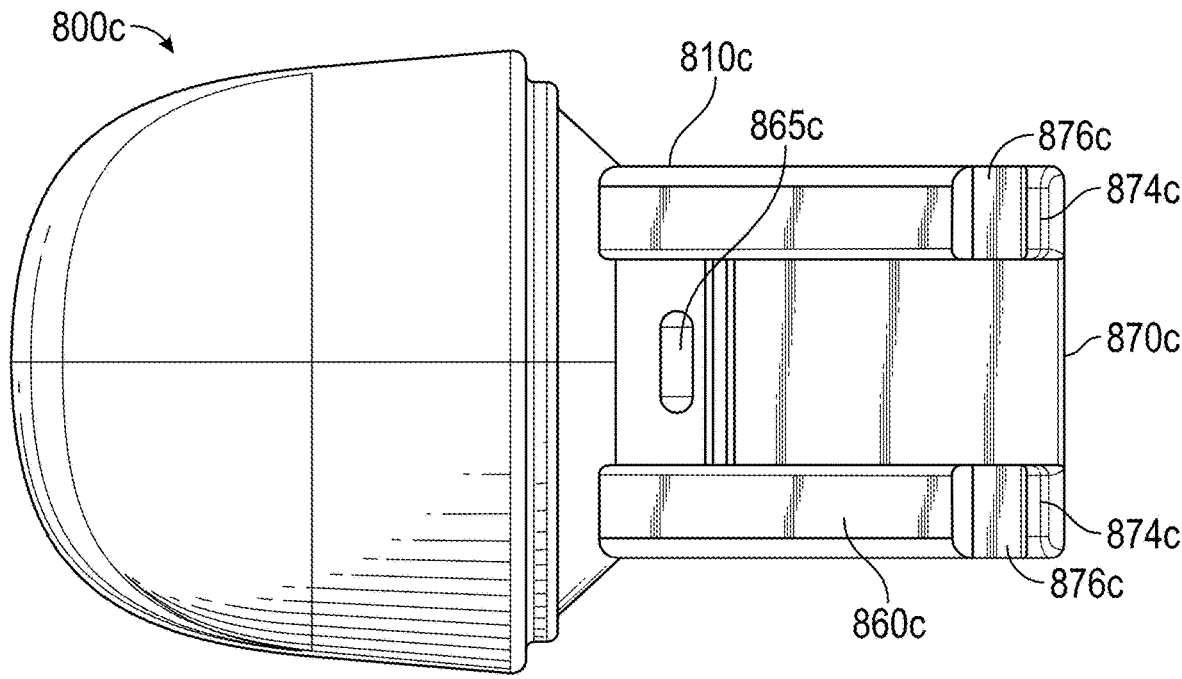
Figure 11G:
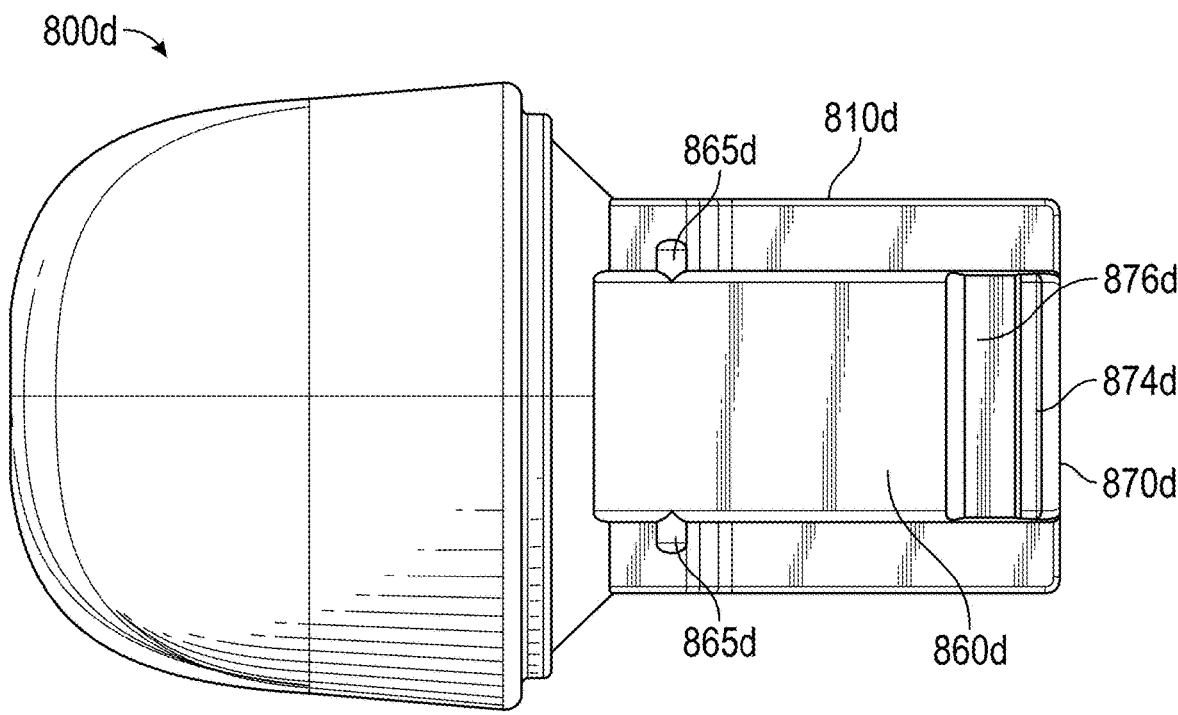
Figure 11H:
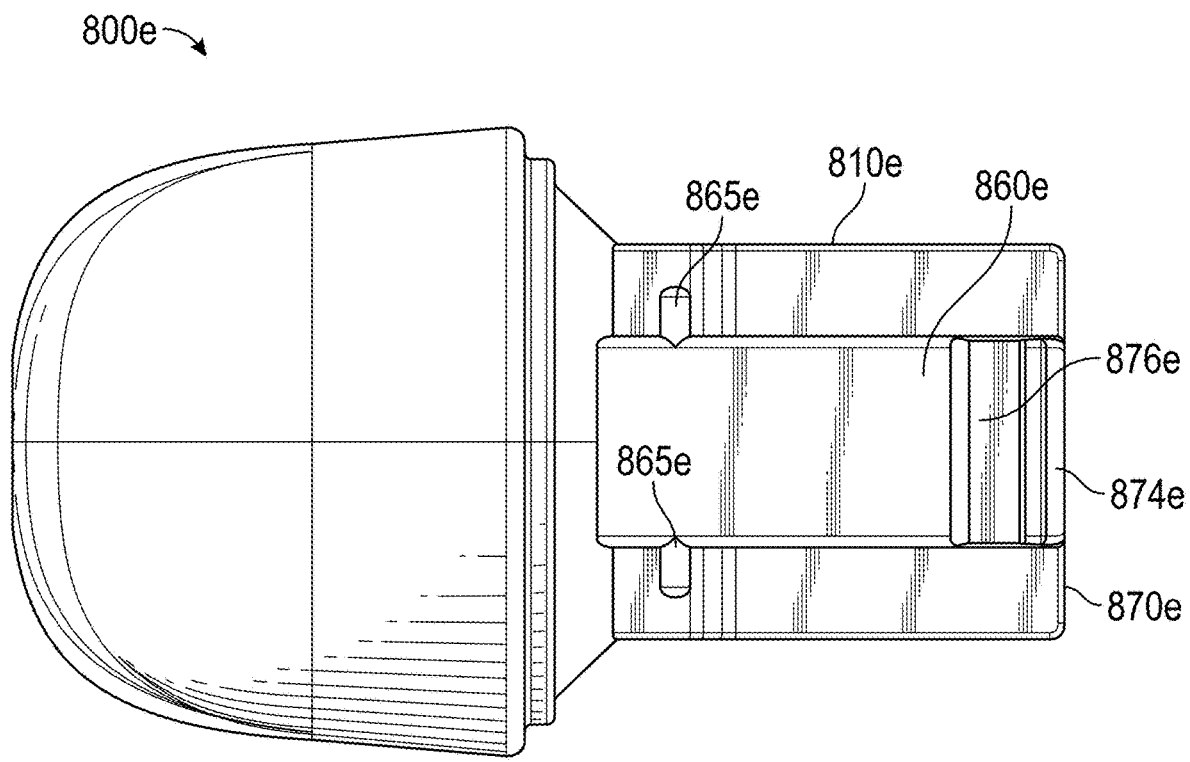

As discussed above, the sensor assembly can be configured to include a key and detent structures that are structured to engage with the sensor assembly receiver that the sensor on the sensor assembly is configured to form an electrical connection with. FIGS. 11F-H illustrate three embodiments of the sensor assembly. FIG. 11F illustrates a sensor assembly 800c that is configured to be inserted into a connector 200 with a sensor assembly receiver 400c as illustrated in FIGS. 10E-10G. FIG. 11G illustrates a sensor assembly 800d that is configured to be inserted into a connector 200 with a sensor assembly receiver 400d as illustrated in FIGS. 10H-10I. FIG. 11H illustrates a sensor assembly 800e that is configured to be inserted into a connector 200 with a sensor assembly receiver 400e as illustrated in FIGS. 10J-10K.

FIG. 11F illustrates the underside of the sensor tab 810c of the sensor assembly 800c. The sensor assembly 800c can include a key 860c. In this embodiment, the key 860c is composed of two rectangular structures on the underside of the sensor tab 810c. As will be discussed in more detail below, the key 860c is configured to engage with the receptor 445c of the sensor assembly receiver 400c. On the proximal end 870c of the key 860c, the key 860c can include a curved bottom receptor 876c and a protruding bottom protrusion 874c. The bottom receptor 876c and bottom protrusion 874c can be configured to engage with the receptor protrusion 447c and the receptor end 449c respectively. The sensor assembly 800c can also include a key detent 865c. In some embodiments, the key detent 865c is located near the distal end of the sensor tab 810c between the two structures making up the key 860c. As will be discussed in more detail below, the key detent 865c is configured to engage with the detent 440c of the sensor assembly receiver 400c.

Figure 11I:
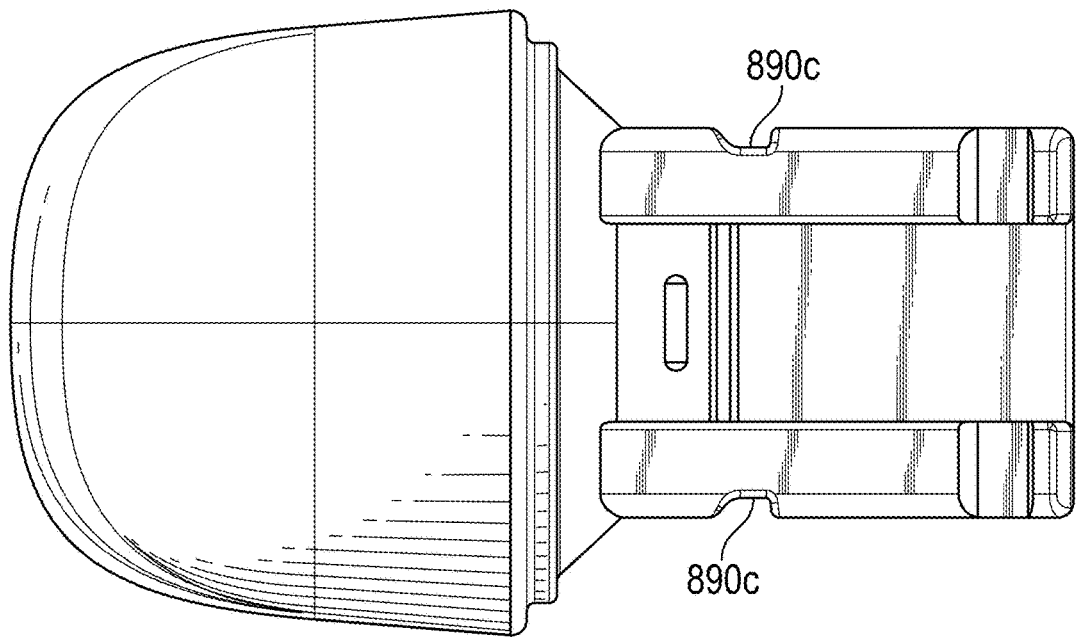
FIGS. 11I-11K illustrate bottom views of alternative embodiments of the sensor assemblies illustrated in FIGS. 11F-11H.
Figure 11J:
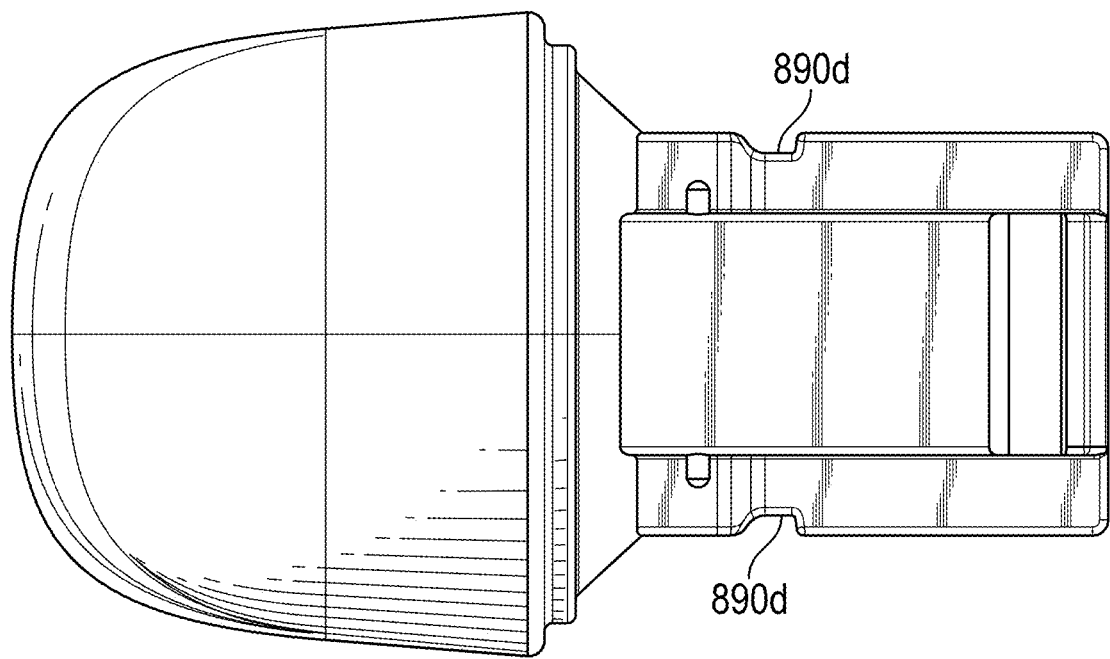
Figure 11K:
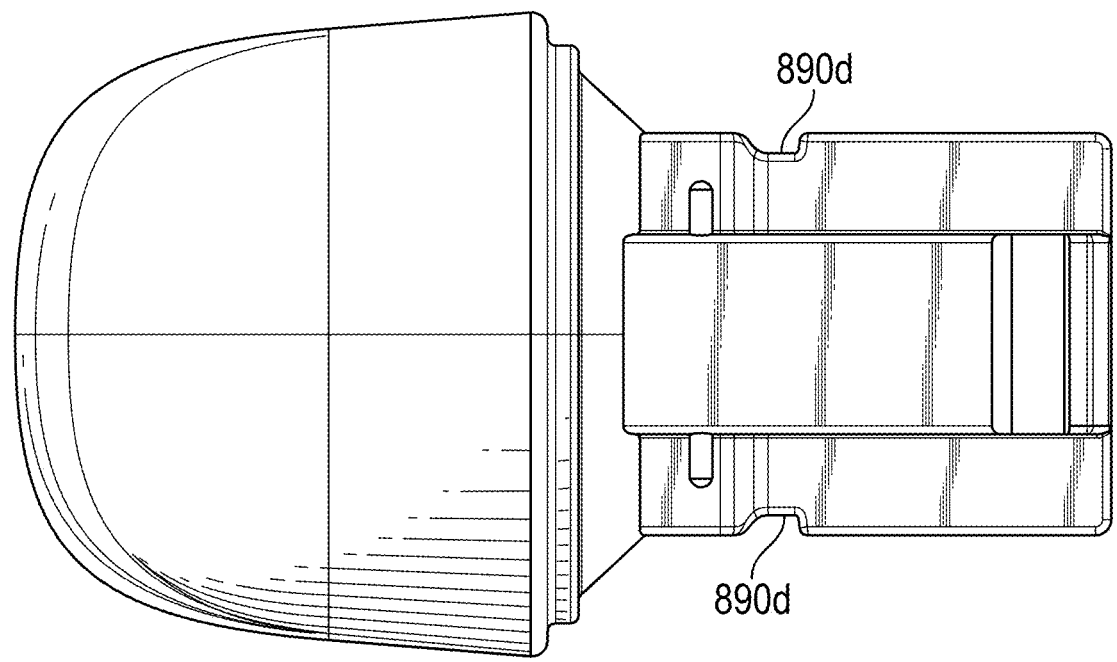
Figure 11L:
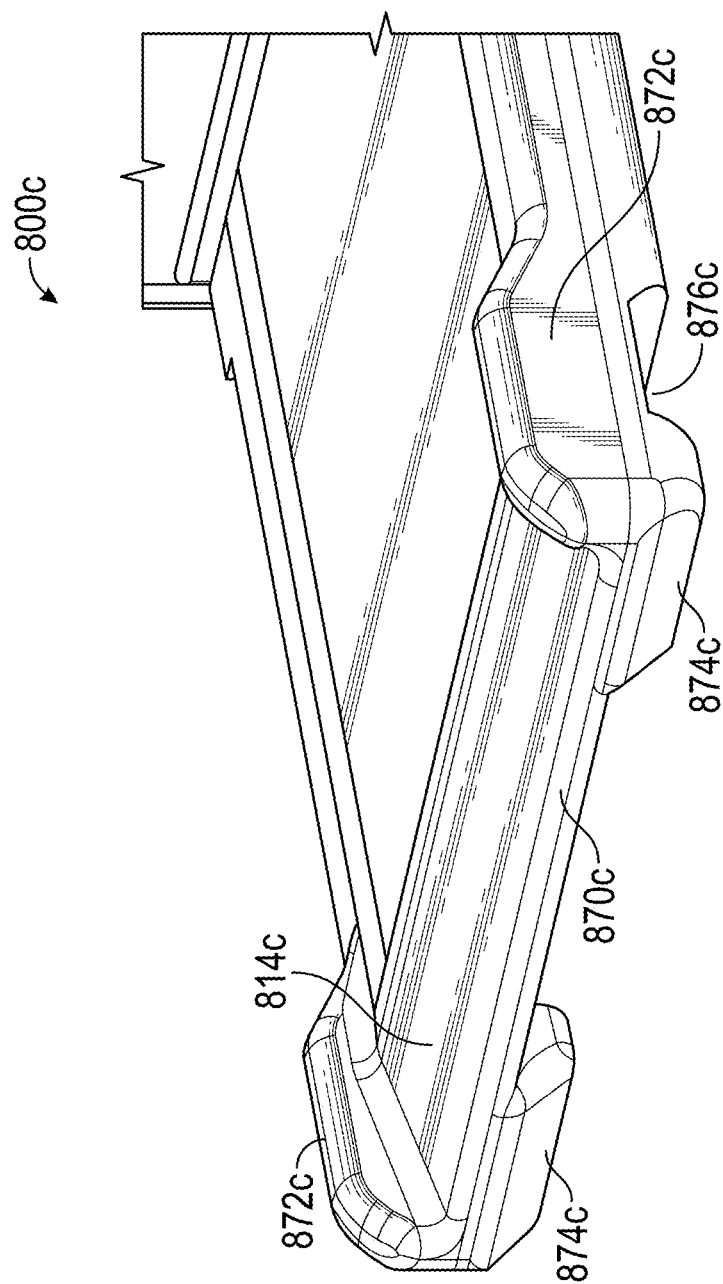
FIGS. 11L-11M illustrate a proximal end view of two embodiments of the sensor assembly.
Figure 11M:
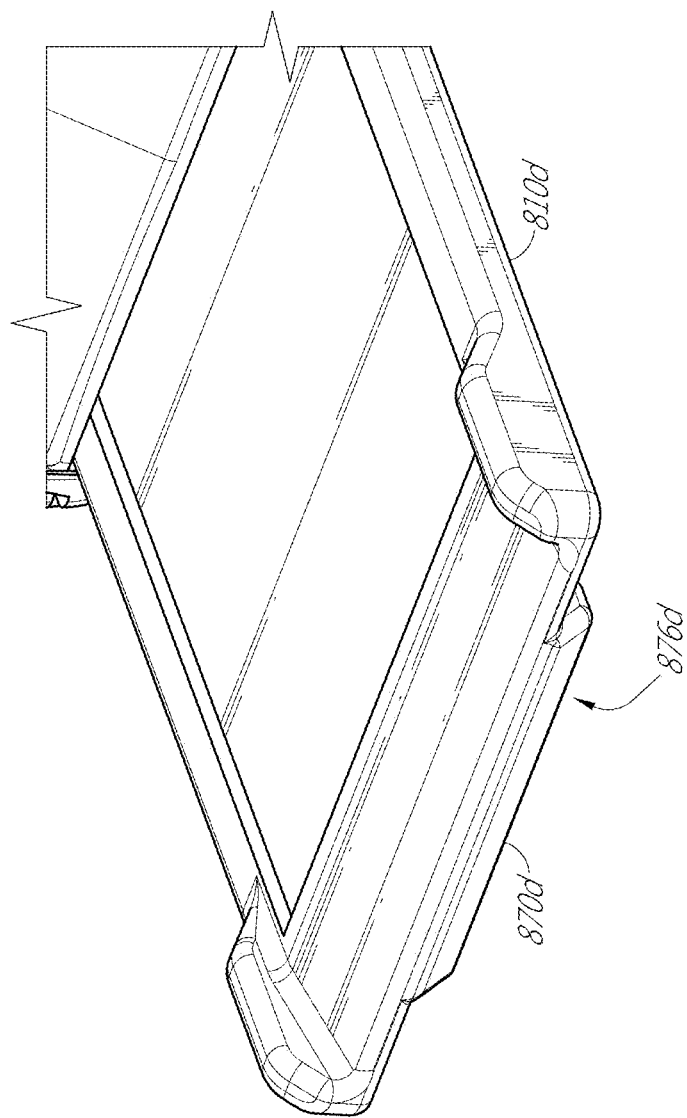

FIG. 11G illustrates sensor assembly 800d, another embodiment of the underside of the sensor tab of a sensor assembly and FIG. 11M illustrates a perspective view of the sensor tab 810d. The sensor assembly 800d can also include a key 860d. In this embodiment, the key 860d is composed of a rectangular structure centered on the underside of the sensor tab 810d. As will be discussed in more detail below, the key 860d is configured to engage with the receptor 445d of the sensor assembly receiver 400d. On the proximal end 870d of the key 860d, the key 860d can include a curved bottom receptor 876d and a protruding bottom protrusion 874d. The bottom receptor 876d and bottom protrusion 874d can be configured to engage with the receptor protrusion 447d and the receptor end 449d respectively. The sensor assembly 800d can also include two key detents 865d. In some embodiments, the two key detents 865d are located near the distal end of the sensor tab 810d on either side of the key 860d. As will be discussed in more detail below, the two key detents 865d is configured to engage with the detents 440d of the sensor assembly receiver 400d. FIG. 11H illustrates a sensor assembly 800e that has a similar configuration to the sensor assembly 800d described above. In the embodiment illustrated in sensor assembly 800e, compared to the sensor assembly 800d, the key 860e is wider and the two key detents 865e are longer in order to engage with the receptor 445e and detents 440e of sensor assembly receiver 400c. As well, the bottom receptor 876d and bottom protrusion 874d are configured to engage with the receptor protrusion 447e and receptor end 449e respectively.

In some embodiments, the sensor assemblies can include additional structures that allow the sensor assemblies to be further secured within the connector 200. For example, FIGS. 11I-11L illustrates embodiments of sensor assemblies from FIGS. 11F-11H that further include structures on either side of the sensor tab that can be secured by the connector 200. In some embodiments, the structures on either side of the sensor tab can be configured to serve as a locking structure that secures the sensor tab to the connector exhaust line 200. FIG. 11I illustrates the sensor assembly 800c with a sensor tab 810c that includes an indentation 890c on either side of the sensor tab 810c. As noted above, in some embodiments, the indentations 890c can serve as a locking structure that engages the connector 200. FIG. 11J illustrates the sensor assembly 800d with a sensor tab 810d that includes an indentation 890d on either side of the sensor tab 810d. In some embodiments, the indentations 890d can serve as a locking structure that engages the connector 200. FIG. 11K illustrates the sensor assembly 800e with a sensor tab 810e that includes an indentation 890e on either side of the sensor tab 810c. In some embodiments, the indentations 890e can serve as a locking structure that engages the connector 200.

In operation, the connector 200 can include a locking structure that can be configured to interact with the indentations on either side of the sensor tab. In some embodiments, this locking structure prevents movement within the connector 200. In some variants, the connector 200 further includes an unlocking mechanism that releases the locking structure from the sensor tab. In some examples, the sensor assembly cannot be removed from the connector 200 without first actuating the unlocking mechanism. In other embodiments, the sensor tab can include other structures that allow the connector 200 to secure the sensor assembly within the connector 200.

In some embodiments, the sensor assembly can include a sensor tab with protrusions located on either side of the proximal end. In some variants, the protrusion can ensure that the sensor assembly is inserted into the sensor assembly receiver parallel to the pogo pins 1000 that extend through the sensor assembly receiver. In some embodiments, this can prevent the sensor assembly from being inserted at an angle and jamming the pogo pins 1000. FIG. 11L illustrates an example of the proximal end 870c of the sensor assembly 800c. As illustrated, in some embodiments, the proximal end 870c of the sensor assembly 800c includes a proximal protrusion 872c on either side of the top surface of the proximal end 870c of the sensor tab 810c. In some embodiments, the height of the proximal protrusion 872c ensures that the sensor tab 810c is inserted through the opening 420c at a distance from the top of the opening 420c and therefore at a distance from the pogo pins 1000.

Figure 14A:
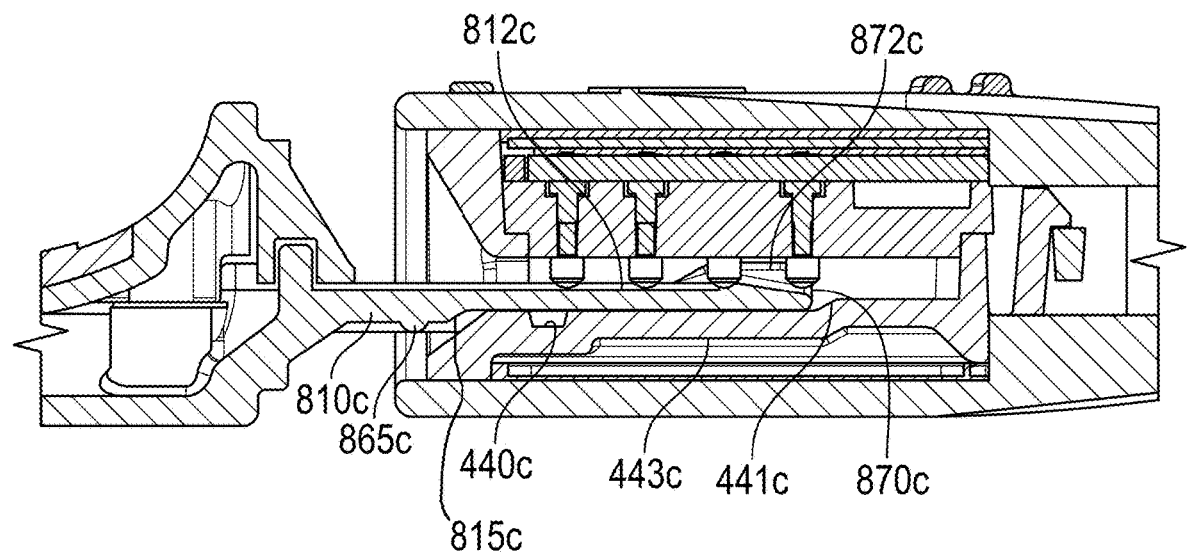
FIGS. 14A-14I illustrate various cross-sectional views of embodiments of sensor assemblies inserted into corresponding embodiments of sensor assembly receivers.
Figure 14B:
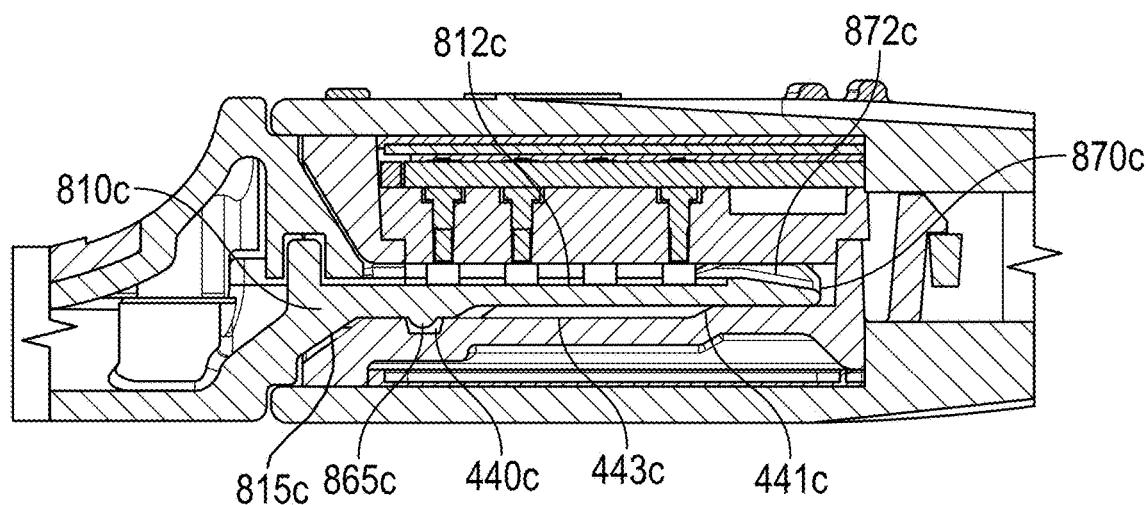
Figure 14C:
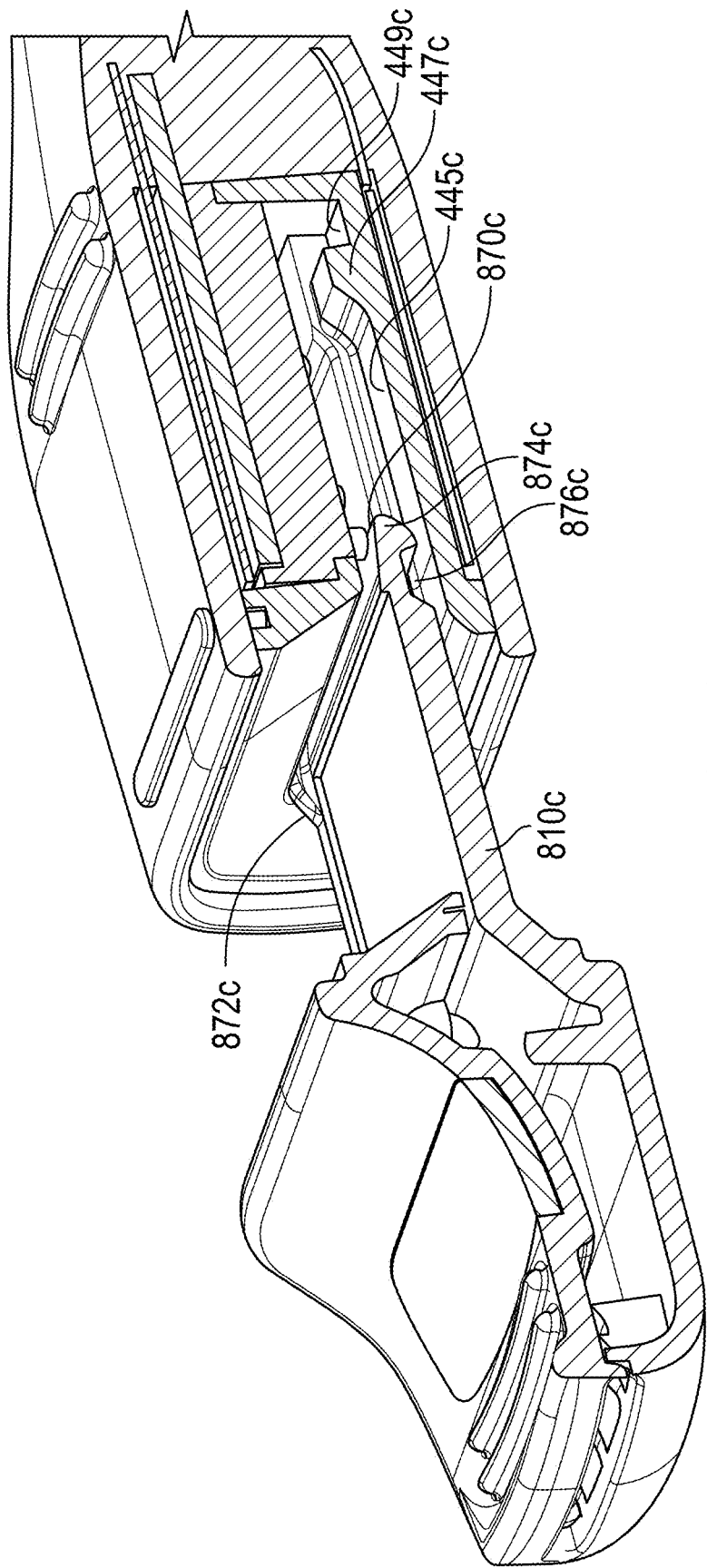
Figure 14D:
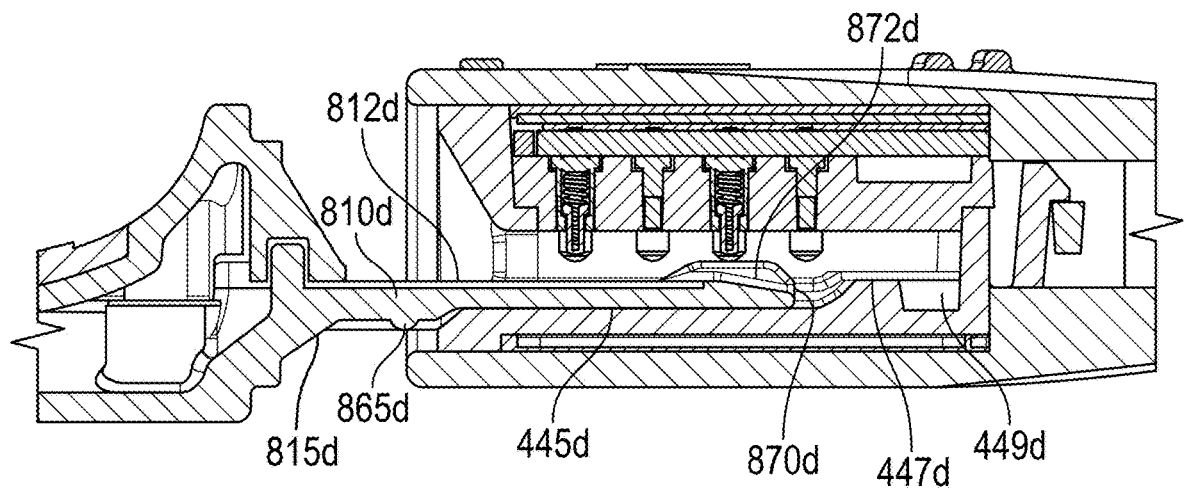
Figure 14E:
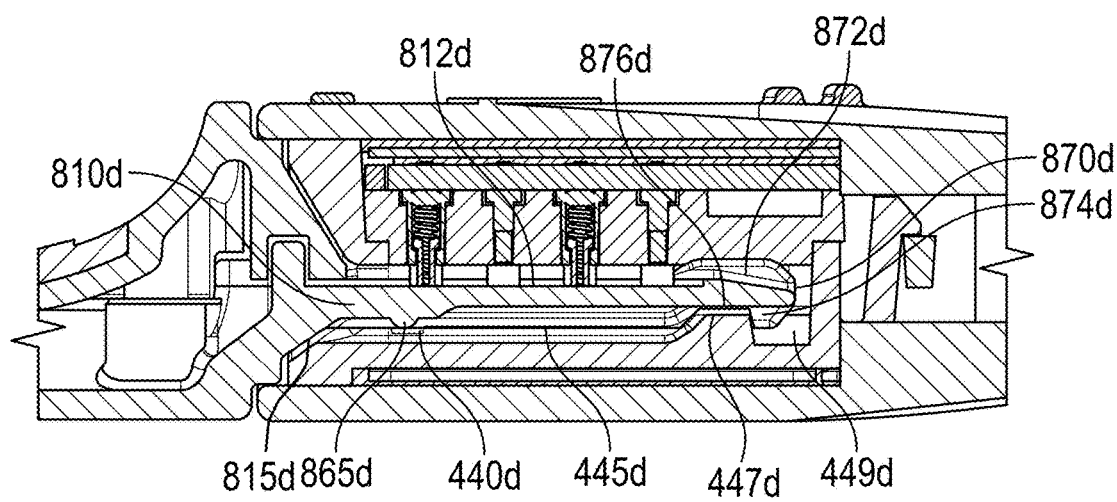
Figure 14F:
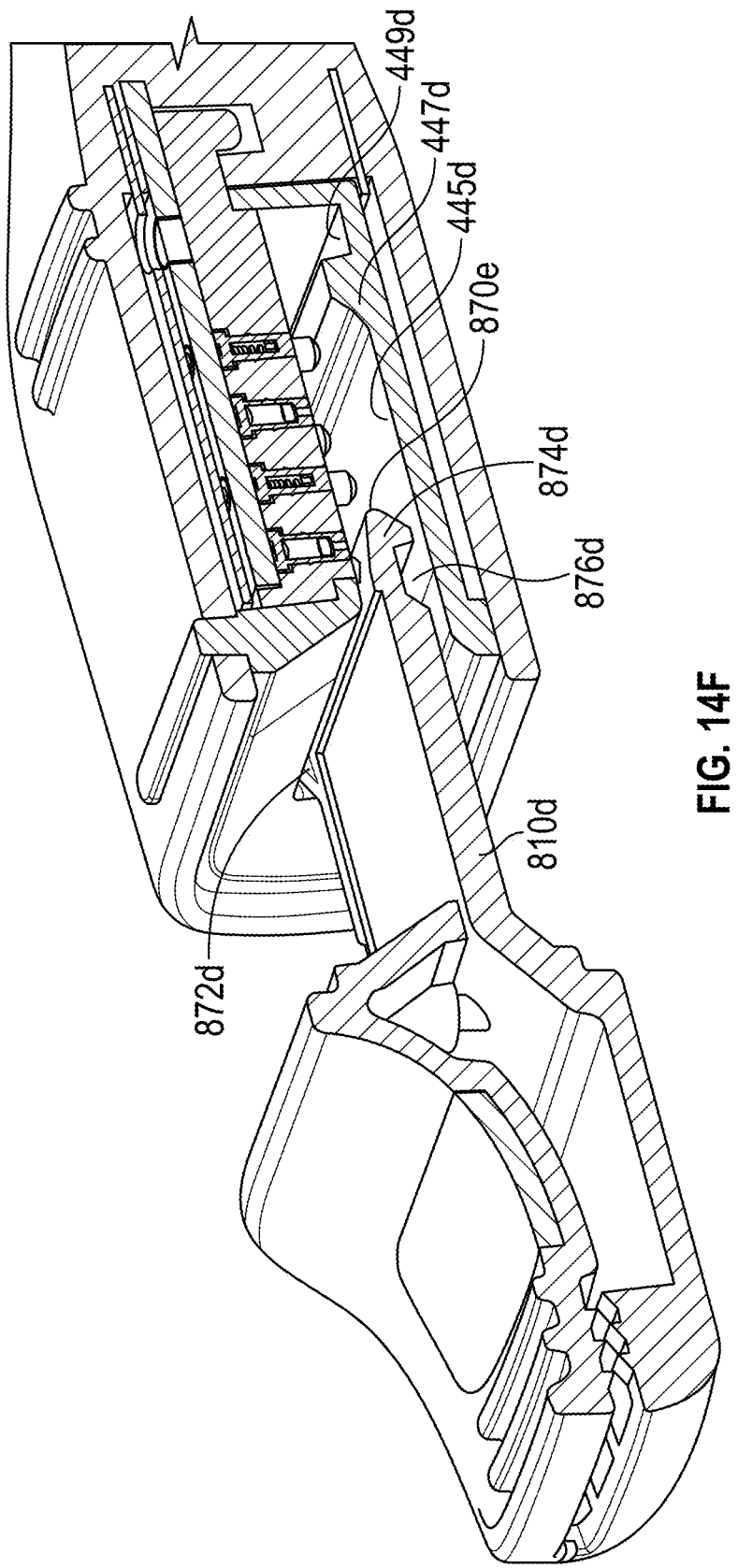

The sensor assembly receiver embodiments illustrated in FIGS. 10E-10K can reduce the wear on the surface sensor assembly through the configuration of the receptor and detent located on the insides surface of the sensor assembly receiver. As discussed above, the sensor assembly receiver includes a receptor that is configured to receive a key located on the underside of the sensor assembly. As discussed above, this ensures that the sensor assembly receiver can only receive certain sensor assemblies. As well, it ensures that the sensor assembly is attached to the sensor assembly receiver with the sensor side facing up so as to properly form an electrical connection with the pogo pins located inside the connector. In some embodiments, the detent located inside the sensor assembly receiver can engage with a corresponding detent located on the underside of the sensor assembly. As discussed above, the detent provides the user with a tactile or mechanical feedback to indicate to the user that the sensor assembly has been properly inserted. In the embodiments of the sensor assembly receivers illustrated in FIGS. 10E-10K, the sensor assembly receiver includes a ramp that brings the surface of the sensor assembly receiver FIGS. 14A-14I illustrate the interaction between the sensor assembly receiver and sensor assembly discussed above in FIGS. 10E-10K and 11F-11I respectively. FIGS. 14A-14C illustrate the sensor assembly 800c as it is inserted into the sensor assembly receiver 400c. FIGS. 14A-14B provide a side cross-sectional view of the sensor assembly 800c as it is incrementally inserted into the sensor assembly receiver 400c. FIG. 14C provides a top perspective two-thirds cross-sectional view of the sensor assembly 800c as it is partially inserted into the sensor assembly receiver 400c. FIGS. 14D-14F illustrate the sensor assembly 800d as it is inserted into the sensor assembly receiver 400d. FIGS. 14D-E provide a side cross-sectional view of the sensor assembly 800d as it is incrementally inserted into the sensor assembly receiver 400d. FIG. 14F provides a top perspective two-thirds cross-sectional view of the sensor assembly 800e as it is partially inserted into the sensor assembly receiver 400c.

Figure 14G:
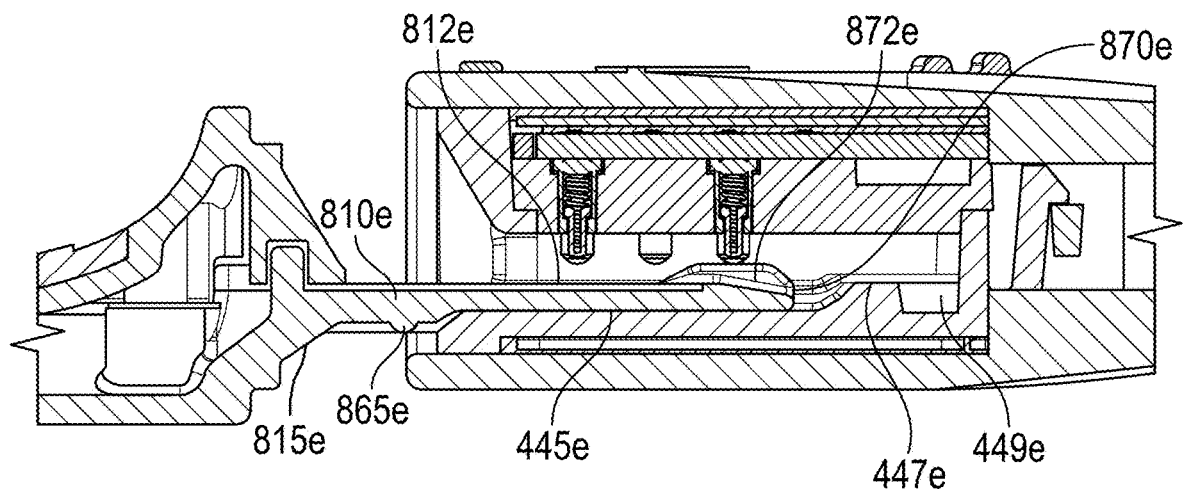
Figure 14H:
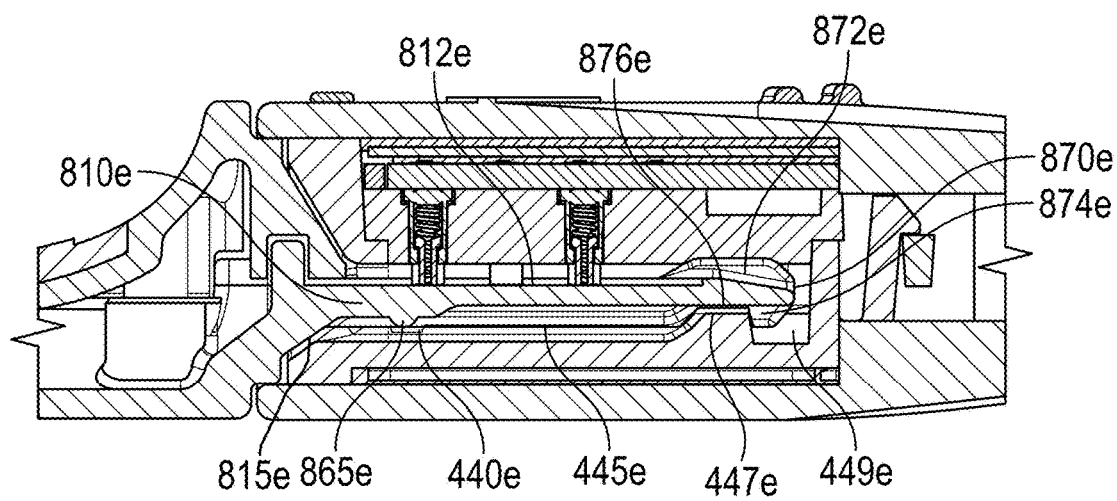
Figure 14I:
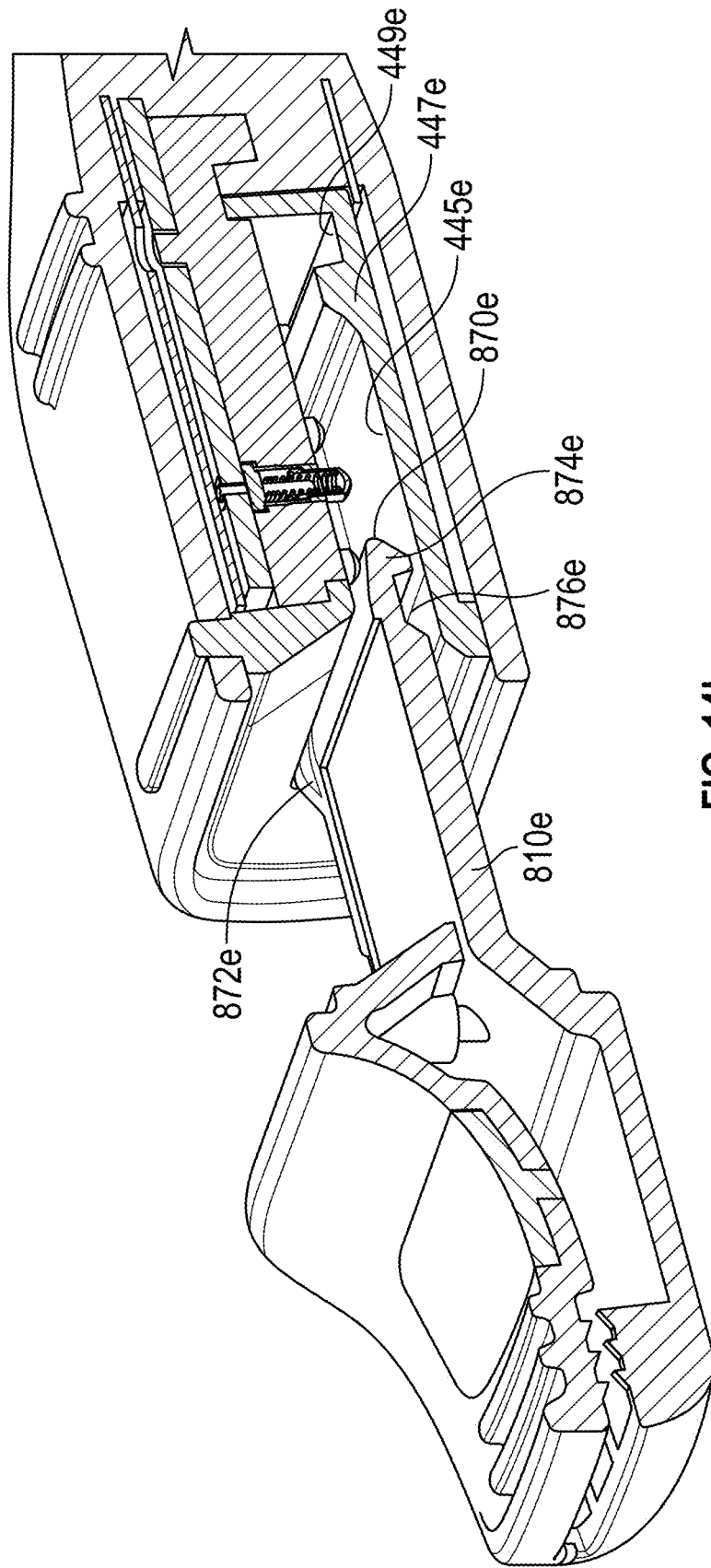

FIGS. 14G-14I illustrate the sensor assembly 800e as it is inserted into the sensor assembly receiver 400c. FIGS. 14G-14H provide a side cross-sectional view of the sensor assembly 800e as it is incrementally inserted into the sensor assembly receiver 400c. FIG. 14I provides a top perspective two-thirds cross-sectional view of the sensor assembly 800c as it is partially inserted into the sensor assembly receiver 400c.

In operation, as discussed above, in some embodiments the sensor assembly and sensor assembly receiver can interact to reduce the wear on the top surface of the sensor assembly as its received in the sensor assembly receiver. As illustrated in FIG. 14A, as the sensor assembly 800c is inserted into the sensor assembly receiver 400c, the sensor side 812c of the sensor tab 810c can interact with the plurality of pogo pins 1000 that extend downward into the sensor assembly receiver 400c. Because each of the plurality of pogo pins 1000 can be spring loaded, the closer the sensor side 812c is to the pogo pins 1000, the greater the pressure is exerted on the sensor side 812c of the sensor tab 810c as the sensor assembly 800c is inserted. In some embodiments, this can cause increased wear of the sensor on the sensor assembly 800c. In some examples, as illustrated in FIGS. 14A-14B, wear on the sensor side 812c of the sensor tab 810c is reduced by creating two levels on the bottom surface 443c of the sensor assembly receiver 400c for the sensor assembly 800c to move against. As is illustrated in FIG. 14A, when the sensor assembly 800c is first inserted into the sensor assembly receiver 400c, the sensor tab 810c moves adjacent to the bottom surface 443c. In some embodiments, the bottom surface 443c is configured such that it reduces the interaction and pressure placed on the sensor side 812c by the plurality of pogo pins 1000. Then, as illustrated in FIG. 14B, as the sensor tab 810c of the sensor assembly 800c is further inserted into sensor assembly 800c, an angled surface 441c of the bottom surface 443c serves as a ramp to move the sensor tab 810c to an elevated level. In some embodiments, the sensor tab 810c further includes a ramp 815c on the distal end that can also serve to move the sensor tab 810c to an elevated level. This elevated level brings the sensor tab 810c closer against the plurality of pogo pins 1000 in order to provide a more secure electrical connection with the sensor assembly receiver 400c. In some embodiments, the key detent 865c and detent 440c, in addition to providing the user with a mechanical feedback, can serve to lock the sensor tab 810c of the sensor assembly 800c in the elevated configuration. In addition, in some examples, as illustrated in FIG. 14C, the bottom receptor 876c and bottom protrusion 874c located at the proximal end 870c of the sensor tab 810c can interact with the receptor protrusion 447c and receptor end 449c of the sensor assembly receiver 400c to secure the sensor assembly 800c in the sensor assembly receiver 400c. As illustrated in FIGS. 14D-14F and 14G-14I, the sensor assembly 800d and sensor assembly receiver 400d and sensor assembly 800e and sensor assembly receiver 400e interact in a similar or identical manner as discussed above. These embodiments further illustrate the goal of reducing wear on the sensor side of the sensor tab in various embodiments. The numbering convention of FIGS. 14A-14C applies to FIGS. 14D-14F except the "c" is replaced with a "d" and FIGS. 14G-14I except the "c" is replaced with an "e."

As discussed above, one of the advantages of the present design is the ability of the connector and sensor assembly to accommodate various sensors with a wide range of electrical contacts. This is accomplished through the use of pogo pins 1000 and a sensor with a plurality of electrical contacts on its surface. As will discussed more fully below, because the connector 200 can accommodate a large number of electrical contacts, the configuration of the pogo pins 1000 in the connector 200 is important to prevent short circuiting.

Figure 12A:
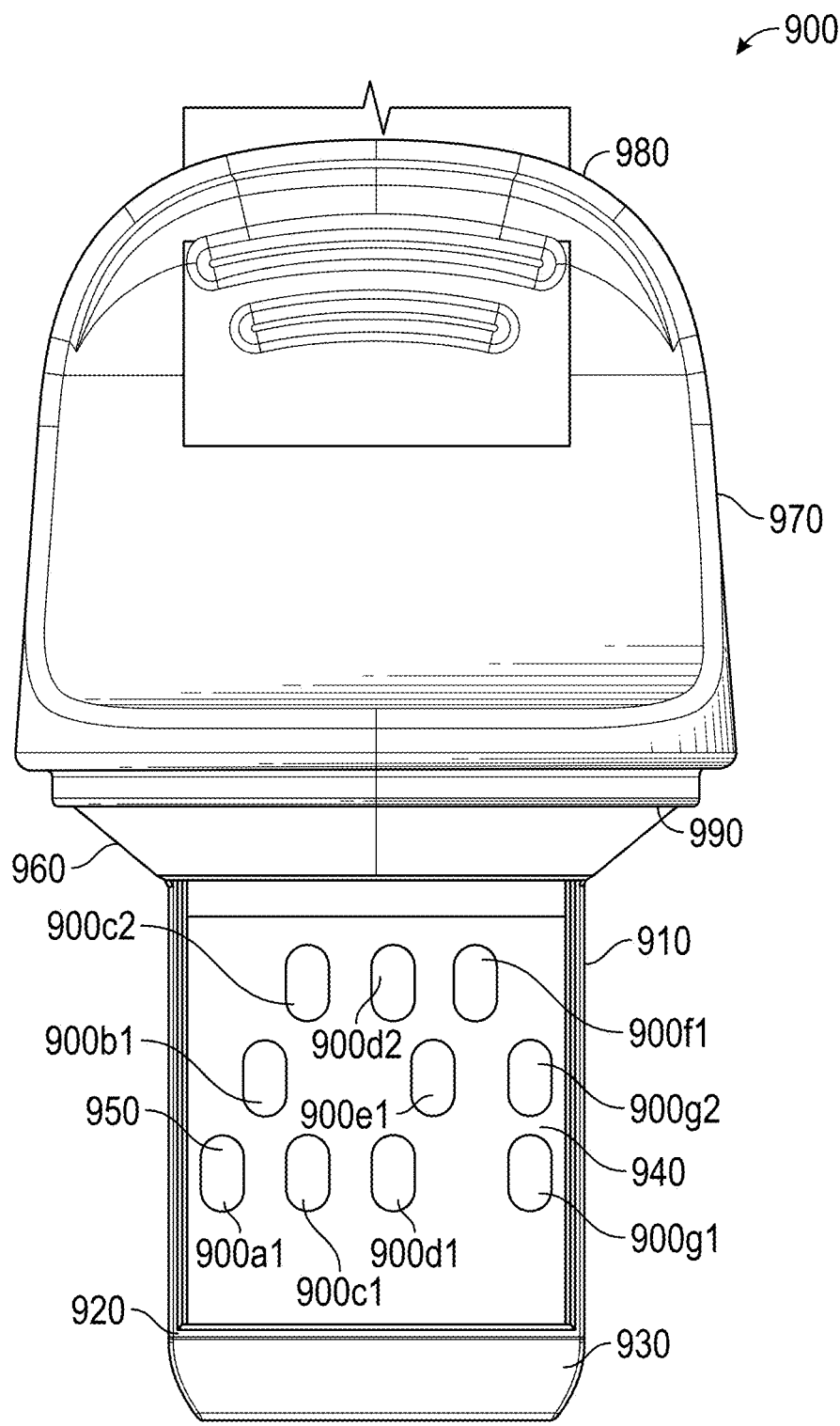
FIG. 12A illustrates a top view of a sensor assembly proximal end configured with one embodiment of a sensor with a plurality of electrical contacts.

As discussed above, the sensor assembly can accommodate different sensors. For example, as shown in FIGS. 11A-11C, the sensor assembly 800*a* has a connector assembly 840*a* has a top connector assembly 842*a* and bottom connector assembly 844*a* that can accommodate and retain the sensor. The proximal end of the sensor has a plurality of electrical contacts on the sensor that are located on the sensor side 812*a* of the sensor tab 810*a*. FIG. 12A illustrates an example of a sensor assembly proximal end 900 with the sensor placed on the sensor tab. The sensor assembly proximal end 900 includes the connector assembly 970 with a sensor tab 910 and lip 930 on the proximal end. The sensor 940 is retained between the two parts of the connector assembly 970 such that the sensor 940 protrudes from both the opening 990 of the top connector assembly 960 and also from the distal end 980 of the connector assembly 970. The proximal end of the sensor 940 has a plurality of electrical contacts on its surface (e.g. electrical contact 900*a*1, electrical contact 900*b*1, electrical contact 900*c*1, electrical contact 900*c*2, electrical contact 900*d*1, electrical contact 900*d*2, electrical contact 900*e*1, electrical contact 900*f*1, electrical contact 900*g*1, electrical contact 900*g*2) that are configured to engage the contact tips 1170 of the plurality of pogo pins 1000.

As can be seen in FIG. 12A, the staggered electrical contacts on the surface of the sensor 940 are arranged in a plurality of rows. In the example shown in FIG. 12A, electrical contact 900*a*1 is in one row, electrical contact 900*b*1 is in a second row, electrical contact 900*c*1 and electrical contact 900*c*2 are in a third row, electrical contact 900*d*1 and electrical contact 900*d*2 are in a fourth row, electrical contact 900*e*1 is in a fifth row, electrical contact 900*f*1 is in a sixth row, and sensor assembly proximal end 900 electrical contact g1 and electrical contact 900*g*2 is in a seventh row. As will be further shown below, the plurality of pogo pins 1000 are arranged and retained in a similar configuration in the inner shield 600.

Figure 12B:
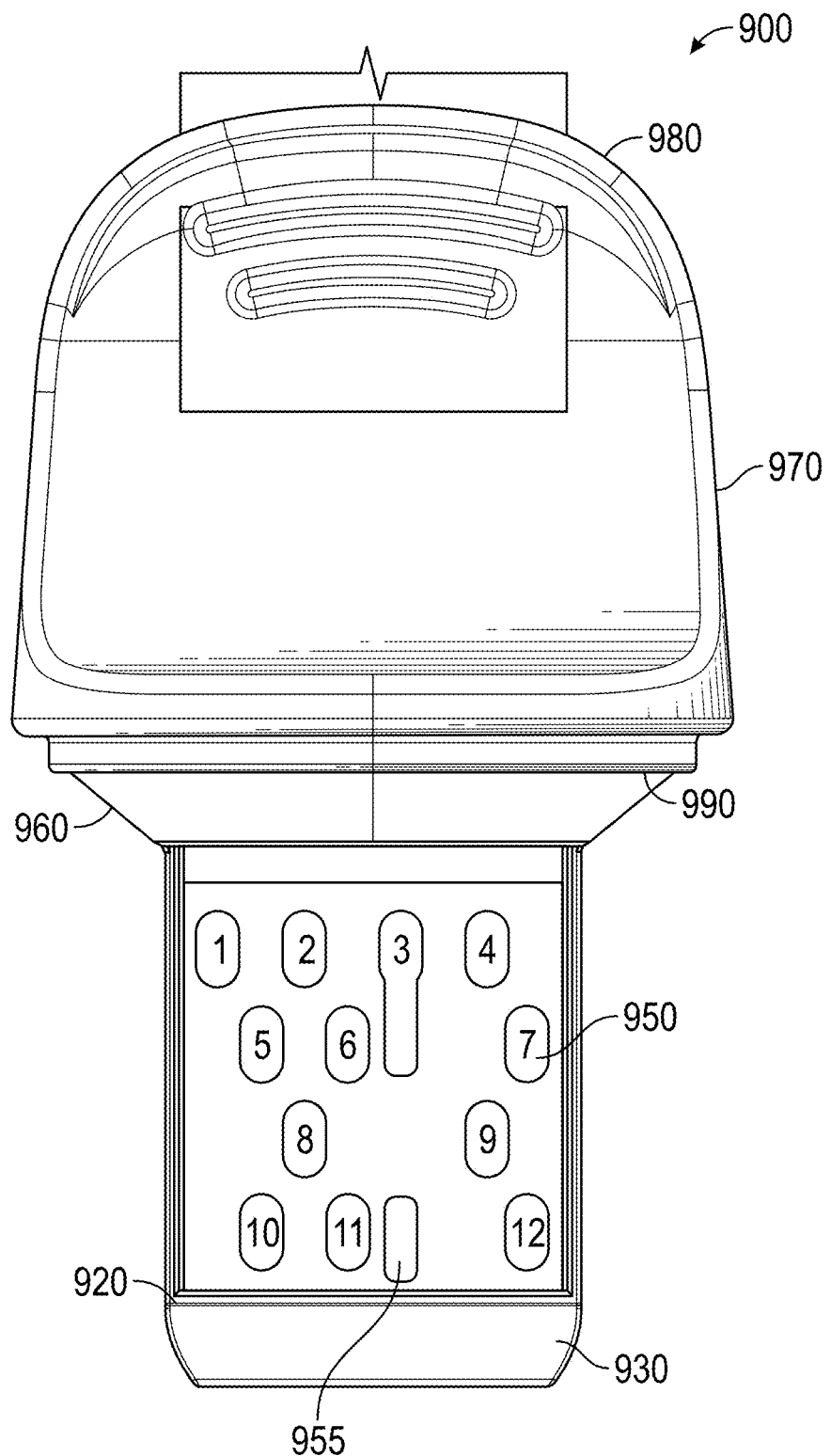
FIGS. 12B-12C illustrate a proximal end view of another embodiment of the sensor assembly proximal end configured with embodiments of a sensor with a plurality of electrical contacts wherein a ground trace is included.
Figure 12C:
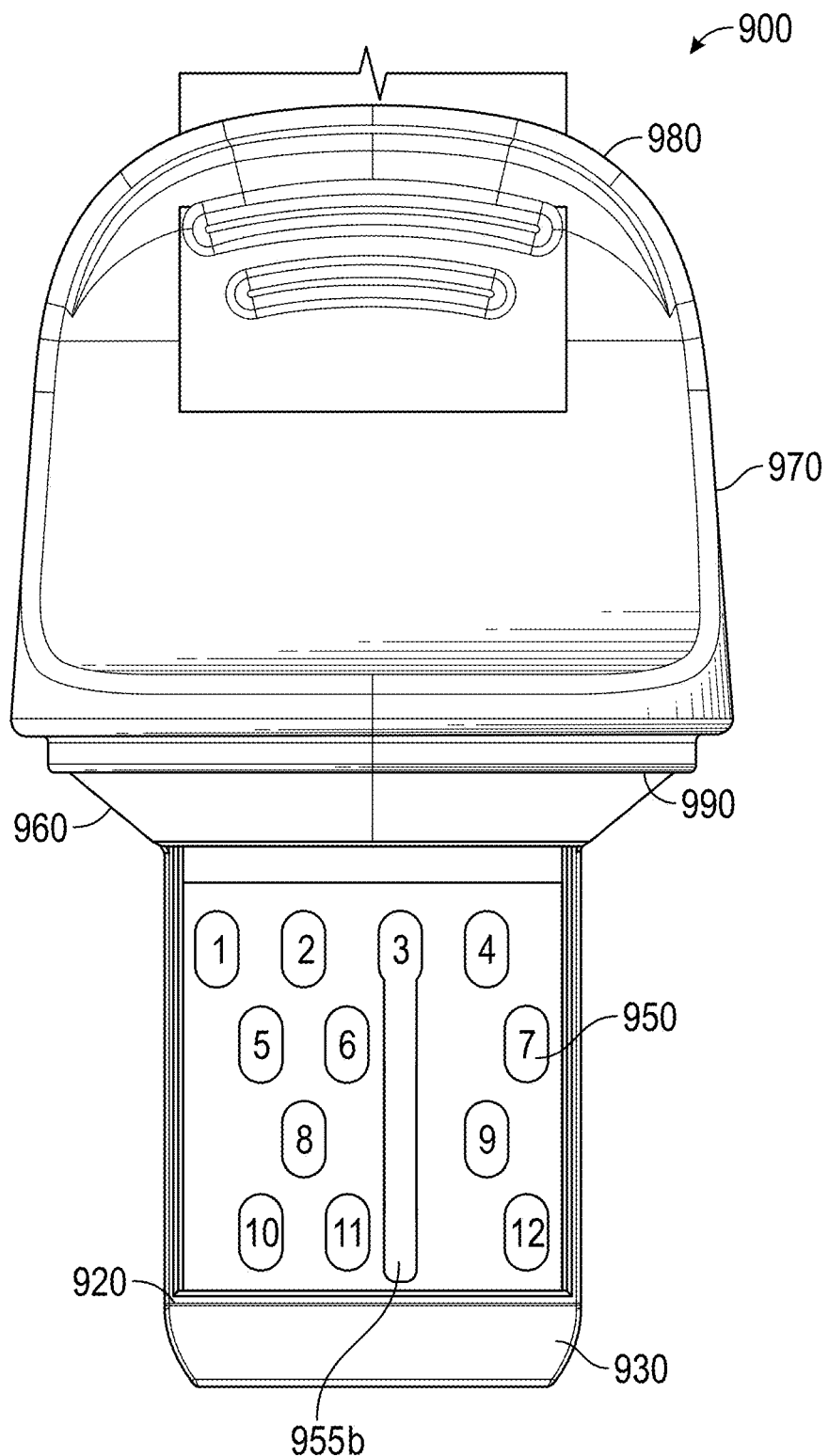

FIG. 12B illustrates an embodiment of the sensor assembly proximal end 900 wherein the plurality of traces 950 includes a ground trace 955. As seen in FIG. 12B, the ground trace 955—labeled as trace 950 "3"—has portions that extend from the proximal end of the sensor tab to the proximal end of the lip 930. As illustrated in FIG. 12C, in some embodiments, the ground trace 955*b* is electrically connected entirely on the surface of the sensor tab. In other embodiments, as illustrated in FIG. 12B, the ground trace 955 has portions that are electrically connected beneath the surface of the sensor. In other embodiments, the ground trace 955 is intermittently connected across the surface of the sensor.

In some embodiments, the ground trace 955 can serve as a grounding line to discharge any buildup of static electricity in the sensor assembly. In some embodiments, to prevent damage to the connector 200 or the sensor assembly, the sensor assembly can be discharged before certain electrical connections are formed between the plurality of pogo pins 1000 and the traces 950 (e.g. whether some or all of the traces 950). In some examples, in order to ground the sensor assembly before any of the plurality of pogo pins 1000 contacts any of the plurality of traces 950, the ground trace 955 can be configured such that a portion of the connector 200 will contact the ground trace 955 before any of the other traces 950. For example, as illustrated in FIG. 12B, in some embodiments, the ground trace 955 extends further in a proximal direction than the other traces in the same row (e.g. trace "10", trace "11", and trace "12"). In this way, as the sensor side 920 of the sensor assembly proximal end 900 is inserted into the connector 200, a structure within the connector 200 will contact the ground trace 955 to first discharge the sensor assembly before the plurality of pogo pins 1000 contact the remaining traces 950 on the sensor side 920.

In order to ground the sensor assembly, a portion of the connector 200 can be grounded. In some embodiments the outer shield 300 is connected to ground. In other embodiments, the inner shield 600 is connected to ground. As discussed above, in some examples, a portion of the connector 200 that is configured to contact the sensor side 920 of the sensor assembly is connected to the grounded portion of the connector 200 (for example, the outer shield 300 or the inner shield 600). In some examples, one of the plurality of pogo pins 1000 is connected to ground and can be configured to contact the ground trace 955. In other examples, the inside surface of the connector 200 includes a structure (for example, a protrusion or extended piece such as a flexible wire or contact) near the opening of the connection which is configured to contact the ground trace 955 to ground the sensor assembly before contact is made with any other electrically conductive portion of the connector 200.

Figure 13A:
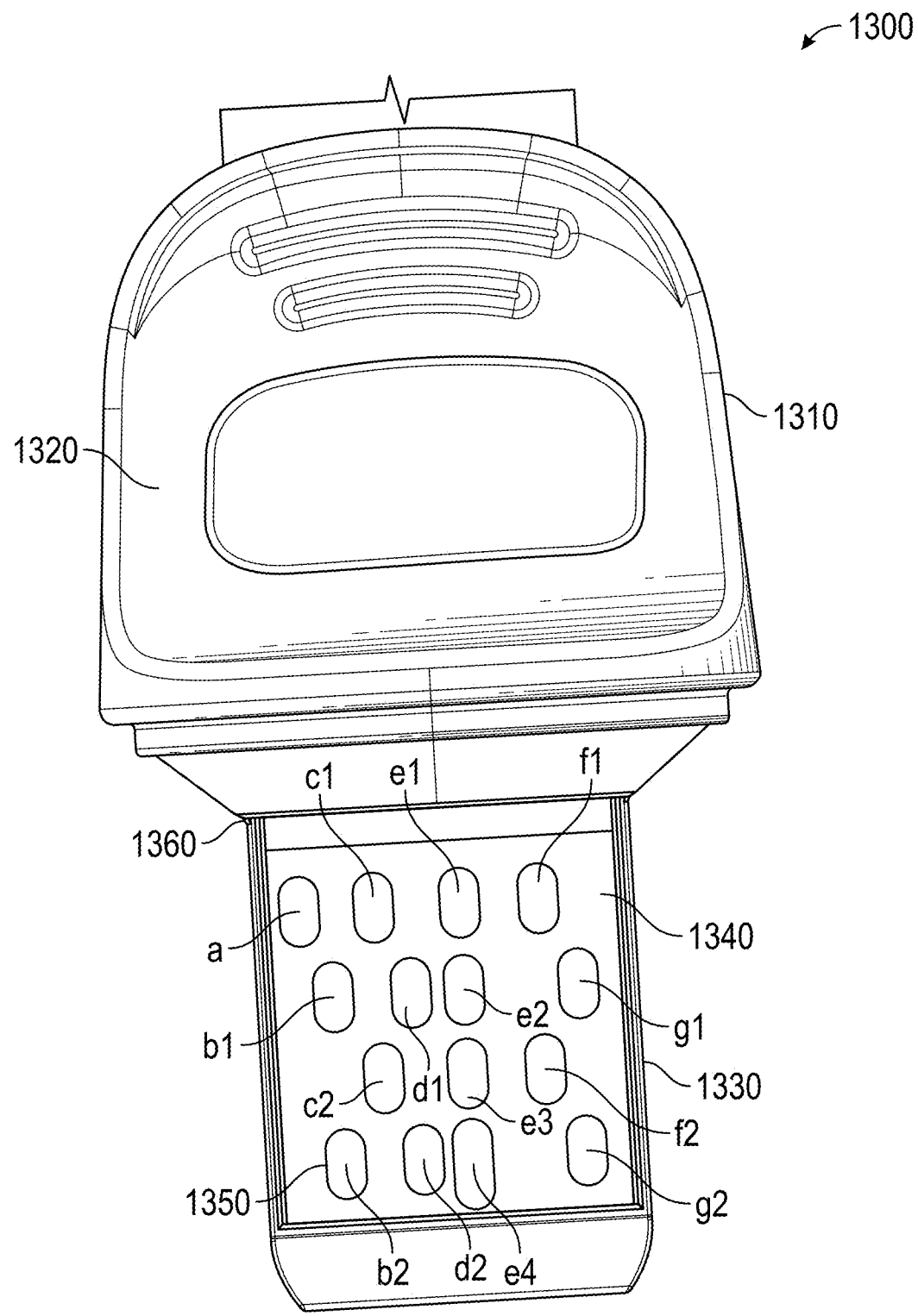
FIGS. 13A-13B illustrate top views of one embodiment of a sensor assembly and a connector that are configured to interact.
Figure 13B:
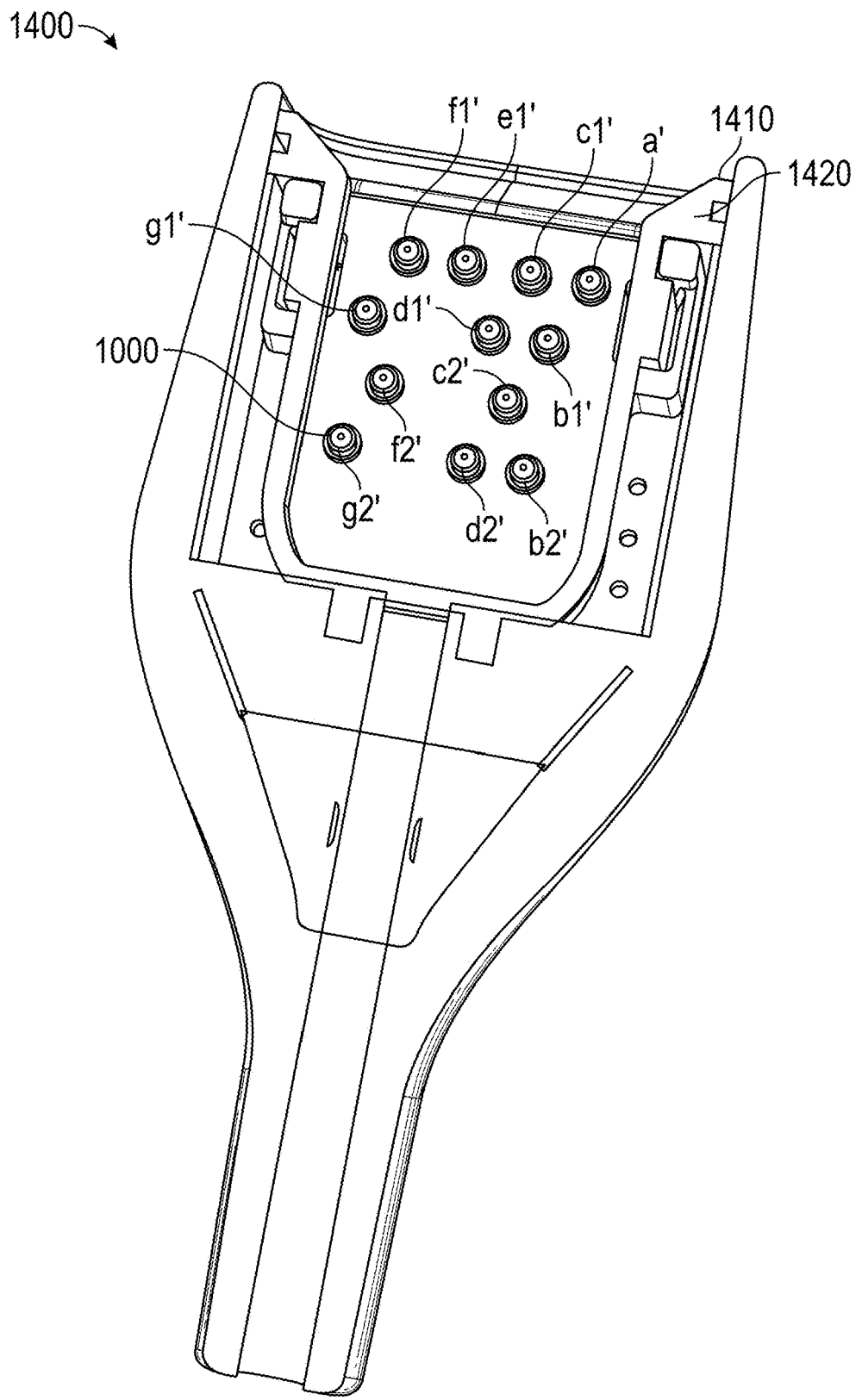

FIGS. 13A-13B show an example of a connector with pogo pins 1000 that correspond with the electrical contacts on the sensor of the corresponding sensor assembly. The sensor assembly proximal end 1300 shown in FIG. 13A has a connector assembly 1310 with a top connector assembly 1320 that has an opening 1360 from which the sensor 1340 protrudes from. The sensor 1340 is contained on the sensor tab 1330 and has a plurality of electrical contacts 1350. FIG. 13B shows a cross-sectional view of the connector 1400 with a plurality of pogo pins 1000. In the example sensor assembly and connector shown in FIGS. 13A-13B, the configuration of the electrical contacts on the sensor 1340 and pogo pins 1000 in the connector 1400 are arranged to establish a plurality of electrical connections between the sensor 1340 and the connector 1400. The sensor 1340 has a plurality of electrical contacts—electrical contact a, electrical contact b1, electrical contact b2, electrical contact c1, electrical contact c2, electrical contact d1, electrical contact d2, electrical contact e1, electrical contact e2, electrical contact e3, electrical contact e4, electrical contact f1, electrical contact f2, electrical contact g1, and electrical contact g2. The connector 1400 has a plurality of pogo pins 1000—pogo pin contact a', pogo pin contact b1', pogo pin contact b2', pogo pin contact c1', pogo pin contact c2', pogo pin contact d1', pogo pin contact d2', pogo pin contact e1', pogo pin contact e2', pogo pin contact e3', pogo pin contact e4', pogo pin contact f1', pogo pin contact f2', pogo pin contact g1', and pogo pin contact g2'. These pogo pins 1000 contact the plurality of electrical contacts 1350 to establish a plurality of electrical connections. In the present example, once the sensor tab 1330 is fully inserted into the connector 1400, the following pogo pins contact the following electrical contacts: pogo pin contact a' with electrical contact a, pogo pin contact b1' with electrical contact b1, pogo pin contact b2' with electrical contact b2, pogo pin contact c1' with electrical contact c1, pogo pin contact c2' with electrical contact c2, pogo pin contact d1' with electrical contact d1, pogo pin contact e1' with electrical contact e1, pogo pin contact f1' with electrical contact f1, pogo pin contact f2' with electrical contact f2, pogo pin contact g1' with electrical contact g1, and pogo pin contact g2' with electrical contact g2.

As the sensor tab 1330 is inserted into the opening 1410 of the sensory assembly receiver 1420, the pogo pins 1000 proximal to the opening 1410 will contact the length of the sensor 1340 before connecting with its corresponding electrical contacts. For example, pogo pin contact a1' will contact the proximal end of the sensor 1340 before reaching the electrical contact a. Therefore, in one configuration, to prevent short circuiting, the electrical contacts on the sensor 1340 and the corresponding pogo pins 1000 in the connector 1400 are arranged in staggered rows to minimize the electrical contacts that the proximal end of each of the pogo pins 1000 will touch as the sensor tab 1330 is inserted into the connector 1400. For example, as seen in FIG. 13A, the electrical contact b1 is located proximal and between the electrical contact a and electrical contact c1. In this way, the pogo pin contact a1' and pogo pin contact c1' on either side of the pogo pin contact b1' will not contact the electrical contact b1 as the sensor tab 1330 is inserted.

Another potential benefit of the staggering of the electrical contacts on the sensor tab 1330 and the pogo pins 1000 in the connector 1400 is the increase in electrical connections that a sensor can have given the configuration of the sensor tab 1330 and the inner shield 600 of the connector 1400. As discussed earlier, because of the configuration of the pogo pins 1000 and the electrical contacts on the sensor tab 1330, the disclosed configuration of the sensor assembly and connector can accommodate sensors requiring a large number of electrical contacts.

Although this disclosure has been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

What is claimed is:

1. A connector and sensor assembly, the assembly including:
   a connector including:
      an opening with an internal surface, wherein a bottom side of the inner surface comprises a detent and a receptor, wherein the detent forms a groove on the bottom side of the internal surface, and
      a plurality of retractable electrical connectors extending downward from a top side of the internal surface; and
   a sensor assembly including a sensor tab, a top side of the sensor tab including a plurality of electrical contacts, a bottom side of the sensor tab including a key detent and a key receptor, wherein the key receptor includes a raised structure,
   wherein the sensor tab of the sensor assembly is configured to be removably inserted into the opening of the connector, and wherein, when inserted in a correct orientation, the key receptor is configured to engage with the receptor and engagement between the detent and the key detent is configured to provide a click feedback to indicate that the sensor tab has been correctly inserted.

2. The assembly of claim 1, wherein the receptor only allows a sensor assembly with a corresponding key receptor to fit into the connector.

3. The assembly of claim 1, wherein the sensor assembly further comprises a body portion coupled to the sensor tab at a first end of the body portion, the body portion configured to be held by a user during insertion of the sensor tab into the connector.

4. The assembly of claim 3, wherein a top surface of the body portion is concave.

5. The assembly of claim 3, wherein a second end of the body portion opposite the first end comprises an opening configured to receive a sensor.

6. The assembly of claim 5, wherein a height of the body portion is greater at the first end than at the second end.

7. The assembly of claim 3, wherein a top surface of the connector includes a first color indicator and a top surface of the body portion of the sensor assembly include a second color indicator, wherein the first color indicator and second color indicator match each other.

8. The assembly of claim 1, wherein the plurality of retractable electrical connectors are arranged in a staggered spatial configuration that spans a plurality of rows on the internal surface.

9. The assembly of claim 1, wherein the plurality of electrical contacts includes an electrical contact that serves as a grounding line.

10. The assembly of claim 9, wherein at least one of the plurality of retractable electrical connectors is configured to contact the electrical contact that serves as the grounding line before electrical connection is established between a remainder of the plurality of retractable electrical connectors and a remainder of the plurality of electrical contacts.

11. The assembly of claim 1, wherein the plurality of electrical contacts are arranged in a staggered configuration.

12. The assembly of claim 11, wherein the plurality of electrical contacts are arranged into a first row of electrical contacts, a second row of electrical contacts, and a third row of electrical contacts.

13. The assembly of claim 1, wherein the top surface of the sensor tab further comprises a first protrusion and a second protrusion.

14. The assembly of claim 13, wherein the first protrusion and the second protrusion extend from a free end of the sensor tab toward a body portion of the sensor assembly connected to the sensor tab.

15. The assembly of claim 13, wherein the first protrusion and the second protrusion are on opposite sides of the plurality of electrical contacts.

16. The assembly of claim 15, wherein the first protrusion and the second protrusions are along opposite edges of the sensor tab across a width of the sensor tab.

17. The assembly of claim 13, wherein a height of the first protrusion and the second protrusion ensures that the sensor tab is inserted through the opening at a distance from a top side of the opening.

18. The assembly of claim 1, wherein the plurality of retractable electrical connectors are pogo pins.

19. A connector and sensor assembly, the assembly including:

a connector including:
- an opening with an internal surface, wherein a bottom side of the inner surface comprises a detent and a receptor, and
- a plurality of retractable electrical connectors extending downward from a top side of the internal surface; and a sensor assembly including a sensor tab, a top side of the sensor tab including a plurality of electrical contacts, a bottom side of the sensor tab including a key detent and a key receptor, wherein the key receptor includes a raised structure, wherein the sensor tab of the sensor assembly is configured to be removably inserted into the opening of the connector, and wherein, when inserted in a correct orientation, the key receptor is configured to engage with the receptor and engagement between the detent and the key detent is configured to provide a click feedback to indicate that the sensor tab has been correctly inserted, wherein the plurality of electrical contacts includes an electrical contact that serves as a grounding line and wherein at least one of the plurality of retractable electrical connectors is configured to contact the electrical contact that serves as the grounding line before electrical connection is established between a remainder of the plurality of retractable electrical connectors and a remainder of the plurality of electrical contacts.

20. The assembly of claim 19, wherein the plurality of electrical contacts are arranged in a staggered configuration.

\* \* \* \* \*